United States Patent
Rana

(10) Patent No.: US 8,329,681 B2
(45) Date of Patent: Dec. 11, 2012

(54) METHODS AND COMPOSITIONS FOR THE EFFICIENT DELIVERY OF THERAPEUTIC AGENTS TO CELLS AND ANIMALS

(75) Inventor: Tariq M. Rana, Shrewsbury, MA (US)

(73) Assignee: University of Massachusetts, Boston, MA (US)

( * ) Notice: Subject to any disclaimer, the term of this patent is extended or adjusted under 35 U.S.C. 154(b) by 1401 days.

(21) Appl. No.: 11/503,531

(22) Filed: Aug. 11, 2006

(65) Prior Publication Data

US 2007/0260055 A1 Nov. 8, 2007

Related U.S. Application Data

(60) Provisional application No. 60/707,805, filed on Aug. 11, 2005.

(51) Int. Cl.
*A61K 31/56* (2006.01)
(52) U.S. Cl. .................................. 514/182; 514/169
(58) Field of Classification Search .................. 514/183
See application file for complete search history.

(56) References Cited

U.S. PATENT DOCUMENTS 5,869,715 A 2/1999 Nantz et al.
7,514,099 B2 * 4/2009 Chen et al. .................... 424/450

FOREIGN PATENT DOCUMENTS

| WO | WO-03/102150 A2 | 12/2003 |
| WO | WO-2004/105697 A2 | 12/2004 |
| WO | WO-2004/108898 A2 | 12/2004 |
| WO | WO-2006/048225 A1 | 5/2006 |
| WO | WO-2006/105697 A1 | 10/2006 |

OTHER PUBLICATIONS

Jiang, Yu-Lin et al., "Syntheses of Long-Chain Quaternary Ammonium Salts from Fatty Alcohols by Microwave Irradiation," *JAOCS*, vol. 73(7):847-850 (1996).
Svobodová, Eva et al., "Metal Ion Transport Through Bulk Liquid Membrane Mediated by Cationic Ligand Surfactants," *Collect. Czech. Chem. Commun.*, vol. 70:441-465 (2005).
International Search Report for Application No. PCT/US2006/031542, dated Apr. 2, 2007.
International Preliminary Report on Patentability for Application No. PCT/US2006/031542, dated Feb. 12, 2008.

* cited by examiner

*Primary Examiner* — Jeffrey S. Lundgren
*Assistant Examiner* — Meghan Finn
(74) *Attorney, Agent, or Firm* — Nelson Mullins Riley & Scarborough LLP; Debra J. Milasincic, Esq.

(57) ABSTRACT

The present invention provides methods of carrying out the safe and reliable preparation of lipids comprising quaternary amines. Such lipids are especially suited for introducing therapeutic agents into cells or organisms. In particular, the lipids of the invention are suitable for the efficient transfer of gene therapy agents into mammalian cells or organisms in a cell type specific or tissue specific manner.

6 Claims, 17 Drawing Sheets

| Reactants | Products | | Reaction Conditions | Yield |
|---|---|---|---|---|
| (structure with C₁₃H₂₇, N, OH, O—Chol, MeI) | (product structure with cholesterol-TC group) | 9 | 80 °C, 150W, 300psi, 3.5h, neat | 81 |
| (structure with C₁₇H₃₃, N, OH, MeI) | (product structure with C₁₇H₃₃) | 10 | 80 °C, 150W, 300psi, 3.5h, neat | 40 |
| Cl–CH₂–N(R)(R), OH, NaOH | (quaternary ammonium product with R groups and OH) | 11 | 80 °C, 150W, 300psi, 3h, 2-chloroethanol (excess) | 45 |

Fig. 2

Synthesis of Transfast & Transfast-Chol (Scheme 3):

Synthesis of DTDEAC under Microwave conditions (Scheme 4):

| siRNA nM | TransFast-chol In H₂O | DOTAP-chol In H₂O | TransFast-chol In Hepes | DOTAP-chol In Hepes | TransFast-chol In MES | DOTAP-chol in MES |
|---|---|---|---|---|---|---|
| CDK9 siRNA 150 nM | -52% | -79% | -45% | -53% | -32% | -48% |
| CDK9 siRNA 75 nM | -48% | -77% | -76% | -73% | -35% | -60% |
| CDK9 siRNA 37 nM | -40% | -65% | -79% | -60% | -38% | -70% |

Fig. 12 and# METHODS AND COMPOSITIONS FOR THE EFFICIENT DELIVERY OF THERAPEUTIC AGENTS TO CELLS AND ANIMALS

RELATED INFORMATION

This application claims priority to U.S. Provisional Application No. 60/707,805, filed Aug. 11, 2005, entitled "METHODS AND COMPOSITIONS FOR THE EFFICIENT DELIVERY OF THERAPEUTIC AGENTS TO CELLS AND ANIMALS." The contents of any patents, patent applications, and references cited throughout this specification are hereby incorporated by reference in their entireties.

STATEMENT AS TO FEDERALLY SPONSORED RESEARCH

Funding for the work described herein was at least in part provided by the federal government under grant numbers AI 41404 and AI 43198, awarded by the United States National Institutes of Health and the National Institute of Allergy and Infectious Diseases.

BACKGROUND

The development of new forms of therapeutics which use macromolecules such as proteins or nucleic acids as therapeutic agents has created a need to develop new and effective means of delivering such molecules to their appropriate cellular targets. Therapeutics based on either the use of specific polypeptide growth factors or specific genes to replace or supplement absent or defective genes are examples of therapeutics which may require such new delivery systems.

Gene therapy has become an increasingly important mode of treating various diseases. The potential for providing effective treatments, and even cures, has stimulated an intense effort to apply this technology to diseases for which there have been only limited effective treatments. Recent progress in this area has indicated that gene therapy may have a significant impact not only on the treatment of single gene disorders, but also on other more complex diseases such as cancer. Gene therapy agents include expressible gene constructs but also RNA interference agents (RNAi). There has recently been a great deal of interest in the use of RNAi for basic research purposes and for the development of therapeutics to treat, e.g., disorders and/or diseases associated with unwanted or aberrant gene expression.

Success of a gene therapy protocol largely depends upon the vehicle used to deliver the gene. A variety of means exist to introduce a gene inside the cell including physical means such as microinjection (Capecchi, M. R. Cell (1980) 22:479-485), electroporation (Pacqereau, L. et al. Anal. Biochem. (1992) 204:147-151) and particle bombardment (Yang, N.-S. et al. Proc. Natl. Acad. Sci. USA (1990) 87:9568-9572)), biological means such as viruses (Ferry, N. et al. Proc. Natl. Acad. Sci. (1991) 88:8377-8381) and chemical means such as calcium phosphate (Wiegler, M. et al. Cell (1977) 11:223-232), DEAE dextran (Ishikawa, Y. et al. Nucl. Acid Res. (1992) 20:4367-4370), polylysine (Wu, G. Y. et al. J. Biol. Chem. (1988) 263:4429-4432) and cationic liposomes (Felgner, P. L. et al. Proc. Natl. Acad. Sci. (1987) 84:7413-7417)). Clinical application of such therapies depends not only on the efficacy of new delivery systems but also on their safety and on the ease with which the technologies underlying these systems can be adapted for large scale pharmaceutical production, storage, and distribution of the therapeutic formulations. Thus, an ideal vehicle for the delivery of exogenous agents into cells and tissues should be highly efficient in therapeutic agent delivery, safe to use, easy to produce in large quantity and have sufficient stability to be practicable as a pharmaceutical.

Accordingly a need exists for new and practical ways of making reagents suitable for introducing therapeutic agents into cells, in vitro and in vivo, and in particular, for use in developing human therapeutics.

SUMMARY OF THE INVENTION

The present invention is based on the surprising discovery that heretofore hazardous and unreliable reactions for making quaternary amines can be efficiently carried out using microwave irradiation. Accordingly, compounds suitable for derivatization, e.g., substitution, with a quaternary ammonium salt moiety, for example, compounds which form lipids, can be modified to acquire a quaternary ammonium moiety using microwave irradiation using bench top conditions.

In one embodiment, compounds that can be used to form lipids can be modified to acquire a quaternary amine, and thereby, an additional functional moiety, for example, a cholesteryl group, using microwave irradiation. Such lipids so modified are suitable compositions for the transfer of therapeutic agents, for example, gene therapy agents such as vectors or RNAi agents and/or proteins, peptides, or small molecules, into cells, cellular or biological spaces, and/or organisms.

In certain embodiments, the new lipids created by the methods of the invention are suitable for introducing therapeutic agents into cells or organisms, as lipid compositions, lipid dispersions, or as liposomes.

In another embodiment, the compositions of the invention are suitable, when mixed in particular ratios, for tailoring the cell type/tissue specific targeting of such gene therapy agents.

In another embodiment, nucleic acid agents, previously effective in only high amounts, are now active targeting agents in low amounts when delivered using the methods and compositions of the invention.

Still further, in another embodiment, the new lipids created by the methods are suitable for efficiently transferring nucleic acid agents, e.g., RNAi agents, into cells, in particular, into cell types and tissues previously difficult to target.

In yet another embodiment, the new lipids created by the methods are suitable for efficiently transferring proteins (e.g., antibodies), peptides, or small molecules into cells.

Accordingly, the invention has several advantages which include, but are not limited to, the following:

providing new methods for creating quaternary amine lipids using safe and reliable methods using, for example, microwave irradiation, providing new lipid compounds comprising quaternary amines, providing lipids comprising quaternary amines suitable for the transfer of therapeutic agents into cells, providing lipid compositions suitable for use in liposomes for the efficient transfer of therapeutic agents into cells, cellular or biological spaces, and/or organisms, providing lipid compositions for the high efficiency transfer of gene therapy agents, e.g., nucleic acid agents, e.g., viral vectors (e.g., lentivirus derived vectors), DNA plasmids, DNA (single stranded or multistranded), RNA (single stranded or multistranded), and/or RNAi agents (e.g., siRNA, shRNA, microRNA agents, and/or morpholinos) into cells and/or organisms to achieve in vitro and/or in vivo gene modulation, repair, and/or expression, providing lipid compositions for the high efficiency transfer of proteins (e.g., antibodies), peptides, or small molecules into cells and/or organisms, and methods and compositions using the lipids of the invention for the cell type and/or tissue specific targeting of therapeutic agents in vitro and/or in vivo.

Other features and advantages of the invention will be apparent from the following detailed description and claims.

BRIEF DESCRIPTION OF THE DRAWINGS

FIG. 2 summarizes the reactants and reaction conditions used to produce compounds 9-11 of the invention using microwave irradiation, as well as examples of product yields.

FIG. 12 shows a table indicating the efficacy of the lipid compounds of the invention for delivery of a gene knock down RNAi agent whereby an ~80% reduction in target gene expression as compared to a control is achieved using an RNAi agent in amounts as low as 37 nM.

DETAILED DESCRIPTION OF THE INVENTION

Figure 1:
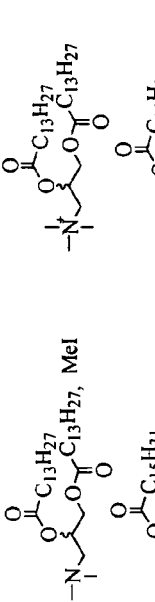
FIG. 1 summarizes the reactants and reaction conditions used to produce compounds 1-8 of the invention using microwave irradiation, as well as examples of product yields.
Figure 3:
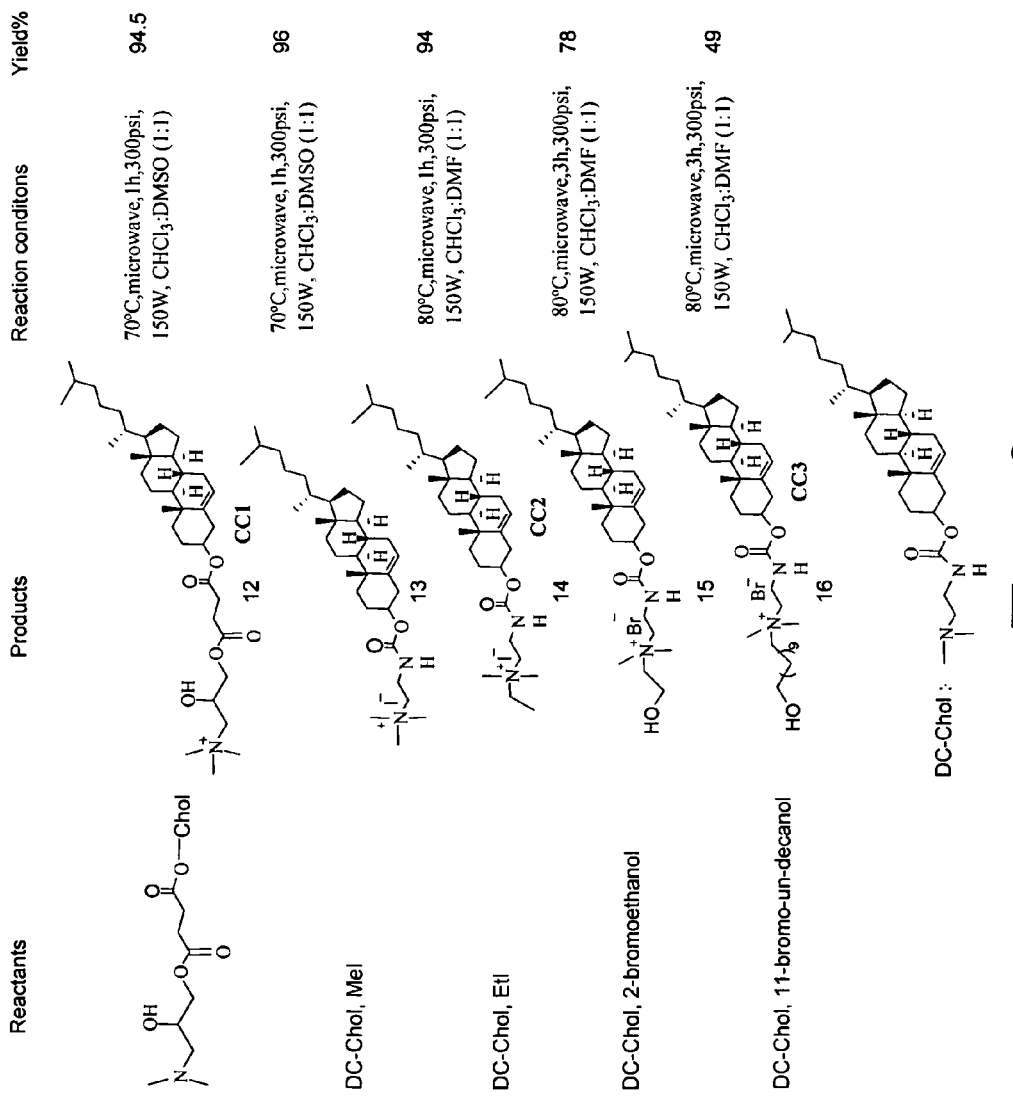
FIG. 3 summarizes the reactants and reaction conditions used to produce compounds 12-16 of the invention using microwave irradiation, as well as examples of product yields.

In order to provide a clear understanding of the specification and claims, the following definitions are conveniently provided below.

Definitions

The general term "quaternary ammonium compound" or "quaternary ammonium salt" or "ammonium salt moiety" describes a compound having a quaternary substituted nitrogen atom and having one or more, e.g., two, organic group moieties. In a particular embodiment, the quaternary nitrogen atom is substituted by four organic group moieties, including, but not limited to, aryl, substituted aryl, $C_{1-30}$-alkyl, substituted $C_{1-30}$-alkyl, $C_{1-30}$-alkenyl, substituted $C_{1-30}$-alkenyl, $C_{1-30}$-alkynyl, substituted $C_{1-30}$-alkynyl, cholesteryloxy, and/or cholesteryloxy succinate. Particular quaternary ammonium salts are described herein.

Furthermore, in certain embodiments, a "quaternary ammonium compound" or "quaternary ammonium salt" is a compound that can be produced using one of the methods of the invention, i.e., preparing a reaction mixture comprising (i) an amine and (ii) a substrate containing a leaving group; and exposing said reaction mixture to microwave energy from a microwave source, e.g., a controllable microwave source. The amine can be primary, secondary, or tertiary. In a particular embodiment of the invention, the amine is tertiary.

Examples of quaternary ammonium compounds of the invention include, but are not limited to, compounds 1, 2, 3, 4, 5, 6, 7, 8, 9, 10, 11, 12, 13, 14, 15 and 16.

The term, "a substrate containing a leaving group" is any organic compound substituted with a leaving group. In particular embodiments, the organic compound is a $C_{1-30}$-alkyl group or an aryl group. The term "leaving group" as used herein refers to any group that departs from a molecule in a substitution reaction by breakage of a bond. The term "leaving group" also generally refers to groups readily displaceable by a nucleophile, such as an amine. In a particular embodiment, the term "leaving group" refers to a radical that is easily displaced by a nucleophile in an $S_N2$ displacement reaction, or are easily eliminated in a condensation or cyclization reaction. Such leaving groups are well known in the art. Examples of such leaving groups include, but are not limited to, bromo, chloro, iodo, —OC(=O)R, —OCO$_2$R, —OPO(OR)$_2$, —OSOR, —OSO$_2$R, —OR, —OR$_2^+$, —SR$_2^+$, —SO$_2$R, —NR$_3^+$, —PR$_3^+$, —NO$_2$, or —CN, wherein R is hydrogen, $C_{1-10}$-alkyl, aryl, or heteroaryl. In particular embodiments, the leaving group, once displaced from the substrate, can form and/or act as the counter ion of the ammonium salt (which can in turn be replaced for a counter ion with more suitable properties, e.g., a pharmaceutically acceptable counter ion).

The term "subject" is intended to include animals, which are capable of suffering from, or afflicted with, a disorder, or any disorder involving, directly or indirectly, for example, a CDK9-related or mediated disorder. Examples of subjects include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from a disorder, for example, a CDK9-related or mediated disorder.

The term "therapeutic agent" refers to nucleic acid agents, protein or peptide agents, or small molecule agents, as further described herein.

The term "nucleic acid agent" refers to RNA or RNA molecules as well as DNA molecules. The term RNA refers to a polymer of ribonucleotides. The term "DNA" or "DNA molecule" or deoxyribonucleic acid molecule" refers to a polymer of deoxyribonucleotides. DNA and RNA can be synthesized naturally (e.g., by DNA replication or transcription of DNA, respectively). RNA can be post-transcriptionally modified. DNA and RNA can also be chemically synthesized. DNA and RNA can be single-stranded (i.e., ssRNA and ssDNA, respectively), or multi-stranded (e.g., double stranded, i.e., dsRNA and dsDNA, respectively), i.e., duplexed or annealed. The nucleic acid agent can also be modified, e.g., chemically, or comprise modified nucleotides or analogues, or, e.g., morpholine rings. Accordingly, the nucleic agent can be a morpholino oligo as described below. The nucleic agent can also be a vector, e.g., an expression vector, e.g., a plasmid or viral vector. Any of the foregoing nucleic acid agents are suitable to be complexed with the compounds, compositions, lipids, lipid dispersions, and/or liposomes of the invention for transfer into a cell, cellular or biological space, and/or animal. It is understood that any of the foregoing nucleic acid agents can also be further modified, for example, chemically modified to include modified bases, methyl groups, altered helical structure, and the like. It is also understood that the nucleic acid agent can comprise a target gene sequence or complement thereof.

The term "target gene sequence" refers to a gene sequence encoding a nucleic acid or polypeptide gene product which can be targeted for degradation, e.g., by RNA interference or a RISC-mediated pathway. The target sequenced can be an artificial, recombinant, or naturally occurring sequence. In one embodiment, the sequence encodes a gene product that, when expressed, e.g., at aberrant levels, results in an undesired phenotype, disorder, or disease, in for example, a model organism or human subject.

The term "RNA interference" ("RNAi") or "RNAi activity" refers to a selective intracellular degradation of RNA. RNAi occurs in cells naturally to remove foreign RNAs (e.g., viral RNAs). Natural RNAi proceeds via fragments cleaved from free dsRNA which direct the degradative mechanism to other similar RNA sequences. Alternatively, RNAi can be initiated by the hand of man, for example, to silence the expression of a target gene(s). RNA interference can be carried out using RNAi agents, e.g., siRNA, shRNA, i.e., short hairpin RNA, miRNA agents, i.e., microRNA agents of about 5 to about 60 nucleotides that target miRNAs, and/or single-stranded or multistranded RNA, DNA, or antisense oligonucleotides.

The term "small interfering RNA" ("siRNA") (also referred to in the art as "short interfering RNAs") refers to an RNA (or RNA analog) including strand(s) (e.g., sense and/or antisense strands) comprising between about 10-60 nucleotides (or nucleotide analogs) which is capable of directing or mediating RNA interference. For example, siRNA duplexes from about 5-18 nucleotides can be used. Alternatively, longer siRNA duplexes from about 18-60 nucleotides or 25-60 nucleotides, or ranges or intervals thereof can be used.

The term "vector" refers to a nucleic acid molecule (either DNA or RNA) capable of conferring the expression of a gene product when introduced into a host cell or host cell extract. The vector can be episomal or chromosomally (e.g., transgenically) integrated into the host cell genome. The vector can be a plasmid or a viral vector, e.g., a retrovirus or lentivirus or vector derived therefrom.

The term "modified nucleotide," "modified nucleic acid(s)" or "modified nucleic acid agent" refers to a non-standard nucleotide or nucleic acid, including non-naturally occurring ribonucleotides or deoxyribonucleotides. Preferred nucleotide analogs or nucleic acids are modified at any position so as to alter certain chemical properties, e.g., increase stability of the nucleotide or nucleic acid yet retain its ability to perform its intended function, e.g., have RNAi activity. Examples include methylation at one or more bases, e.g., O-methylation, preferably 2' O methylation (2'-O-Me), dyes which can be linked to the nucleic acid to provide for visual detection of the nucleic acid, and biotin moieties which can be used to purify the nucleic acid to which it is attached as well as any associated components bound to the biotinylated nucleic acid. Examples of modified nucleotides/nucleic acids are described in Herdewijn, *Antisense Nucleic Acid Drug Dev.*, 2000 August 10(4):297-310; U.S. Pat. Nos. 5,858,988; 6,291,438; Eckstein, *Antisense Nucleic Acid Drug Dev.* 2000 April 10(2): 117-21; Rusckowski et al. *Antisense Nucleic Acid Drug Dev.* 2000 October 10(5):333-45; Stein, *Antisense Nucleic Acid Drug Dev.* 2001 October 11(5): 317-25; Vorobjev et al. *Antisense Nucleic Acid Drug Dev.* 2001 April 11(2): 77-85; U.S. Pat. No. 5,684,143; US20050020521 A1, and US 20040204420 A1.

For example, modified nucleic acid agents can comprise one or more (e.g., about 1, 2, 3, 4, 5, 6, 7, 8, 9, 10, or more) sugar-modified nucleotides. Sugar-modified nucleotides useful in the invention include, but are not limited to: 2'-fluoro modified ribonucleotide, 2'-OMe modified ribonucleotide, 2'-deoxy ribonucleotide, 2'-amino modified ribonucleotide and 2'-thio modified ribonucleotide. The sugar-modified nucleotide can be, for example, 2'-fluoro-cytidine, 2'-fluoro-uridine, 2'-fluoro-adenosine, 2'-fluoro-guanosine, 2'-amino-cytidine, 2'-amino-uridine, 2'-amino-adenosine, 2'-amino-guanosine or 2'-amino-butyryl-pyrene-uridine. A preferred sugar-modified nucleotide is a 2'-deoxy ribonucleotide. Preferably, the 2'-deoxy ribonucleotide is present within the sense strand and, for example, can be upstream of the cleavage site referencing the antisense strand or downstream of the cleavage site referencing the antisense strand. A preferred sugar-modified nucleotide is a 2'-fluoro modified ribonucleotide. Preferably, the 2'-fluoro ribonucleotides are in the sense and antisense strands. More preferably, the 2'-fluoro ribonucleotides are every uridine and cytidine of the nucleic acid agent, e.g., siRNA molecule.

Modified nucleic acid agents can also comprise one or more (e.g., about 1, 2, 3, 4, 5, 6, 7, 8, 9, 10, or more) nucleobase-modified nucleotides. Nucleobase-modified nucleotides useful in the invention include, but are not limited to: 5-bromo-uridine, 5-iodo-uridine, 5-methyl-cytidine, ribothymidine, 2-aminopurine, 5-fluoro-cytidine, and 5-fluoro-uridine, 2,6-diaminopurine, 4-thio-uridine; and 5-amino-allyl-uridine and the like.

Modified nucleic acid agents can also comprise one or more (e.g., about 1, 2, 3, 4, 5, 6, 7, 8, 9, 10, or more) backbone-modified nucleotides, for example, a backbone-modified nucleotide containing a phosphorothioate group. The backbone-modified nucleotide can be within a sense strand, antisense strand, or preferably within a sense and antisense strand of, e.g., an siRNA molecule.

The term "morpholino," "morpholino oligo," "morpholinos," "PMO," or "phosphorodiamidate morpholino oligo" refers to nucleic acid agents that comprise a morpholine ring(s) instead of a ribose or deoxyribose ring and, e.g., are linked through a phosphorodiamidate group instead of a phosphate. Morpholinos are typically about 5 to about 25 nucleotides in length, and can be single stranded or multistranded and complexed with any of the delivery agents described herein for their introduction into cells, tissues and/or organisms.

The term "protein agent" or "peptide agent" refers to a compound comprising 2 or more amino acids linked by a peptide bond. Typical protein agents include antibodies or fragments thereof, e.g., Fab, Fab', F(ab')$_2$, Fv, scFv, Fd or Dab fragments.

The term "cell" refers to any eukaryotic cell which exhibits RNAi activity and includes, e.g., animal cells (e.g., mammalian cells, e.g., human or murine cells), plant cells, and yeast. The term includes cell lines, e.g., mammalian cell lines such as HeLa cells as well as embryonic cells, e.g., embryonic stem cells, fetal cells, primary cells, zygotes, and collections of cells in the form or context of, e.g., a tissue or a whole organism.

The term "organism" refers to multicellular organisms such as, e.g., *C. elegans, Drosophila*, mouse, rat, rabbit, pig, sheep, cow, primate or human.

Overview

The present invention is based, in part, on the surprising discovery that, compounds suitable for derivatization, e.g., substitution, with a quaternary ammonium salt, for example, compounds which form lipids, can be modified to acquire a quaternary ammonium moiety using microwave irradiation. Accordingly, the microwave assisted chemistry can be used to make compounds, in particular, lipid compounds described below, which can be used alone, in various combinations, e.g., ratios of two or more lipids, and/or as dispersions, or liposomes for the delivery of therapeutic agents, for example, small molecules, peptides, proteins, immunogens (for active immunotherapy), antibodies (for passive immunotherapy), nanoparticles, and/or nucleic acids to cells, cellular or biological spaces, and/or organisms. In particular, the compounds of the invention are suitable for the delivery of gene therapy agents, for example RNAi agents, for example, siRNA agents, for modulating gene expression in various cells, cell types, tissues, or in organisms.

Accordingly, in one embodiment the nucleic acid agent of the complex is single stranded, double stranded, DNA, RNA, a hybrid thereof, an RNAi agent, an siRNA agent, a short hairpin RNAi agent (shRNA), microRNA agent (miRNA), morpholino, or combination thereof, to either restore, diminish, or modulate gene function, as appropriate. The agents are typically delivered using the lipids of the invention, either alone, in combination with other lipids of the invention, as comprised with art recognized lipids or agents, or in different ratios as described herein, such that the desired cell, cellular or biological space, or tissue targeting is achieved.

Accordingly, in another embodiment, the therapeutic agent of the complex is a peptide or protein, e.g., an antibody or fragment thereof.

Accordingly, the invention also provides, cells, tissues, and/or organisms for example, recombinant cells, tissues, or organisms, for example transgenic animals, that have been modified (e.g., in vitro, ex vivo, or in vivo), using the improved delivery agents and methods of the invention.

In a preferred embodiment of the invention, the lipid/therapeutic agent complexes, as described herein, are suitable for preventing or treating a disease or disorder.

Still further, the invention provides delivery agents and methods/compositions for use in research or for diagnostic purposes, for example, as kits comprising reagents which can be complexed with a test reagent or therapeutic agent.

Further details for carrying out various aspects of the invention are provided in the following subsections below.

1. Compounds for Introducing Therapeutic Agents into Cells

In one embodiment, the present invention is directed to the compounds of the invention, the method of production of the compounds of the invention as well as the novel production of quaternary ammonium compounds, e.g., quaternary ammonium compounds known in the art, in a safe reliable manner, and the use of the compounds of the invention for introducing therapeutic agents into cells.

A. Compounds of the Invention

In one embodiment, the invention is a compound of the Formulas XIX and XX:

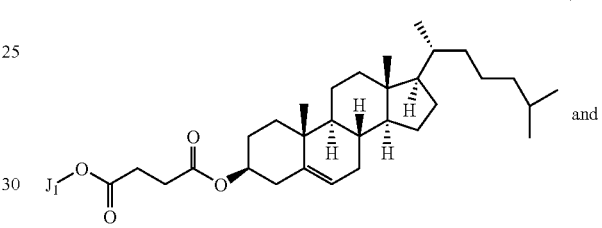

(XIX)
and

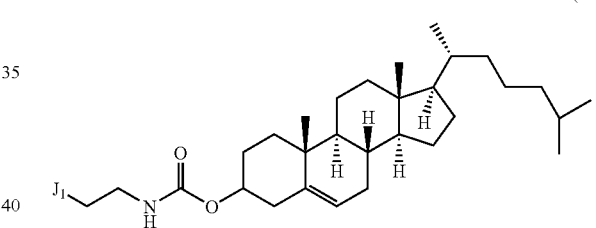

(XX)

wherein J$_1$ is a non-cyclic trialkylated ammonium derivatized (TAD) moiety.

The language "non-cyclic trialkylated ammonium derivatized (TAD) moiety" describes a moiety comprising an ammonium substituent linked via a direct bond or another structural linking moiety (e.g., moieties described herein as potential substituents, e.g., a methylene group), and which is additionally alkylated with three substituted or unsubstituted alkyl substituents, e.g., lower alkyl (e.g., C$_{1-10}$-alkyl) or lower hydroxy alkyl (e.g., lower hydroxy C$_{1-10}$-alkyl), with the proviso that such substituents do not include a cyclic ring structure.

In particular embodiments, the TAD of Formula XIX is selected from the group consisting of

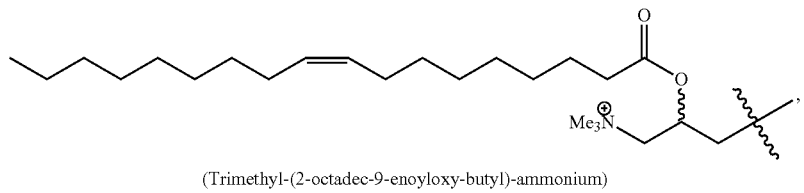

(Trimethyl-(2-octadec-9-enoyloxy-butyl)-ammonium)

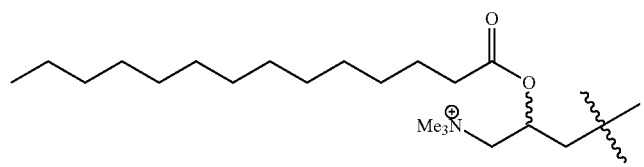
(Trimethyl-(2-tetradecanoyloxy-butyl)-ammonium)
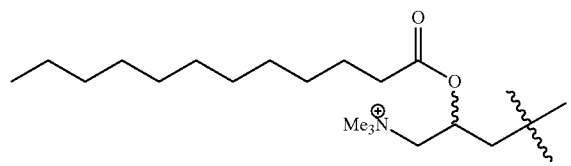
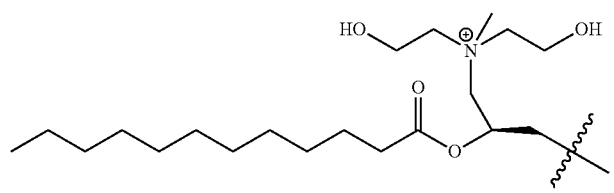
(Bis-(2-hydroxy-ethyl)-methyl-(2-tetradecanoyloxy-butyl)-ammonium)
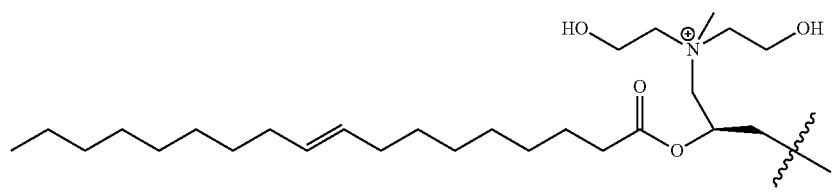
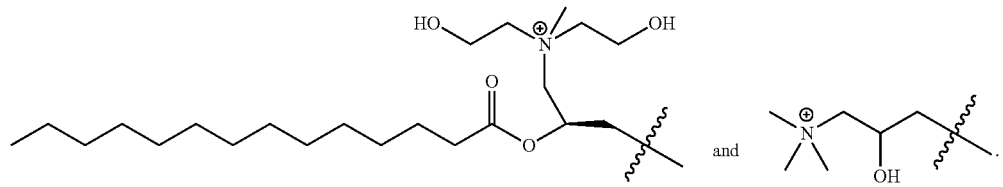
In particular embodiments, the TAD of Formula XX is selected from the group consisting of
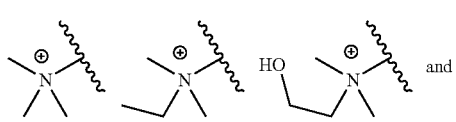 and
-continued
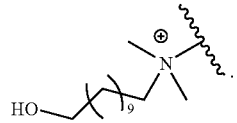
Another embodiment of the invention is directed to a compound of the formula:
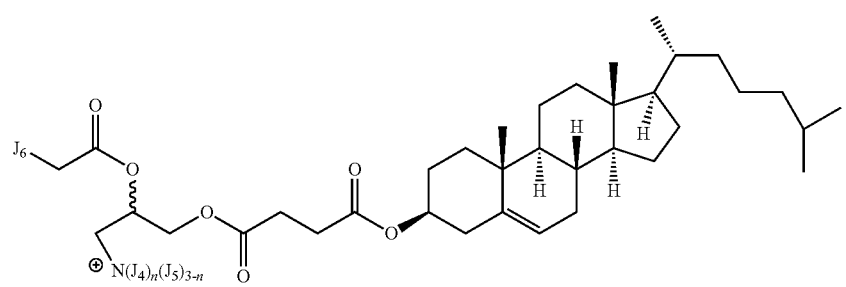

$J_4$ and $J_5$ are independently selected from the group consisting of lower alkyl (e.g., $C_{1-10}$-alkyl) and lower hydroxy alkyl (e.g., lower hydroxy $C_{1-10}$-alkyl);

$J_6$ is selected from the group consisting of aryl, substituted aryl, $C_{1-30}$-alkyl, substituted $C_{1-30}$-alkyl, $C_{1-30}$-alkenyl, substituted $C_{1-30}$-alkenyl, $C_{1-30}$-alkynyl, and substituted $C_{1-30}$-alkynyl; and n is 0-3.

In another embodiment, the invention relates to a compound of the formula:

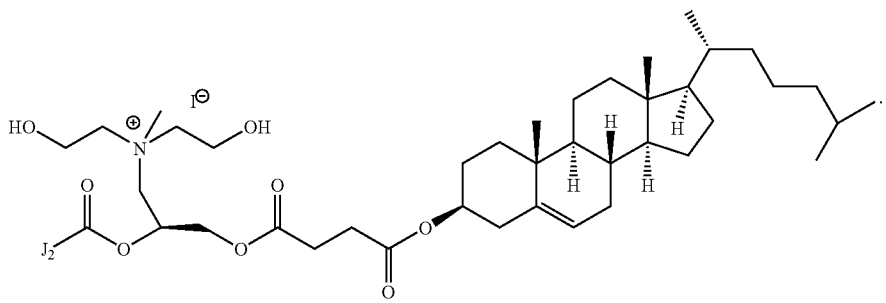

(20)

wherein $J_2$ is selected from the group consisting of aryl, substituted aryl, $C_{1-30}$-alkyl, substituted $C_{1-30}$-alkyl, $C_{1-30}$-alkenyl, substituted $C_{1-30}$-alkenyl, $C_{1-30}$-alkynyl, and substituted $C_{1-30}$-alkynyl.

In yet another embodiment, the present invention relates to a compound of the formula:

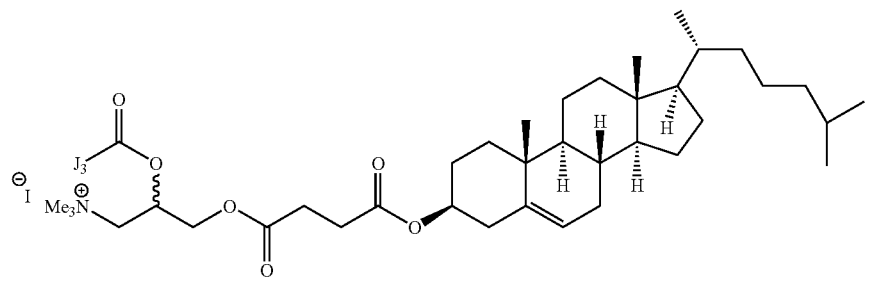

(40)

wherein $J_3$ is selected from the group consisting of aryl, substituted aryl, $C_{1-30}$-alkyl, substituted $C_{1-30}$-alkyl, $C_{1-30}$-alkenyl, substituted $C_{1-30}$-alkenyl, $C_{1-30}$-alkynyl, and substituted $C_{1-30}$-alkynyl.

In a particular embodiment, the invention is directed to a compound selected from the group consisting of the compounds 1-16:

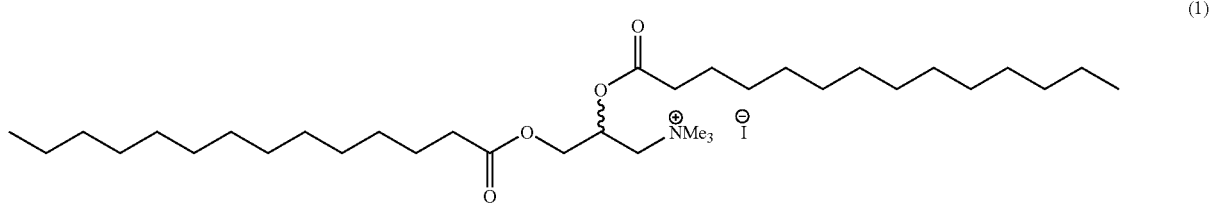

(1)

(2)

-continued
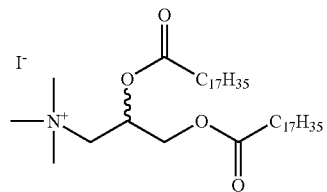
(3)
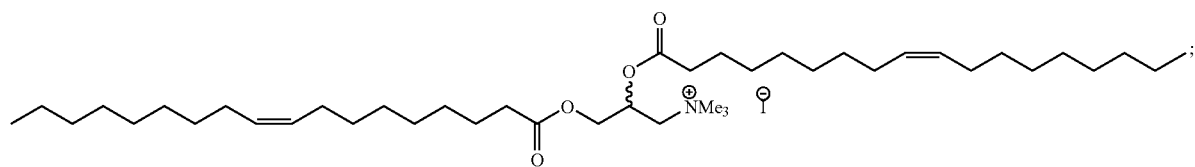
(4)
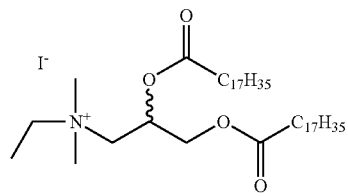
(5)
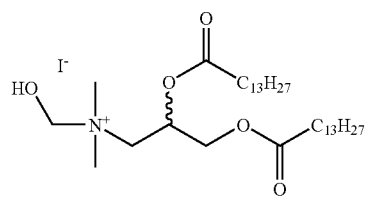
(6)
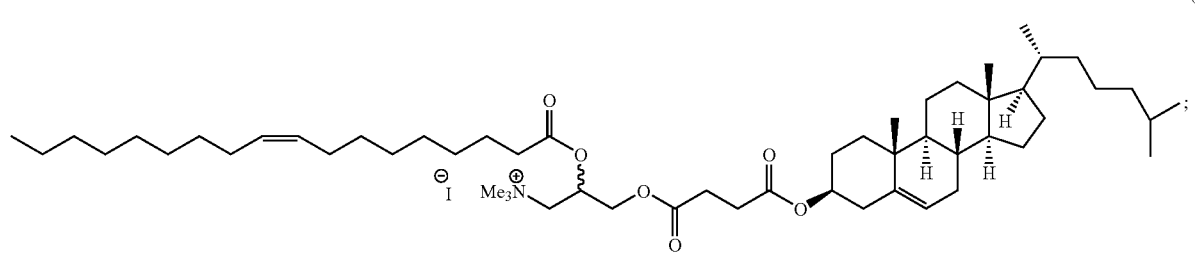
(7)
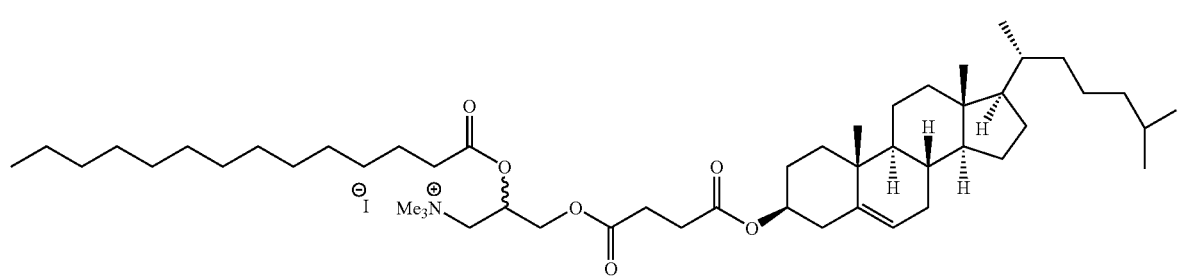
(8)
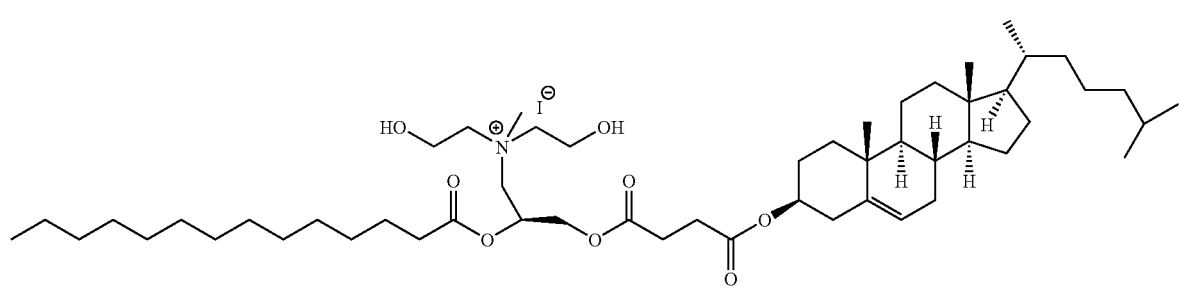
(9)

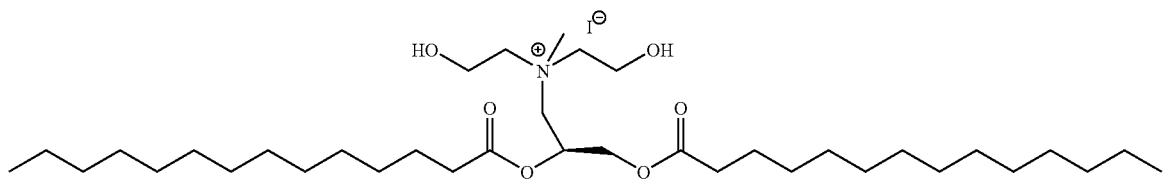
(10)
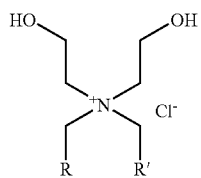
(11; R = R' = C₁₃H₂₇):
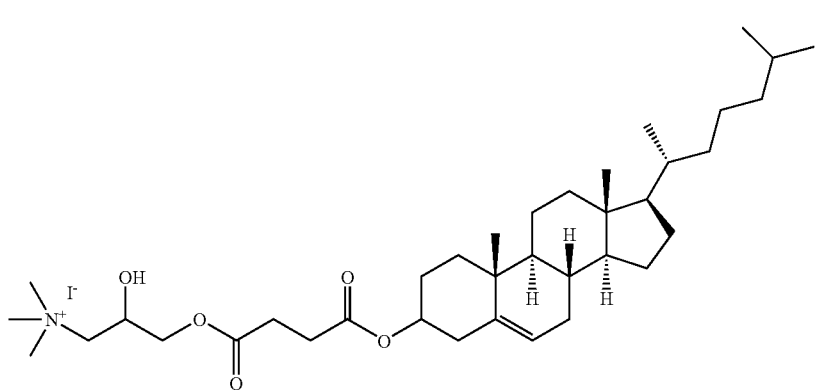
(12)
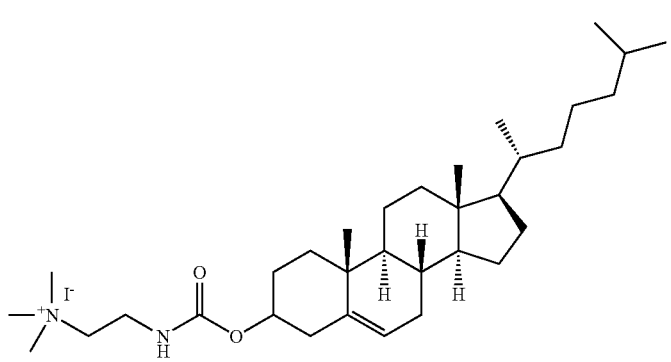
(13)
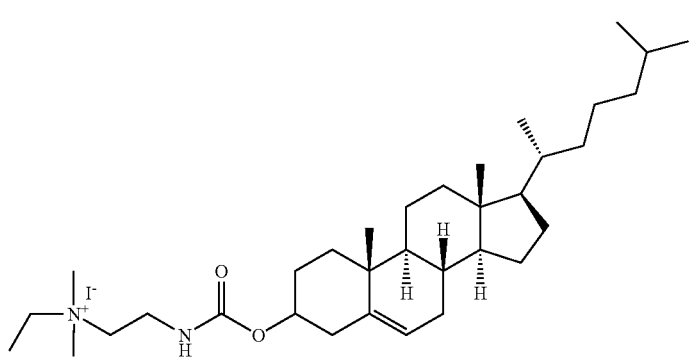
(14)

-continued

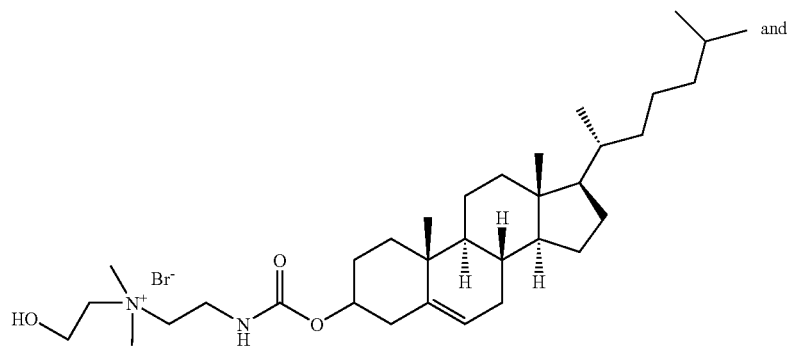

(15)

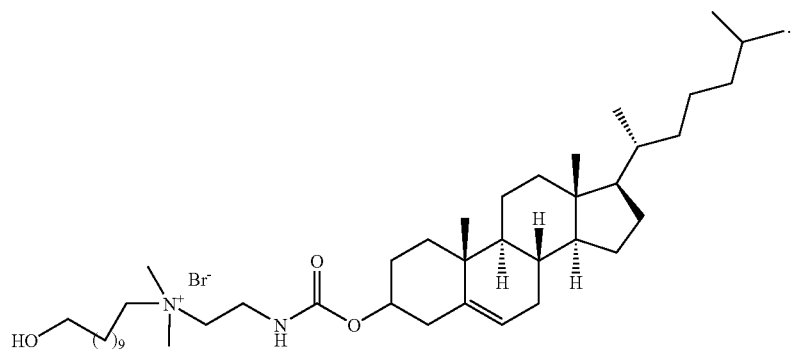

(16)

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. The term "alkyl" also includes alkenyl groups and alkynyl groups. Furthermore, the expression "$C_x$-$C_y$-alkyl", wherein x is 1-5 and y is 2-10 indicates a particular alkyl group (straight- or branched-chain) of a particular range of carbons. For example, the expression $C_1$-$C_4$-alkyl includes, but is not limited to, methyl, ethyl, propyl, butyl, isopropyl, tert-butyl and isobutyl. Moreover, the term $C_{3-6}$-cycloalkyl includes, but is not limited to, cyclopropyl, cyclopentyl, and cyclohexyl. As discussed below, these alkyl groups, as well as cycloalkyl groups, can be further substituted.

The term alkyl further includes alkyl groups which can further include oxygen, nitrogen, sulfur or phosphorous atoms replacing one or more carbons of the hydrocarbon backbone. In an embodiment, a straight chain or branched chain alkyl has 10 or fewer carbon atoms in its backbone (e.g., $C_1$-$C_{10}$ for straight chain, $C_3$-$C_{10}$ for branched chain), and more preferably 6 or fewer carbons. Likewise, preferred cycloalkyls have from 4-7 carbon atoms in their ring structure, and more preferably have 5 or 6 carbons in the ring structure.

Moreover, alkyl (e.g., methyl, ethyl, propyl, butyl, pentyl, hexyl, etc.) include both "unsubstituted alkyl" and "substituted alkyl", the latter of which refers to alkyl moieties having substituents replacing a hydrogen on one or more carbons of the hydrocarbon backbone, which allow the molecule to perform its intended function.

The term "substituted" is intended to describe moieties having substituents replacing a hydrogen on one or more atoms, e.g. C, O or N, of a molecule. Such substituents can include, for example, oxo, alkyl, alkoxy, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, morpholino, phenol, benzyl, phenyl, piperizine, cyclopentane, cyclohexane, pyridine, 5H-tetrazole, triazole, piperidine, or an aromatic or heteroaromatic moiety, and any combination thereof.

Further examples of substituents of the invention, which are not intended to be limiting, include moieties selected from straight or branched alkyl (preferably $C_1$-$C_5$), cycloalkyl (preferably $C_3$-$C_8$), alkoxy (preferably $C_1$-$C_6$), thioalkyl (preferably $C_1$-$C_6$), alkenyl (preferably $C_2$-$C_6$), alkynyl (preferably $C_2$-$C_6$), heterocyclic, carbocyclic, aryl (e.g., phenyl), aryloxy (e.g., phenoxy), aralkyl (e.g., benzyl), aryloxyalkyl (e.g., phenyloxyalkyl), arylacetamidoyl, alkylaryl, heteroaralkyl, alkylcarbonyl and arylcarbonyl or other such acyl group, heterocarbonyl, or heteroaryl group, $(CR'R'')_{0-3}NR'R''$ (e.g., $-NH_2$), $(CR'R'')_{0-3}CN$ (e.g., $-CN$), $-NO_2$, halogen (e.g., $-F$, $-Cl$, $-Br$, or $-I$), $(CR'R'')_{0-3}C(halogen)_3$ (e.g., $-CF_3$), $(CR'R'')_{0-3}CH(halogen)_2$, $(CR'R'')_{0-3}CH_2(halogen)$, $(CR'R'')_{0-3}CONR'R''$, $(CR'R'')_{0-3}(CNH)NR'R''$, $(CR'R'')_{0-3}S(O)_{1-2}NR'R''$, $(CR'R'')_{0-3}CHO$, $(CR'R'')_{0-3}O(CR'R'')_{0-3}H$, $(CR'R'')_{0-3}S(O)_{0-3}R'$ (e.g., $-SO_3H$, $-OSO_3H$), $(CR'R'')_{0-3}O(CR'R'')_{0-3}H$ (e.g., $-CH_2OCH_3$ and $-OCH_3$), $(CR'R'')_{0-3}S(CR'R'')_{0-3}H$ (e.g., $-SH$ and $-SCH_3$), $(CR'R'')_{0-3}OH$ (e.g., $-OH$), $(CR'R'')_{0-3}COR'$, $(CR'R'')_{0-3}$ (substituted or unsubstituted phenyl), (CR'R")$_{0-3}$(C$_3$-C$_8$ cycloalkyl), (CR'R")$_{0-3}$CO$_2$R' (e.g., —CO$_2$H), or (CR'R")$_{0-3}$OR' group, or the side chain of any naturally occurring amino acid; wherein R' and R" are each independently hydrogen, a C$_1$-C$_8$ alkyl, C$_2$-C$_5$ alkenyl, C$_2$-C$_5$ alkynyl, or aryl group. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, oxime, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety, and any combination thereof. In certain embodiments, a carbonyl moiety (C═O) can be further derivatized with an oxime moiety, e.g., an aldehyde moiety can be derivatized as its oxime (—C═N—OH) analog. It will be understood by those skilled in the art that the moieties substituted on the hydrocarbon chain can themselves be substituted, if appropriate. Cycloalkyls can be further substituted, e.g., with the substituents described above. An "aralkyl" moiety is an alkyl substituted with an aryl (e.g., phenylmethyl (i.e., benzyl)).

The term "alkenyl" includes unsaturated aliphatic groups analogous in length and possible substitution to the alkyls described above, but which contain at least one double bond.

For example, the term "alkenyl" includes straight-chain alkenyl groups (e.g., ethenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term alkenyl further includes alkenyl groups that include oxygen, nitrogen, sulfur or phosphorous atoms replacing one or more carbons of the hydrocarbon backbone. In certain embodiments, a straight chain or branched chain alkenyl group has 6 or fewer carbon atoms in its backbone (e.g., C$_2$-C$_6$ for straight chain, C$_3$-C$_6$ for branched chain). Likewise, cycloalkenyl groups can have from 3-8 carbon atoms in their ring structure, and more preferably have 5 or 6 carbons in the ring structure. The term C$_2$-C$_6$ includes alkenyl groups containing 2 to 6 carbon atoms.

Moreover, the term alkenyl includes both "unsubstituted alkenyls" and "substituted alkenyls", the latter of which refers to alkenyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl" includes unsaturated aliphatic groups analogous in length and possible substitution to the alkyls described above, but which contain at least one triple bond.

For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl further includes alkynyl groups that include oxygen, nitrogen, sulfur or phosphorous atoms replacing one or more carbons of the hydrocarbon backbone. In certain embodiments, a straight chain or branched chain alkynyl group has 6 or fewer carbon atoms in its backbone (e.g., C$_2$-C$_6$ for straight chain, C$_3$-C$_6$ for branched chain). The term C$_2$-C$_6$ includes alkynyl groups containing 2 to 6 carbon atoms.

Moreover, the term alkynyl includes both "unsubstituted alkynyls" and "substituted alkynyls", the latter of which refers to alkynyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

In a particular embodiment, the term "substituted" is intended to describe moieties having a cholesterol substituent replacing a hydrogen on one or more atoms, e.g. C, O or N, of a molecule. In one embodiment, the cholesterol substituent is represented below (cholesteryloxy):

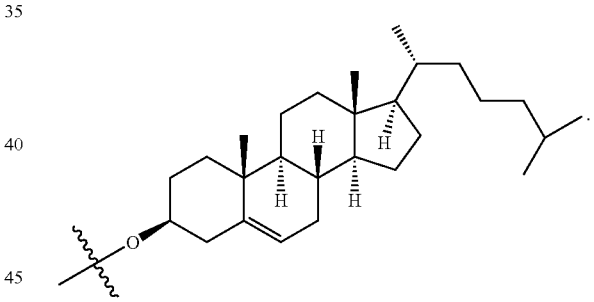

As such, in one embodiment, the terms "substituted C$_{1-30}$-alkyl group" and "substituted aryl group" refers to a C$_{1-30}$-alkyl group or aryl group that is substituted by a cholesteryloxy group, e.g., a cholesteryloxy succinate group, wherein the oxygen of the oxy group is the oxygen of the succinate group.

The term "amine" or "amino" should be understood as being broadly applied to both a molecule, or a moiety or functional group, as generally understood in the art, and can be primary, secondary, or tertiary. The term "amine" or "amino" includes compounds where a nitrogen atom is covalently bonded to at least one carbon or heteroatom. The terms include, for example, but are not limited to, "alkyl amino," "arylamino," "diarylamino," "alkylarylamino," "alkylaminoaryl," "arylaminoalkyl," "alkaminoalkyl," "amide," "amido," and "aminocarbonyl." The term "alkyl amino" comprises groups and compounds wherein the nitrogen is bound to at least one additional alkyl group. The term "dialkyl amino" includes groups wherein the nitrogen atom is bound to at least two additional alkyl groups. The term "arylamino" and "diarylamino" include groups wherein the nitrogen is bound to at least one or two aryl groups, respectively. The term "alkylarylamino," "alkylaminoaryl" or "arylaminoalkyl" refers to an amino group which is bound to at least one alkyl group and at least one aryl group. The term "alkaminoalkyl" refers to an alkyl, alkenyl, or alkynyl group bound to a nitrogen atom which is also bound to an alkyl group.

The term "amide," "amido" or "aminocarbonyl" includes compounds or moieties which contain a nitrogen atom which is bound to the carbon of a carbonyl or a thiocarbonyl group. The term includes "alkaminocarbonyl" or "alkylaminocarbonyl" groups which include alkyl, alkenyl, aryl or alkynyl groups bound to an amino group bound to a carbonyl group. It includes arylaminocarbonyl and arylcarbonylamino groups which include aryl or heteroaryl moieties bound to an amino group which is bound to the carbon of a carbonyl or thiocarbonyl group. The terms "alkylaminocarbonyl," "alkenylaminocarbonyl," "alkynylaminocarbonyl," "arylaminocarbonyl," "alkylcarbonylamino," "alkenylcarbonylamino," "alkynylcarbonylamino," and "arylcarbonylamino" are included in term "amide." Amides also include urea groups (aminocarbonylamino) and carbamates (oxycarbonylamino).

The term "aryl" includes groups, including 5- and 6-membered single-ring aromatic groups that can include from zero to four heteroatoms, for example, phenyl, pyrrole, furan, thiophene, thiazole, isothiaozole, imidazole, triazole, tetrazole, pyrazole, oxazole, isoxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, anthryl, phenanthryl, napthridine, indole, benzofuran, purine, benzofuran, deazapurine, or indolizine. Those aryl groups having heteroatoms in the ring structure can also be referred to as "aryl heterocycles", "heterocycles," "heteroaryls" or "heteroaromatics." The aromatic ring can be substituted at one or more ring positions with such substituents as described above, as for example, alkyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminoacarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The terms "heterocyclyl" or "heterocyclic group" refer to 3- to 10-membered ring structures, more preferably 4- to 7-membered rings, which ring structures include one or more heteroatoms, e.g., two, three, or four. Heterocyclyl groups include pyrrolidine, oxolane, thiolane, piperidine, piperazine, morpholine, lactones, lactams such as azetidinones and pyrrolidinones, sultams, sultones, and the like. The heterocyclic ring can be substituted at one or more positions with such substituents as described above, including halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety.

The terms "polycyclyl" or "polycyclic group" refer to two or more cyclic rings (e.g., cycloalkyls, cycloalkenyls, cycloalkynyls, aryls and/or heterocyclyls) where two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety.

The term "heteroatom" as used herein means an atom of any element other than carbon or hydrogen. Preferred heteroatoms are nitrogen, oxygen, sulfur and phosphorus.

It will be noted that the structure of some of the compounds of this invention includes asymmetric carbon atoms. It is to be understood accordingly that the isomers arising from such asymmetry (e.g., all enantiomers and diastereomers) are included within the scope of this invention unless indicated otherwise. Such isomers can be obtained in substantially pure form by classical separation techniques and by stereochemically controlled synthesis. That is, unless otherwise stipulated, any chiral carbon center can be of either (R)- or (S)-stereochemistry. Furthermore, alkenes can include either the E- or Z-geometry, where appropriate. Additionally, one skilled in the art will appreciate that the chemical structures as drawn can represent a number of possible tautomers, and the present invention also includes those tautomers.

In another embodiment, the invention includes any novel compound, salt thereof, e.g., pharmaceutically acceptable salt thereof, or pharmaceutical compositions containing compounds of the invention described herein, as well as any novel method of preparation or isolation of the compounds of the present invention. For example, compounds, lipid dispersions, and pharmaceutical compositions containing compounds of the formulae described set forth herein, as well as specific embodiments thereof, are considered part of this invention, including salts thereof, e.g., pharmaceutically acceptable salts.

B. Compound Synthesis

In one aspect, the invention is directed toward a method of preparing a compound having an ammonium salt moiety comprising the steps of:
  a) preparing a reaction mixture comprising (i) an amine and (ii) a substrate containing a leaving group; and
  b) exposing said reaction mixture to microwave energy from a microwave source, such that a compound having an ammonium salt moiety is produced.

In one embodiment of the invention, the ammonium salt moiety is a quaternary ammonium salt moiety. In another embodiment, the amine is a tertiary amine. In yet another embodiment, the substrate containing a leaving group is of the formula $C_{1-10}$-alkyl-X, wherein $C_{1-10}$-alkyl may be substituted with an OH group, and X is a leaving group. In still another embodiment, the substrate containing a leaving group is of the formula $C_{1-20}$-alkyl-X, wherein Cal 20-alkyl may be substituted with an OH group, and X is a leaving group. In another embodiment, the formula $C_{1-10}$-alkyl-X is selected from the group consisting of $CH_3$—X, $CH_3CH_2$—X, $CH_3CH_2$—X, HO—$(CH_2)_n$X and CH=CH—X, wherein n is 1-12. In a further embodiment, n is 2, 9, 10 or 11.

In another embodiment, X is bromo, chloro, iodo, —OC(=O)R, —OCO$_2$R, —OPO(OR)$_2$, —OSOR, —OSO$_2$R, —OR, —OR$_2^+$, —SR$_2^+$, —SO$_2$R, —NR$_3^+$, —PR$_3^+$, —NO$_2$, or —CN, wherein R is hydrogen, $C_{1-10}$-alkyl, aryl, or heteroaryl.

In another embodiment, the substrate of the formula $C_{11-20}$-alkyl-X is $Br(CH_2)_{13}CH_3$. In yet another embodiment, the substrate of the formula $C_{1-10}$-alkyl-X is $CH_3I$, $CH_3CH_2I$, $BrCH_2CH_2OH$, $ClCH_2CH_2OH$, or $Br(CH_2)_{11}OH$.

In another embodiment, the tertiary amine is of the formula N(Z)$_3$, wherein each Z is, independently of one another, a substituted or unsubstituted $C_{1-30}$-alkyl, or a substituted or unsubstituted aryl.

In a particular aspect, N(Z)$_3$ is represented by the Formula IA:

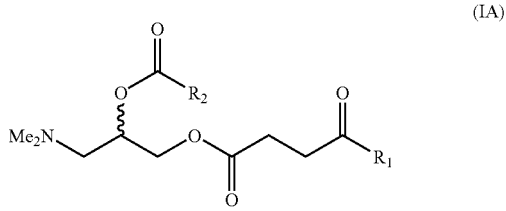

(IA)

wherein $R_1$ and $R_2$ are each, independently, selected from the group consisting of cholesteryloxy, aryl, substituted aryl, $C_{1-30}$-alkyl, substituted $C_{1-30}$-alkyl, $C_{1-30}$-alkenyl, substituted $C_{1-30}$-alkenyl, $C_{1-30}$-alkynyl, and substituted $C_{1-30}$-alkynyl. In a particular embodiment, $R_1$ is cholesteryloxy, and $R_2$ is $CH_2(CH_2)_6CH=CH(CH_2)_7CH_3$, $CH_2(CH_2)_{11}CH_3$, $CH_2(CH_2)_{13}CH_3$, $CH_2(CH_2)_{15}CH_3$ or $CH_2(CH_2)_{11}CH_3$.

In another aspect, N(Z)$_3$ is represented by the Formula IIA:

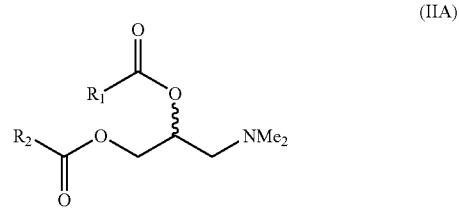

(IIA)

wherein $R_1$ and $R_2$ are each, independently, selected from the group consisting of cholesteryloxy, aryl, substituted aryl, $C_{1-30}$-alkyl, substituted $C_{1-30}$-alkyl, $C_{1-30}$-alkenyl, substituted $C_{1-30}$-alkenyl, $C_{1-30}$-alkynyl, and substituted $C_{1-30}$-alkynyl. In a particular embodiment, $R_1$ and $R_2$ are each, independently, $CH_2(CH_2)_6CH=CH(CH_2)_7CH_3$, $CH_2(CH_2)_{11}CH_3$, $CH_2(CH_2)_{13}CH_3$, $CH_2(CH_2)_{15}CH_3$ or $CH_2(CH_2)_{11}CH_3$.

In still another aspect, N(Z)$_3$ is represented by the Formula IIIA:

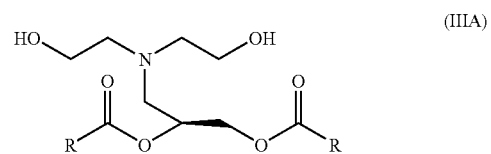

(IIIA)

wherein R is selected from the group consisting of cholesteryloxy, aryl, substituted aryl, $C_{1-30}$-alkyl, substituted $C_{1-30}$-alkyl, $C_{1-30}$-alkenyl, substituted $C_{1-30}$-alkenyl, $C_{1-30}$-alkynyl, and substituted $C_{1-30}$-alkynyl. In a particular embodiment, R is $CH_2(CH_2)_6CH=CH(CH_2)_7CH_3$, $CH_2(CH_2)_{11}CH_3$, $CH_2(CH_2)_{13}CH_3$, $CH_2(CH_2)_{15}CH_3$ or $CH_2(CH_2)_{11}CH_3$.

In yet another aspect, N(Z)$_3$ is represented by the Formula IVA:

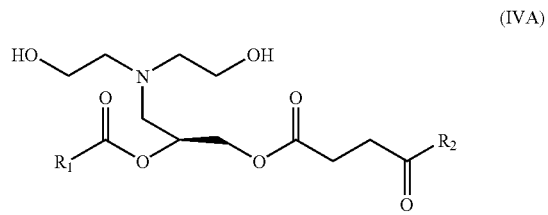

(IVA)

wherein $R_1$ and $R_2$ are each, independently, selected from the group consisting of cholesteryloxy, aryl, substituted aryl, $C_{1-30}$-alkyl, substituted $C_{1-30}$-alkyl, $C_{1-30}$-alkenyl, substituted $C_{1-30}$-alkenyl, $C_{1-30}$-alkynyl, and substituted $C_{1-30}$-alkynyl. In a particular embodiment, $R_1$ is $CH_2(CH_2)_6CH=CH(CH_2)_7CH_3$, $CH_2(CH_2)_{11}CH_3$, $CH_2(CH_2)_{13}CH_3$, $CH_2(CH_2)_{15}CH_3$ or $CH_2(CH_2)_{11}CH_3$. and $R_2$ is cholesteryloxy.

In one aspect, the compound having an ammonium salt moiety is represented by the Formula VA:

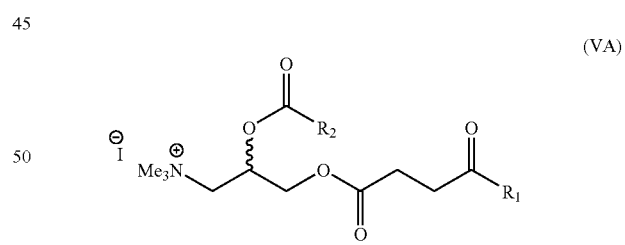

(VA)

wherein $R_1$ and $R_2$ are each, independently, selected from the group consisting of cholesteryloxy, aryl, substituted aryl, $C_{1-30}$-alkyl, substituted $C_{1-30}$-alkyl, $C_{1-30}$-alkenyl, substituted $C_{1-30}$-alkenyl, $C_{1-30}$-alkynyl, and substituted $C_{1-30}$-alkynyl. In a particular embodiment, $R_1$ is cholesteryloxy, and $R_2$ is $CH_2(CH_2)_6CH=CH(CH_2)_7CH_3$, $CH_2(CH_2)_{11}CH_3$, $CH_2(CH_2)_{13}CH_3$, $CH_2(CH_2)_{15}CH_3$ or $CH_2(CH_2)_{11}CH_3$.

In a particular embodiment of Formula VA, $R_1$ is cholesteryloxy, and $R_2$ is $CH_2(CH_2)_6CH=CH(CH_2)_7CH_3$ or $CH_2(CH_2)_{11}CH_3$, e.g.,

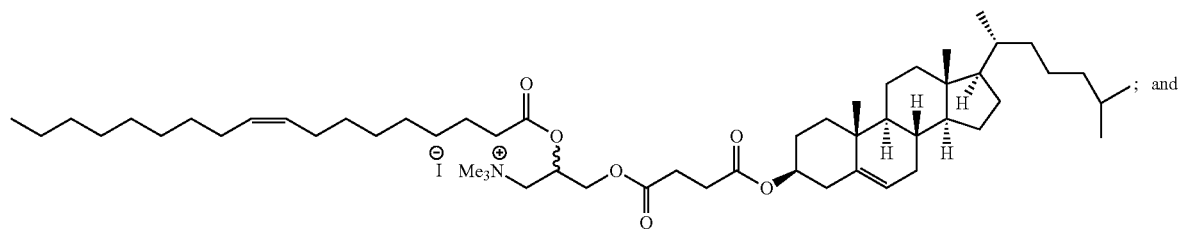

(7); and

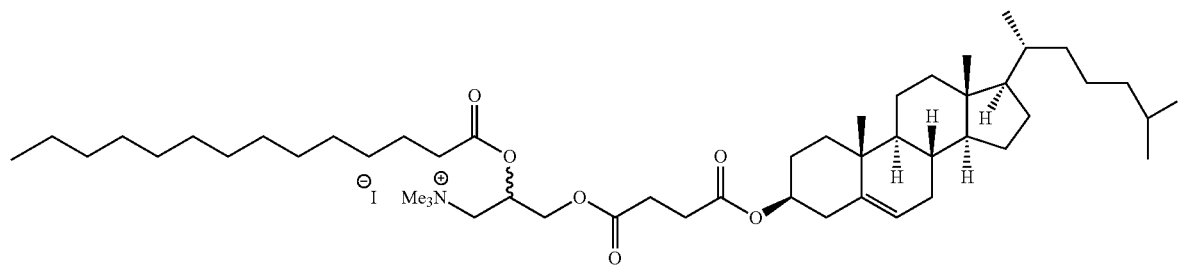

(8)

In yet another aspect, the compound having an ammonium salt moiety is represented by the Formula VIA, IXA or XA:

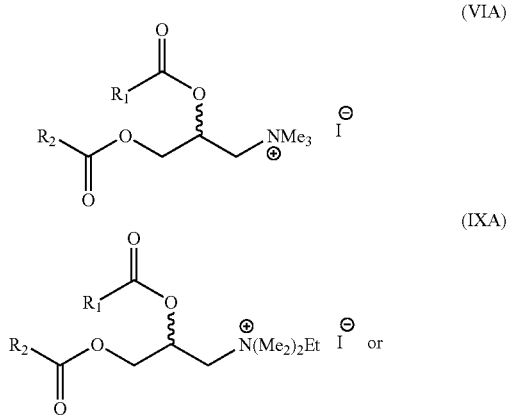

wherein $R_1$ and $R_2$ are each, independently, selected from the group consisting of cholesteryloxy, aryl, substituted aryl, $C_{1-30}$-alkyl, substituted $C_{1-30}$-alkyl, $C_{1-30}$-alkenyl, substituted $C_{1-30}$-alkenyl, $C_{1-30}$-alkynyl, and substituted $C_{1-30}$-alkynyl. In particular embodiments, $R_1$ and $R_2$ are each, independently, $CH_2(CH_2)_6CH=CH(CH_2)_7CH_3$, $CH_2(CH_2)_{11}CH_3$, $CH_2(CH_2)_{13}CH_3$, $CH_2(CH_2)_{15}CH_3$ or $CH_2(CH_2)_{11}CH_3$.

Particular embodiments of formula VIA are as follows:

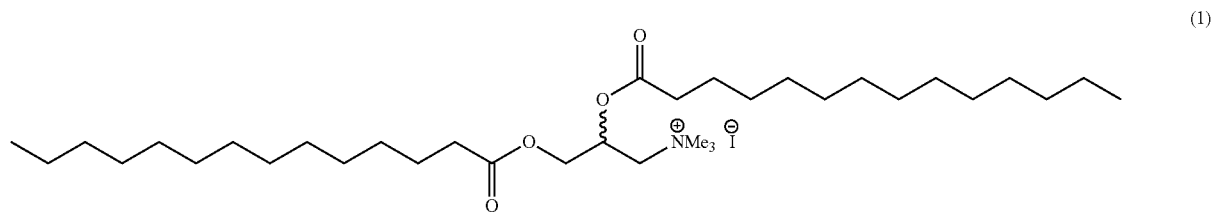

(1)

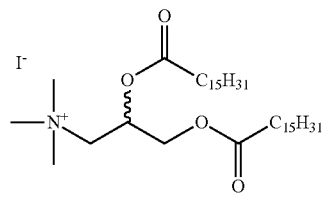

(2)

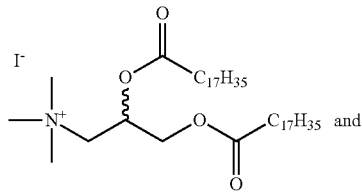
(3)

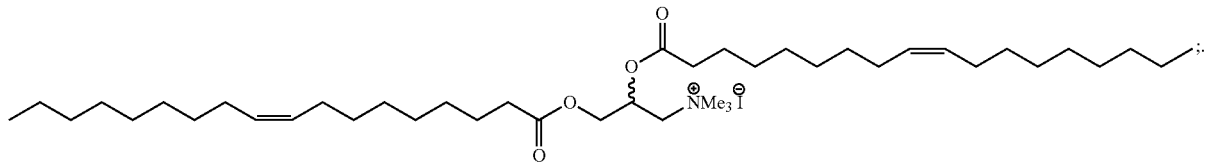
(4)

A particular embodiment of Formula IXA is as follows:

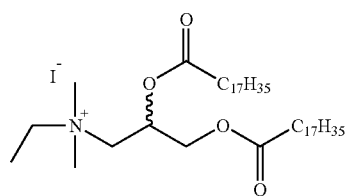
(5)

A particular embodiment of Formula XA is as follows:

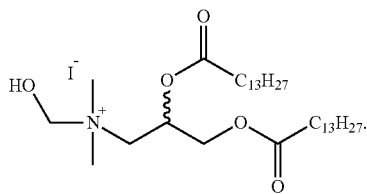
(6)

In yet another aspect, the compound having an ammonium salt moiety is represented by the Formula VIIA:

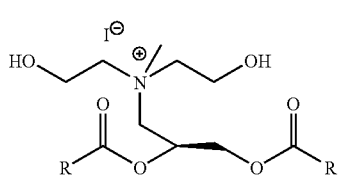
(VIIA)

wherein R is selected from the group consisting of cholesteryloxy, aryl, substituted aryl, $C_{1-30}$-alkyl, substituted $C_{1-30}$-alkyl, $C_{1-30}$-alkenyl, substituted $C_{1-30}$-alkenyl, $C_{1-30}$-alkynyl, and substituted $C_{1-30}$-alkynyl. In a particular embodiment, R is $CH_2(CH_2)_6CH=CH(CH_2)_7CH_3$, $CH_2(CH_2)_{11}CH_3$, $CH_2(CH_2)_{13}CH_3$, $CH_2(CH_2)_{15}CH_3$ or $CH_2(CH_2)_{11}CH_3$.

In a particular embodiment of Formula VIIA, R is $CH_2(CH_2)_{11}CH_3$, e.g.,

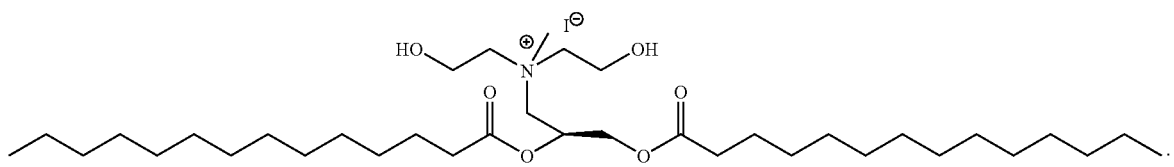
(10)

In yet another aspect, the compound having an ammonium salt moiety is represented by the Formula VIIIA:

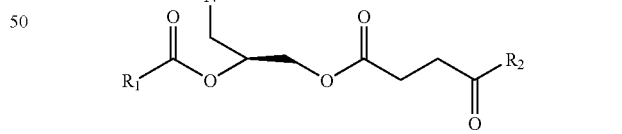
(VIIIA)

wherein $R_1$ and $R_2$ are each, independently, selected from the group consisting of cholesteryloxy, aryl, substituted aryl, $C_{1-30}$-alkyl, substituted $C_{1-30}$-alkyl, $C_{1-30}$-alkenyl, substituted $C_{1-30}$-alkenyl, $C_{1-30}$-alkynyl, and substituted $C_{1-30}$-alkynyl. In a particular embodiment, $R_1$ is $CH_2(CH_2)_6CH=CH(CH_2)_7CH_3$, $CH_2(CH_2)_{11}CH_3$, $CH_2(CH_2)_{13}CH_3$, $CH_2(CH_2)_{15}CH_3$ or $CH_2(CH_2)_{11}CH_3$ and $R_2$ is cholesteryloxy.

In a particular embodiment of Formula VIIIA, $R_1$ is $CH_2(CH_2)_{11}CH_3$ and $R_2$ is cholesteryloxy, e.g., (9)

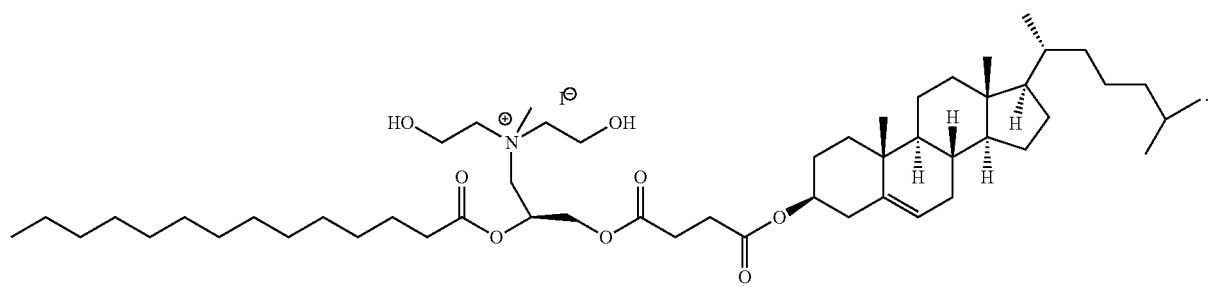

In yet another aspect, N(Z)₃ is represented by the Formula XIA:

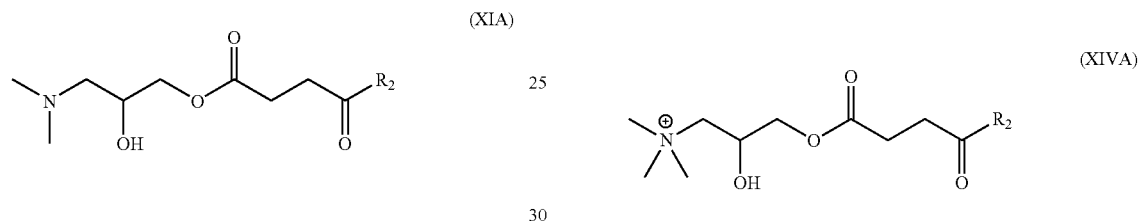

wherein $R_2$ is cholesteryloxy.

In yet another aspect, N(Z)₃ is represented by the Formula XIIA:

(XIIA)

wherein $R_2$ is cholesteryloxy.

In one aspect of the invention, the compound having an ammonium salt moiety produced by the methods of the invention is XIIIA:

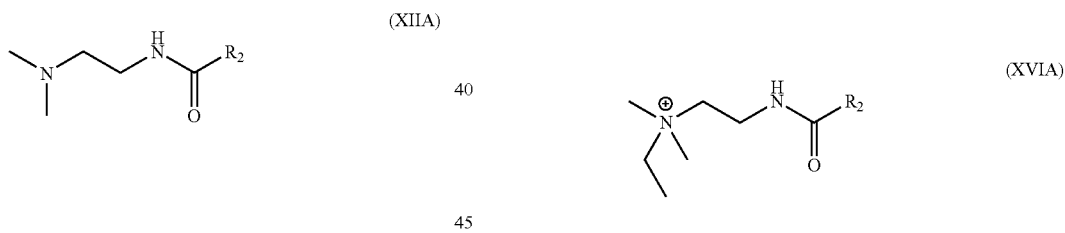

wherein R and R' are $C_{1-30}$-alkyl. In a particular embodiment, R and R' are $C_{1-20}$-alkyl. In another embodiment, R and R' are $(CH_2)_{10-15}CH_3$. In another embodiment, R and R' are $(CH_2)_{13}CH_3$.

In another embodiment, the compound having an ammonium salt moiety is XIVA, XVA, XVIA, XVIIA or XVIIIA:

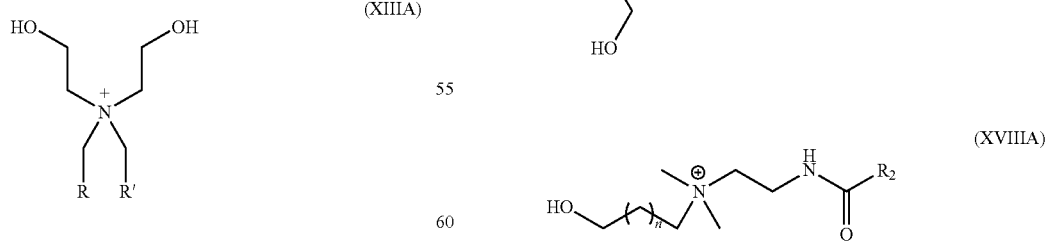

wherein $R_2$ is cholesteryloxy.

A preferred embodiment of Formula XIVA is as follows:

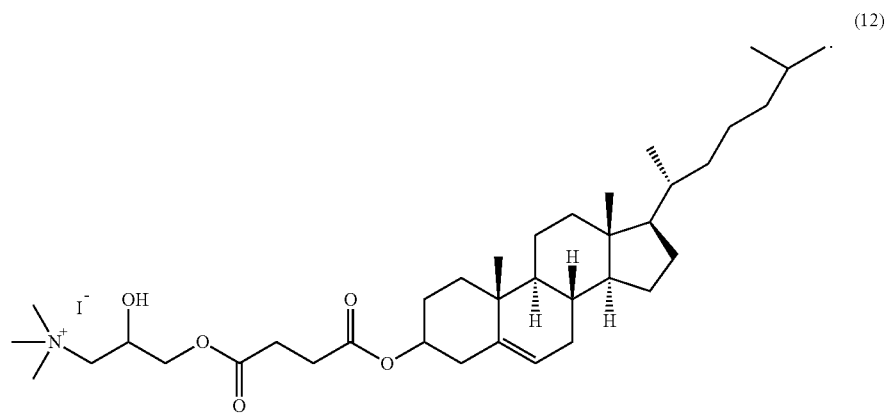
A preferred embodiment of Formula XVA is as follows:
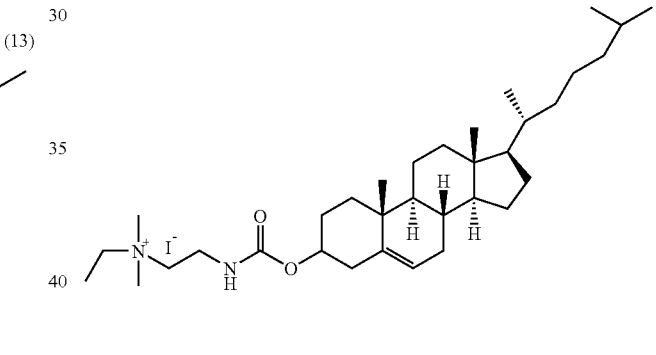
A preferred embodiment of Formula XVIA is as follows:
A preferred embodiment of Formula XVIIA is as follows:
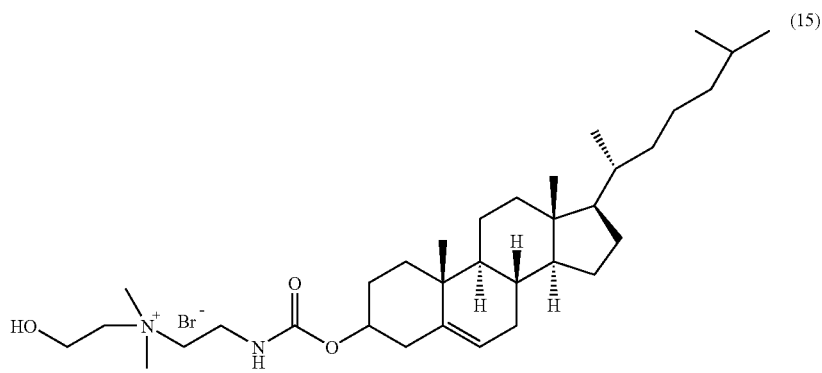

A preferred embodiment of Formula XVIIIA is as follows:

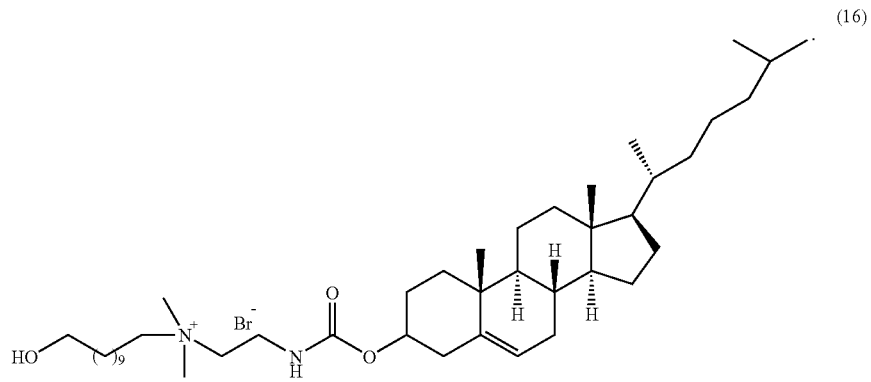

In another aspect, the synthesis methods of the invention can be used to prepare quaternary ammonium salts of the Formula II (DTDEAC, R=R'=C$_{13}$H$_{27}$):

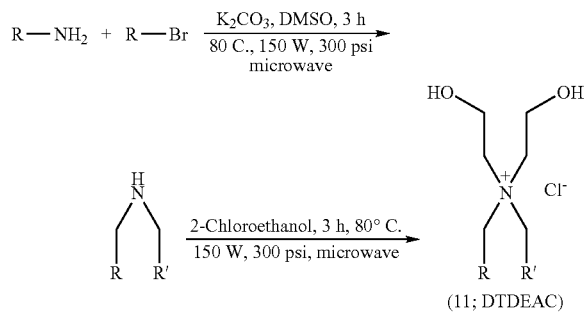

The present invention takes advantage of the benefits of microwave heating in the preparation of ammonium salts, particularly quaternary ammonium salts. In the present invention, the reaction mixture can be exposed to microwave energy, e.g., in a single-mode microwave cavity. In a particular embodiment, the use of a single-mode microwave cavity allows the placement of a reaction vessel in a fixed position of more uniform and more intense microwave irradiation than can be obtained in a multimode reactor. Examples of suitable microwave facilities are commercial ovens and cavities where a magnetron is used as a microwave source. The Microwell™ products from Labwell, Sweden are suitable for the present invention. Other alternatives include semiconductor microwave generators which can be used for combinatorial chemistry.

With respect to the frequency and power, the microwave energy applied according to the present invention typically has a frequency in the range of 300 MHz to 300 GHz, e.g., in the range of 900 MHz to 23 GHz, e.g., in the range of 1.5 GHz to 10.0 GHz and can be supplied to the reaction mixture at a power of 1-1000 W, e.g., 10-1000 W, e.g., 20-500 W (e.g., 150 W). The microwave energy can be supplied to the reaction mixture for a period of 1 second-24 hours, e.g., 1 hour-7 hours, e.g., 1 hour-4 hours (e.g., 150 W). The reaction can be conducted at a variety of pressures, e.g., atmospheric pressure, or 0-300 psi, or 100-500 psi, e.g., 150-350 psi, e.g., 200, 250, or 300 psi. Depending on the microwave source, its frequency and power, as well as the reaction components, exposure to microwave energy for less than one second can be sufficient to facilitate the reaction.

Without wishing to be bound by theory, microwave energy facilitates the reaction and heats the reaction system. In certain embodiments, the reaction producing the ammonium salt can be performed at low temperatures, such as below room temperature and as low as −100° C. The microwave energy in itself can provide the necessary energy input into the system to facilitate the reaction. The energy can be dissipated as heat yet may not be necessarily detectable or will be limited to a microenvironment within the reaction system.

In one aspect, the present invention provides a method for synthesizing ammonium salts by reacting an amine and a substrate containing a leaving group, and exposing said reaction mixture to microwave energy from a microwave source, e.g., a controllable microwave source. The amine can be a primary, secondary or tertiary amine. In certain embodiments where the amine is a primary or secondary amine, the ordinarily skilled artisan would understand that a corresponding number of equivalents of a substrate with a leaving group would be utilized in the preparation of a quaternary ammonium salt.

The methods according to the present invention are typically performed in solution, i.e., the amine and the substrate substituted by a leaving group are mixed in a solvent. Examples of suitable solvents are acetonitrile, DMF, DCM, DMSO, NMP, water, chloroform, MeOH, EtOH, benzonitrile, ethylene glycol, acetone, and THF, and any combination thereof. In one embodiment, a 1:1 mixture of chloroform and DMSO is used.

Synthesis schemes for the aforementioned compounds using the methods of the invention are demonstrated in the figures filed herewith. Detailed synthesis procedures using the methods of this invention are disclosed in the Exemplification section.

C. Use of the Compounds of the Invention for the Introduction of Therapeutic Agents into Cells Once synthesized, the compounds of the invention (e.g., compounds 1, 2, 3, 4, 5, 6, 7, 8, 9, 10, 11, 12, 13, 14, 15 and 16) can be used to formulate lipid dispersions such as liposomes, micelles, emulsions and lipoproteins by methods known to those of ordinary skill in the art. Accordingly, one embodiment of the invention is directed to a lipid composition comprising at least one compound of the invention. In another embodiment, the invention is a lipid composition comprising two or more lipids set forth in any of the above claims wherein the lipids are present in a molar ratio of about 1 to about 100 or any interval or range thereof.

When used to formulate liposomes, for example, the compounds of the invention can be used in combination with other cationic lipids, neutral phospholipids or negatively charged lipids to form liposomes. Suitable cationic lipid species which can be combined with the compounds of the invention include, but are not limited to, 1,2 bis(oleoyloxy)-3-(trimethylammonio)propane (DOTAP); N-[1,-(2,3-dioleoyloxy) propyl]-N,N,N-trimethyl ammonium chloride (DOTMA) or other N-(N,N-1-dialkoxy)-alkyl-N,N,N-trisubstituted ammonium surfactants; 1,2 dioleoyl-3-(4'-trimethylammonio) butanoyl-sn-glycerol (DOBT) or cholesterol (4'-trimethylammonia) butanoate (ChOTB) where the trimethylammonium group is connected via a butanoyl spacer arm to either the double chain (for DOTB) or cholesterol group (for ChOTB); DORI (DL-1,2-dioleoyl-3-dimethylaminopropyl-B-hydroxyethylammonium) or DORIE (DL-1,2-O-dioleoyl-3-dimethylaminopropyl-β-hydroxyethylammonium) (DORIE) or analogs thereof as disclosed in WO 93/03709; 1,2-dioleoyl-3-succinyl-sn-glycerol choline ester (DOSC); cholesterol hemisuccinate ester (ChOSC); lipopolyamines such as doctadecylamidoglycylspermine (DOGS) and dipalmitoyl phosphatidyesthanolamidospermine (DPPES), or the cationic lipids disclosed in U.S. Pat. No. 5,283,185, cholesterol-3β-carboxyamido-ethylenetrimethylammonium iodide, 1-dimethylamino-3-trimethylammonio-DL-2-propyl-cholesterol carboxylate iodide, cholesterol-3β-carboxyamidoethyleneamine, cholesterol-3β-oxysuccinamidoethylenetrimethylammonium iodide, 1-dimethylamino-3-trimethylammonio-DL-2-propyl-cholesterol-3β-oxysuccinate iodide, 2-[(2-trimethylammonio)-ethylmethylamino]ethyl-cholesterol-3β-oxysuccinate iodide, 3β[N—(N',N'-dimethylaminoethane)-carbamoyl]-cholesterol (DC-chol), and 3β-[N-(polyethyleneimine)-carbamoyl]cholesterol.

In specific embodiments of the invention, exemplary cationic lipids include cholesterol-3β-carboxyamidoethylenetrimethylanimonium iodide, 1-dimethylamino-3-trimethylammonio-DL-2-propyl-cholesterol carboxylate iodide, cholesterol-3β-carboxyamidoethyleneamine, cholesterol-3β-oxysuccin-amidoethylenetrimethylammonium iodide, 1-dimethylamino-3-trimethylammonio-DL-2-propyl-cholesterol-3β-oxysuccinate iodide, 2-[(2-trimethylammonio) ethylmethylamino]-ethyl-cholesterol-3β-oxysuccinate iodide, 3β[N—(N',N'dimethyl-aminoethane)-carbamoyl]-cholesterol (DC-chol), and 3β[N—(N',N'-dimethylaminoethane)-carbamoyl]-cholesterol.

In addition to cationic lipids, the liposomes can also contain other lipids. These lipids include, but are not limited to, lyso lipids of which lysophosphatidylcholine (1-oleoyllysophosphatidycholine) is an example, cholesterol, or neutral phospholipids including dioleoyl phosphatidyl ethanolamine (DOPE) or dioleoyl phosphatidylcholine (DOPC). The liposomes can also contain negatively charged lipids so long as the net charge of the complexes formed is positive. Negatively charged lipids of the invention are those comprising at least one lipid species having a net negative charge at or near physiological pH or combinations of these. Suitable negatively charged lipid species include, but are not limited to, phosphatidyl glycerol and phosphatidic acid or a similar phospholipid analog.

In certain embodiments where a compound of the invention is to be combined with another lipid to formulate liposomes, a preferred lipid is a neutral phospholipid, most preferably DOPE. In particular embodiments, mol/mol ratios of compound of the invention:DOPE can range from about 3:7 to about 7:3.

It is to be understood that in considering lipids which can be combined with the compounds of the invention to produce liposomes, those of ordinary skill in the art are not restricted only to the use of the lipids recited above but rather, any lipid composition can be used so long as a cationic liposome is produced.

Methods for producing such liposomes are known to those of ordinary skill in the art. A review of methodologies of liposome preparation can be found in Liposome Technology (CFC Press NY 1984); Liposomes by Ortro (Marcel Schher, 1987); Methods Biochem Anol. 33:337-462 (1988) and U.S. Pat. No. 5,283,185. Such methods include freeze-thaw extrusion and sonication. It is contemplated that both unilamellar liposomes (less than about 200 nm in average diameter) and multilamellar liposomes (greater than about 300 nm in average diameter) can be produced.

Once produced, the lipid dispersions of the invention can be mixed with biologically active substances to produce a biologically active substance:lipid complex.

In an alternative embodiment, lipid dispersions containing a compound of the invention can be mixed with polycation and a biologically active substance to form a lipid:polycation: biologically active substances complex. (Gao, X et al (1996) Biochemistry 35:1027-1036). Suitable polycations for use in forming such complexes are natural or synthetic amino acids, peptides, proteins, polyamines, carbohydrates and any synthetic cationic polymers. Nonlimiting examples of polycations include polyarginine, polyornithine, protamines and polylysine, polybrene (hexadimethrine bromide), histone, cationic dendrimer, spermine, spermidine and synthetic polypeptides derived from SV40 large T antigen which has excess positive charges and represents a nuclear localization signal. In a specific embodiment, the polycation is poly-L-lysine (PLL).

By "biologically active substances" (also referred to herein as a "therapeutic agent") as used throughout the specification and claims is meant a molecule, compound, or composition, which, when present in an effective amount, reacts with and/or affects a tissue, living cell, and/or organism or traverses a biological space, e.g., a blood brain barrier, such that the therapeutic agent or payload can have its mode of action. It is understood that depending on the nature of the active substance, the active substance can either be active in a biological space, at the cell surface, in the cell, or have its activity, such as with DNA, RNA, protein, or peptide, after being introduced into the cell.

Examples of biologically active substances include, but are not limited to, nucleic acids such as DNA, cDNA, RNA (full length mRNA, ribozymes, antisense RNA, RNAi siRNA, miRNA, decoys), oligodeoxynucleotides (phosphodiesters, phosphothioates, phosphoramidites, and all other chemical modifications), oligonucleotide (phosphodiesters, etc.) or linear and closed circular plasmid DNA; carbohydrates; antibodies (and/or fragments thereof), proteins and peptides, including recombinant proteins such as for example cytokines (e.g., NGF, G-CSF, GM-CSF), enzymes, vaccines (e.g., HBsAg, gp120); vitamins, prostaglandins, drugs such as local anesthetics (e.g. procaine), antimalarial agents (e.g., chloroquine), compounds which need to cross the blood-brain barrier such as anti-parkinson agents (e.g., leva-DOPA), adrenergic receptor antagonists (e.g., propanolol), anti-neoplastic agents (e.g., doxorubicin), antihistamines, biogenic amines (e.g., dopamine), antidepressants (e.g., desipramine), anticholinergics (e.g., atropine), antiarrhythmics (e.g., quinidine), antiemetics (e.g., chloroprimamine) and analgesics (e.g., codeine, morphine) or small molecular weight drugs such as cisplatin which enhance transfection activity, or prolong the life time of DNA in and outside the cells.

When the biologically active substance is an antigenic protein or peptide, the complexes formed by mixing the protein or peptide with lipid dispersions containing compound(s) of the present invention can be utilized as vaccines or active immunotherapy.

In particular embodiments, the biologically active substances are negatively charged substances such as nucleic acids, negatively charged proteins and carbohydrates including polysaccharides, or negatively charged drugs.

The present invention therefore provides methods for delivering biologically active substances to cells. In one embodiment the method comprises:
(a) mixing a biologically active substance with a lipid dispersion containing at least one compound of the invention to form a biologically active substance:lipid complex; and (b) contacting the cells with the complexes.

In an alternative embodiment, the method comprises: (a) mixing a biologically active substance with lipid dispersions and a polycation to form a biologically active substance:lipid:polycation complex; and (b) contacting the cells with the complex.

It is contemplated that the methods of the invention can be used to deliver biologically active substances to cells in vitro or in vivo. Ex vivo approaches are also contemplated.

It is further understood that when the complexes of the invention are contacted with cells in vivo, the complexes can be used therapeutically and/or prophylactically depending on the biologically active substance contained in the complexes. The invention therefore provides for therapeutic and/or prophylactic formulations comprising the complexes of the invention where such formulations comprise the complexes in a physiologically compatible buffer such as, for example, phosphate buffered saline, isotonic saline or low ionic strength buffer such as 10% sucrose in $H_2O$ (pH 7.4-7.6) or in Hepes (pH 7-8, e.g., pH 7.4-7.6). The complexes can be administered as aerosols or as liquid solutions for intratumor, intravenous, intratracheal, intraperitoneal, and intramuscular administration. Those of ordinary skill in the art would readily understand that the actual amount of complex to be administered will depend upon the route of administration, the pharmaceutical properties of the individual treated, as well as the results desired.

The present invention also provides methods for transfecting nucleic acids into cells in vitro or in vivo. It is to be understood that when used to transfect cells in vivo the methods of transfection can be used for gene therapy. It is also contemplated that when used to formulate nucleic acid:lipid and nucleic acid:lipid polycation complexes useful for transfecting cells, the lipid dispersions can contain a compound of the invention, in particular, the following compounds:

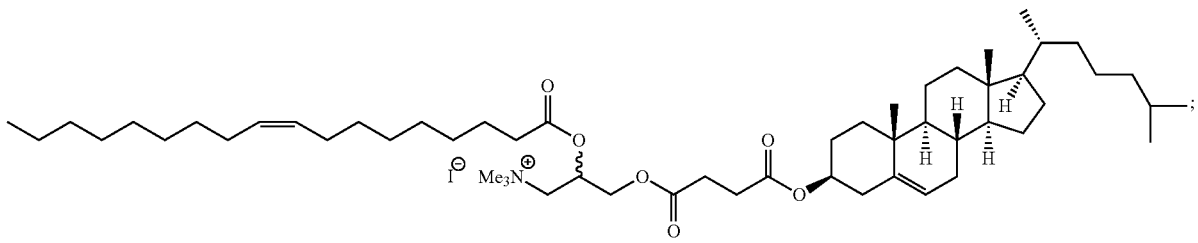

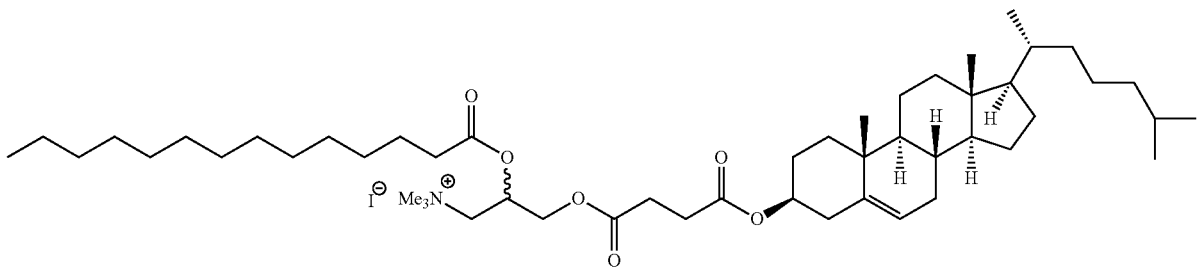

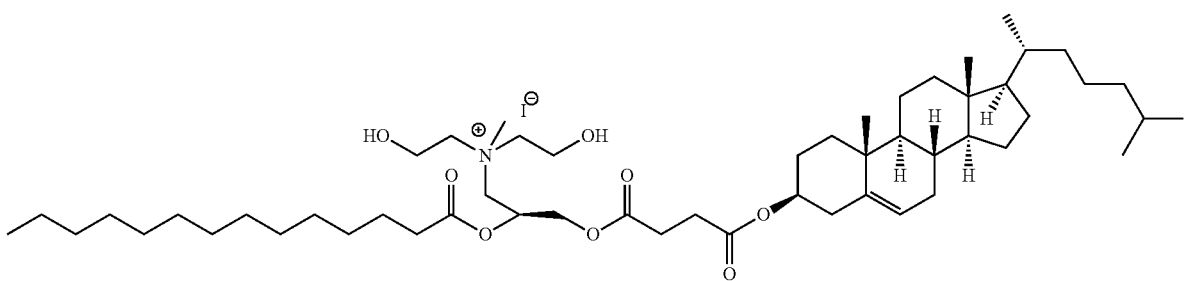

-continued
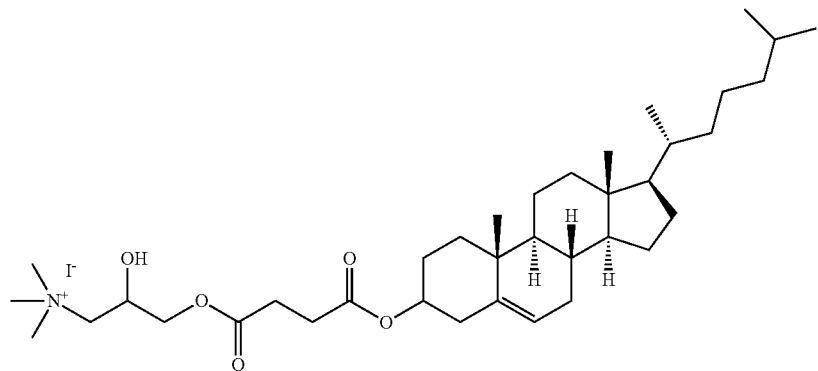
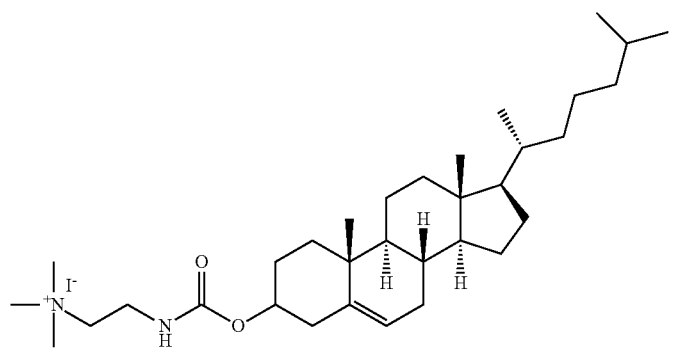
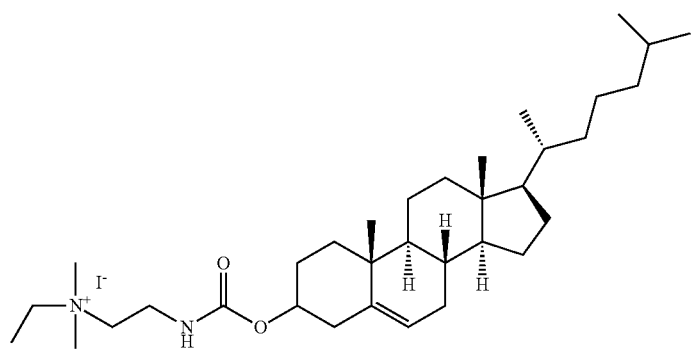
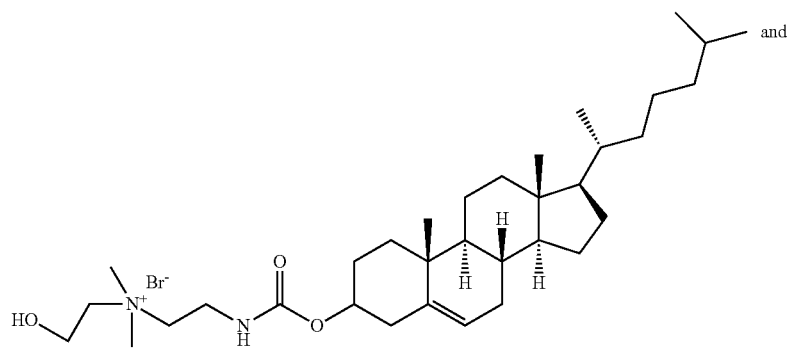

-continued

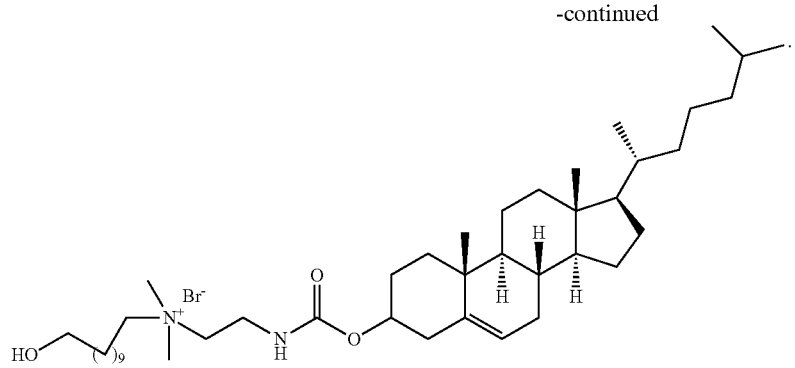

In addition, the lipids described above can individually be used as the lipid component in a nucleic acid:lipid and nucleic acid:lipid polycation complex, or can be used in combination with another lipid for enhanced activity.

For example, compound 7 (DC14) can be combined with 1,2-dioleoyl-L-α-glycero-3-phosphatidyl ethanolamine (DOPE) and/or 1,2-dioleoyl-L-α-glycero-3-phosphatidyl choline (DOPC), at ratios of about 9.0 to about 1.0, 3.0 to about 1.0, 1.0 to about 1.0, and 0.3 to about 1.0.

In addition, compound 8 (DC18) can be combined with 1,2-dioleoyl-L-α-glycero-3-phosphatidyl ethanolamine (DOPE) and/or 1,2-dioleoyl-L-α-glycero-3-phosphatidyl choline (DOPC), at ratios of about 9.0 to about 1.0, 3.0 to about 1.0, 1.0 to about 1.0, and 0.3 to about 1.0. Also, compound 9 (TC) can be combined with 1,2-dioleoyl-L-α-glycero-3-phosphatidyl ethanolamine (DOPE) and/or 1,2-dioleoyl-L-α-glycero-3-phosphatidyl choline (DOPC), at ratios of about 9.0 to about 1.0, 3.0 to about 1.0, 1.0 to about 1.0, and 0.3 to about 1.0.

Also, compound CC2 can be combined with 1,2-dioleoyl-L-α-glycero-3-phosphatidyl ethanolamine (DOPE) and/or 1,2-dioleoyl-L-α-glycero-3-phosphatidyl choline (DOPC), at ratios of about 9.0 to about 1.0, 3.0 to about 1.0, 1.0 to about 1.0, and 0.3 to about 1.0.

Also, compound CC3 can be combined with 1,2-dioleoyl-L-α-glycero-3-phosphatidyl ethanolamine (DOPE) and/or 1,2-dioleoyl-L-α-glycero-3-phosphatidyl choline (DOPC), at ratios of about 9.0 to about 1.0, 3.0 to about 1.0, 1.0 to about 1.0, and 0.3 to about 1.0.

2. Therapeutic Agents

The present invention features lipids which can be complexed with therapeutic agents, for example small molecules, nanoparticles, peptides, polypeptides, and in particular, nucleic acids, such as DNA, RNA, RNAi agents, and/or vectors (e.g., plasmids, viruses). The lipid/therapeutic agent complex in turn can be used as a therapeutic agent. In a particular embodiment, the complex comprises an RNAi agent, for example, "small interfering RNA molecules" ("siRNA molecules" or "siRNA" but also single and double stranded shRNAs) for modulating gene activity of a cell. Typically, an siRNA molecule is a duplex consisting of a sense strand and complementary antisense strand, the antisense strand having sufficient complementarity to a target mRNA to mediate RNAi, wherein the molecule is either administered as separate strands, either annealed or non-annealed strands.

siRNAs can be from about 10-60 or more nucleotides, i.e., each strand comprises 10-50 nucleotides (or nucleotide analogs). More preferably, the siRNA molecule has a length from about 15-45 nucleotides. Even more preferably, the siRNA molecule has a length from about 18-25 nucleotides, or ranges or intervals thereof, e.g., 5-18, 18-60 or 20-60. The siRNA molecules further have a sequence that is "sufficiently complementary" to a target mRNA sequence to direct target-specific RNA interference (RNAi), as defined herein, i.e., the siRNA has a sequence sufficient to trigger the destruction of the target mRNA by the RNAi machinery or process. In one embodiment, the siRNA agent is suitable for modulating CDK9 activity in a cell or tissue, either in vitro, ex vivo, or in vivo.

3. Producing Nucleic Acid Agents

Nucleic acid agents, e.g., RNAi agents, more particularly, siRNAs, can be produced enzymatically or by partial/total organic synthesis. In one embodiment, an RNAi agent is prepared chemically. Methods of synthesizing RNA molecules are known in the art, in particular, the chemical synthesis methods as de scribed in Verma and Eckstein (1998) *Annul Rev. Biochem.* 67:99-134. In another embodiment, the nucleic acids are produced enzymatically, e.g., by enzymatic transcription from synthetic DNA templates or from DNA plasmids isolated from recombinant bacteria. Typically, phage RNA polymerases are used such as T7, T3 or SP6 RNA polymerase (Milligan and Uhlenbeck (1989) *Methods Enzymol.* 180:51-62). In one embodiment, the siRNAs are synthesized either in vivo, in situ, or in vitro. Endogenous RNA polymerase of the cell can mediate transcription in vivo or in situ, or cloned RNA polymerase can be used for transcription in vivo or in vitro. For transcription from a transgene in vivo or an expression construct, a regulatory region (e.g., promoter, enhancer, silencer, splice donor and acceptor, polyadenylation) can be used to transcribe the siRNA. Inhibition can be targeted by specific transcription in an organ, tissue, or cell type; stimulation of an environmental condition (e.g., infection, stress, temperature, chemical inducers); and/or engineering transcription at a developmental stage or age or by conditional expression from a vector or transgene having an inducible promoter or operon. Any of the foregoing agents can be delivered to a cell target or biological space when complexed with a compound of the invention, e.g., one or more suitable lipids as described herein, typically as a lipid composition, lipid dispersion, and/or liposome.

4. Modified Nucleic Acid Agents

The invention features delivery of nucleic acids, e.g., small interfering RNAs (siRNAs) that include a sense strand and an antisense strand, wherein the antisense strand has a sequence sufficiently complementary to a target mRNA sequence to direct target-specific RNA interference (RNAi). It is understood that the nucleic acid agents of the invention can also be modified for example, the nucleic agent, e.g., RNAi agent, can be methylated, e.g., 2'O-methylated at one of more bases.

Certain modifications confer useful properties to siRNA. For example, increased stability compared to an unmodified siRNA or a label that can be used, e.g., to trace the siRNA, to purify an siRNA, or to purify the siRNA and cellular components with which it is associated. For example, such modifications can be used to stabilize the nucleic acid, improve RNAi responsiveness in a cell and/or improve its intracellular half-life. Certain modifications can also increase the uptake of the siRNA by a cell. For example, functional groups such as biotin are useful for affinity purification of proteins and molecular complexes involved in the RNAi mechanism.

siRNA modifications are designed such that properties important for in vivo applications, in particular, human therapeutic applications, are improved without compromising the RNAi activity of the siRNA molecules e.g., modifications to increase resistance of the siRNA molecules to nucleases. Modified siRNA molecules of the invention comprise a sense strand and an antisense strand, wherein the sense strand or antisense strand is modified by the substitution of at least one nucleotide with a modified nucleotide, such that, for example, in vivo stability is enhanced as compared to a corresponding unmodified siRNA, or such that the target efficiency is enhanced compared to a corresponding unmodified siRNA. Such modifications are also useful to improve uptake of the siRNA by a cell. Preferred modified nucleotides do not effect the ability of the antisense strand to adopt A-form helix conformation when base-pairing with the target mRNA sequence, e.g., an A-form helix conformation comprising a normal major groove when base-pairing with the target mRNA sequence.

Modified siRNA molecules of the invention (i.e., duplex siRNA molecules) can be modified at the 5' end, 3' end, 5' and 3' end, and/or at internal residues, or any combination thereof. Internal siRNA modifications can be, for example, sugar modifications, nucleobase modifications, backbone modifications, and can contain mismatches, bulges, or crosslinks. Also preferred are 3' end, 5' end, or 3' and 5' and/or internal modifications, wherein the modifications are, for example, cross linkers, heterofunctional cross linkers, dendrimer, nano-particle, peptides, organic compounds (e.g., fluorescent dyes), and/or photocleavable compounds.

5. Selecting a Gene Target

In one embodiment, the target gene sequence or mRNA of the invention encodes the amino acid sequence of a cellular protein, e.g., a protein involved in cell growth or suppression, e.g., a nuclear, cytoplasmic, transmembrane, membrane-associated protein, or cellular ligand. In another embodiment, the target mRNA of the invention specifies the amino acid sequence of an extracellular protein (e.g., an extracellular matrix protein or secreted protein). Typical classes of proteins are developmental proteins, cancer gene such as oncogenes, tumor suppressor genes, and enzymatic proteins, such as topoisomerases, kinases, and telomerases.

In a preferred aspect of the invention, the target mRNA molecule of the invention specifies the amino acid sequence of a protein associated with a pathological condition. By modulating the expression of the foregoing proteins, valuable information regarding the function of such proteins and therapeutic benefits which can be obtained from such modulation can be obtained. A target gene can be provided as a therapeutic agent, e.g., in nucleic acid form, e.g., in transcribed form either as a transcript or as an expressible gene, or as an RNAi agent using, for example, the lipid based delivery systems described herein. Alternatively, or in combination, a gene product in the form of a peptide or polypeptide can be provided using such delivery systems.

6. Determining Gene Target Sequence Identity

Where the target gene sequence is to be modulated via RNA interference (as opposed to providing in trans a vector, transcript, or gene product), sequence identity is typically considered because the target RNA cleavage reaction guided by siRNAs (e.g., by siRNAs) is highly sequence specific. In general, siRNA containing a nucleotide sequences identical to a portion of the target gene are preferred for inhibition. However, 100% sequence identity between the siRNA and the target gene is not required to practice the present invention. Thus the invention has the advantage of being able to tolerate sequence variations that might be expected due to genetic mutation, strain polymorphism, or evolutionary divergence. For example, siRNA sequences with insertions, deletions, and single point mutations relative to the target sequence have also been found to be effective for inhibition. Moreover, not all positions of a siRNA contribute equally to target recognition. Mismatches in the center of the siRNA are most critical and essentially abolish target RNA cleavage. Mismatches upstream of the center or upstream of the cleavage site referencing the antisense strand are tolerated but significantly reduce target RNA cleavage. Mismatches downstream of the center or cleavage site referencing the antisense strand, preferably located near the 3' end of the antisense strand, e.g. 1, 2, 3, 4, 5 or 6 nucleotides from the 3' end of the antisense strand, are tolerated and reduce target RNA cleavage only slightly.

Sequence identity can be determined by sequence comparison and alignment algorithms known in the art. To determine the percent identity of two nucleic acid sequences (or of two amino acid sequences), the sequences are aligned for optimal comparison purposes (e.g., gaps can be introduced in the first sequence or second sequence for optimal alignment). A preferred, non-limiting example of a local alignment algorithm utilized for the comparison of sequences is the algorithm of Karlin and Altschul (1990) *Proc. Natl. Acad. Sci. USA* 87:2264-68, modified as in Karlin and Altschul (1993) *Proc. Natl. Acad. Sci. USA* 90:5873-77. Such an algorithm is incorporated into the BLAST programs (version 2.0) of Altschul, et al. (1990) *J. Mol. Biol.* 215:403-10.

Greater than 90% sequence identity, e.g., 91%, 92%, 93%, 94%, 95%, 96%, 97%, 98%, 99% or even 100% sequence identity, between the siRNA and the portion of the target gene is preferred. Alternatively, the siRNA can be defined functionally as a nucleotide sequence (or oligonucleotide sequence) that is capable of hybridizing with a portion of the target gene transcript. Examples of stringency conditions for polynucleotide hybridization are provided in Sambrook, J., E. F. Fritsch, and T. Maniatis, 1989, *Molecular Cloning: A Laboratory Manual*, Cold Spring Harbor Laboratory Press, Cold Spring Harbor, N.Y., chapters 9 and 11, and *Current Protocols in Molecular Biology*, 1995, F. M. Ausubel et al., eds., John Wiley & Sons, Inc., sections 2.10 and 6.3-6.4, incorporated herein by reference.

7. Expression Vectors and Host Cells

Another aspect of the invention pertains to the transfer/delivery of vectors, preferably expression vectors, containing a nucleic acid encoding a gene product (or portion thereof) or RNAi agent. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses, adeno-associated viruses, and lentiviruses), which serve equivalent functions. Any of the foregoing vectors (including viral-based vectors) can be complexed with a delivery system of the invention, i.e., a lipid composition, lipid dispersion, or liposome as described herein, for efficient delivery to a cell, cellular or biological space, and/or organism.

8. Screening Assays

The methods of the invention are also suitable for use in methods to identify and/or characterize RNAi agents, pharmacological agents, e.g. identifying new RNAi agents, pharmacological agents from a collection of test substances and/or characterizing mechanisms of action and/or side effects of known RNAi agents or pharmacological agents.

Thus, the present invention also relates to a system, for example, a high throughput system (HTS), for identifying and/or characterizing pharmacological agents acting on at least one target protein comprising: a eukaryotic cell, cell extract, or a eukaryotic non-human organism primed or capable of being primed and expressing at least one endogenous target gene coding for a target protein, at least one RNAi agent molecule capable of enhancing RISC activity or RNA responsiveness and inhibiting the expression of at least one endogenous target gene, and a test substance or a collection of test substances wherein the properties of the test substance or collection of test substances are to be identified and/or characterized.

The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds can be presented in solution (e.g., Houghten (1992) *Biotechniques* 13:412-421), or on beads (Lam (1991) *Nature* 354:82-84), chips (Fodor (1993) Nature 364:555-556), bacteria (Ladner U.S. Pat. No. 5,223,409), spores (Ladner U.S. Pat. No. '409), plasmids (Cull et al. (1992) *Proc Natl Acad Sci USA* 89:1865-1869) or on phage (Scott and Smith (1990) *Science* 249:386-390); (Devlin (1990) *Science* 249:404-406); (Cwirla et al. (1990) *Proc. Natl. Acad. Sci.* 87:6378-6382); (Felici (1991) *J. Mol. Biol.* 222:301-310); (Ladner supra.)).

In a particular embodiment, the library is a natural product library, e.g., a library produced by a bacterial, fungal, or yeast culture. In another particular embodiment, the library is a synthetic compound library.

9. Transgenic Organisms

The lipid/nucleic acid complexes of the invention can be introduced into transgenic animals or cells that give rise to such organism (e.g., stem cells, zygotes, blastocysts, and the like). These animals represent a model system for the study of disorders that are caused by, or exacerbated by, overexpression or underexpression (as compared to wildtype or normal) of nucleic acids (and their encoded polypeptides) targeted for destruction by the RNAi agents, e.g., siRNAs and shRNAs, and for the development of therapeutic agents that modulate the expression or activity of nucleic acids or polypeptides targeted for destruction.

Transgenic animals can be farm animals (pigs, goats, sheep, cows, horses, rabbits, and the like), rodents (such as rats, guinea pigs, and mice), non-human primates (for example, baboons, monkeys, and chimpanzees), and domestic animals (for example, dogs and cats). Invertebrates such as *Caenorhabditis elegans* or *Drosophila* can be used as well as non-mammalian vertebrates such as fish (e.g., zebrafish) or birds (e.g., chickens).

10. Methods of Treatment

The present invention provides for both prophylactic and therapeutic methods of treating a subject at risk of (or susceptible to) a disorder or having a disorder associated with aberrant or unwanted target gene expression or activity. In one embodiment, the subject is administered a lipid/therapeutic agent complex, for example, a liposome comprising an siRNA for suppressing the expression of an the undesired gene product. It is understood that "treatment" or "treating" as used herein, is defined as the application or administration of a therapeutic agent (e.g., an RNAi agent or vector or transgene encoding same, a polypeptide, e.g., an antibody or fragment thereof, or small molecule) to a patient, or application or administration of a therapeutic agent to an isolated tissue or cell line from a patient, who has a disease or disorder, a symptom of disease or disorder or a predisposition toward a disease or disorder, with the purpose to cure, heal, alleviate, relieve, alter, remedy, ameliorate, improve or affect the disease or disorder, the symptoms of the disease or disorder, or the predisposition toward disease.

11. Prophylactic Methods

In another aspect, the invention provides a method for preventing in a subject, a disease or condition associated with an aberrant or unwanted target gene expression or activity, by administering to the subject a lipid/therapeutic agent complex of the invention (e.g., an RNAi agent or vector or transgene encoding same, a polypeptide, e.g., an antibody or fragment thereof, or small molecule). Subjects at risk for a disease which is caused or contributed to by aberrant or unwanted target gene expression or activity can be identified by, for example, any or a combination of diagnostic or prognostic assays as described herein. Administration of a prophylactic agent can occur prior to the manifestation of symptoms characteristic of the target gene aberrancy, such that a disease or disorder is prevented or, alternatively, delayed in its progression. Depending on the type of target gene aberrancy, for example, a target gene, target gene agonist or target gene antagonist agent can be used for treating the subject. The appropriate agent can be determined based on screening assays described herein.

12. Therapeutic Methods

In yet another aspect, the invention pertains to methods of modulating target gene expression, protein expression or activity for therapeutic purposes. Accordingly, in an exemplary embodiment, the modulatory method of the invention involves contacting a cell capable of expressing target gene with a lipid/therapeutic agent complex (e.g., an RNAi agent or vector or transgene encoding same) that is specific for the target gene or protein (e.g., is specific for the mRNA encoded by said gene or specifying the amino acid sequence of said protein) such that expression or one or more of the activities of target protein is modulated. These modulatory methods can be performed in vitro (e.g., by culturing the cell with the agent), in vivo (e.g., by administering the agent to a subject), or ex vivo. As such, the present invention provides methods of treating an individual afflicted with a disease or disorder characterized by aberrant or unwanted expression or activity of a target gene polypeptide or nucleic acid molecule. Inhibition of target gene activity is desirable in situations in which target gene is abnormally unregulated and/or in which decreased target gene activity is likely to have a beneficial effect.

13. Pharmacogenomics

The lipid/therapeutic agent complexes (e.g., an RNAi agent or vector or transgene encoding same) of the invention can be administered to individuals to treat (prophylactically or therapeutically) disorders associated with aberrant or unwanted target gene activity. In conjunction with such treatment, pharmacogenomics (i.e., the study of the relationship between an individual's genotype and that individual's response to a foreign compound or drug) can be considered. Differences in metabolism of therapeutics can lead to severe toxicity or therapeutic failure by altering the relation between dose and blood concentration of the pharmacologically active drug. Thus, a physician or clinician can consider applying knowledge obtained in relevant pharmacogenomics studies in determining whether to administer a therapeutic agent as well as tailoring the dosage and/or therapeutic regimen of treatment with a therapeutic agent.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23(10-11): 983-985 and Linder, M. W. et al. (1997) *Clin. Chem.* 43(2):254-266

14. Pharmaceutical Compositions

The invention pertains to uses of the above-described agents for therapeutic treatments as described infra. Accordingly, compositions of the present invention are suitable for use as pharmaceutical compositions, in particular, for drug delivery administration. Such compositions typically comprise a small molecule, peptide, polypeptide or protein, nanoparticle, and/or nucleic acid molecule, e.g., an expression vector, RNAi agent, e.g., an siRNA agent for carrying out gene silencing, and a pharmaceutically acceptable carrier. In one embodiment, the protein is an antibody or fragment thereof, e.g., Fab, Fab', F(ab')$_2$, Fv, scFv, Fd or Dab fragments. As used herein the language "pharmaceutically acceptable carrier" is intended to include any and all solvents, dispersion media, coatings, antibacterial and antifungal agents, isotonic and absorption delaying agents, and the like, compatible with pharmaceutical administration.

The use of such media and agents for pharmaceutically active substances is well known in the art. Except insofar as any conventional media or agent is incompatible with the active compound, use thereof in the compositions is contemplated. Supplementary active compounds can also be incorporated into the compositions.

EXEMPLIFICATION

Throughout the examples, the following materials and methods were used unless otherwise stated.

Materials and Methods

In general, the practice of the present invention employs, unless otherwise indicated, conventional techniques of chemistry, nucleic acid chemistry, recombinant DNA technology, molecular biology, biochemistry, immunology, cell culture and animal husbandry. See, e.g., *DNA Cloning*, Vols. 1 and 2, (D. N. Glover, Ed. 1985); *Oligonucleotide Synthesis* (M. J. Gait, Ed. 1984); *Oxford Handbook of Nucleic Acid Structure*, Neidle, Ed., Oxford Univ Press (1999); *RNA Interference: The Nuts & Bolts of siRNA Technology*, by D. Engelke, DNA Press, (2003); *Gene Silencing by RNA Interference: Technology and Application*, by M. Sohail, CRC Press (2004); Sambrook, Fritsch and Maniatis, *Molecular Cloning*: Cold Spring Harbor Laboratory Press (1989); *Antibodies: A Laboratory Manual*, by Harlow and Lane Old Spring Harbor Laboratory Press (1988) and *Current Protocols in Molecular Biology*, eds. Ausubel et al., John Wiley & Sons (1992).

Compound Analysis

General: $^1$H NMR spectra were recorded on a Varian 400 MHz NMR spectrometer, operating at 400 MHz for $^1$H, 100 MHz for $^{13}$C NMR. Chemical shifts are reported in ppm relative to the solvent signal. Thin-layer chromatography was performed on E. Merck silica gel 60 $F_{254}$ plates and spots were visualized with iodine or UV as required. Flash column chromatography was performed using 230-400 mesh silica gels (E-Merck). High resolution mass spectra (HRMS) were recorded on Waters Q-TOF Premier mass spectrometer by direct infusion of solutions of each compound using electro spray ionization (ESI) in positive mode. Low resolution mass spectra were obtained using Waters Alliance HT/Micromass ZQ system (ESI). Anhydrous dichloromethane, N,N-dimethylformamide, dimethylsulfoxide were purchased form Aldrich and used as such. o-nitrophenyl-β-D-galactopyranoside (ONPG), 1,2-dioleoyl-L-α-glycero-3-phosphatidyl ethanolamine (DOPE), 1,2-dioleoyl-L-α-glycero-3-phosphatidyl choline (DOPC), cholesteryl chloroformate, were purchased from Sigma. Unless otherwise stated all the other reagents and chemicals were purchased from commercial vendors, were of analytical grade and used as received. All solvents were dried before use. When required, reactions were carried out under argon atmosphere with standard techniques for the exclusion of air and moisture.

Equipment: Microwave syntheses were carried out on a CEM Corp. Discover laboratory microwave with Explorer unit. All the reactions were carried out in a 10 mL Pyrex reaction vessel. The Discover System consists of a continuous microwave power delivery system with operator selectable power output from 0-300 watts (+/−30 watts) programmable in 3-watt increments. The apparatus consist of an optional infrared temperature control system, pressure control system, stirring and cooling unit all of which were used in the reactions. Temperature is programmable from 25-250° C. while pressure is programmable from 0-300 psi (0-21 bars). The cooling option decreases the temperature of a 2 mL solution in a 10 mL. Pyrex reaction vessel from ~150° C. to 40° C. in less than 2 mins by a cooling gas (nitrogen) onto the vessel in the system cavity. The method setup enables the cooling and the stirring features.

Oligoribonucleotides

RNA oligonucleotides were synthesized by Dharmacon (Lafayette, Colo.). CDK9 siRNA target sequence: 5' CCAAAGCCTCACCGTATAA, sense sequence: 5'CCAAAGCCUCACCGUAUAA, antisense sequence: 5'UUAUACGGUGAGGCUUUGG.

Preparation of Liposomes and Lipid-DNA Complexes

Cationic lipids and the co-lipids in chloroform were dried under a stream of $N_2$ gas and vacuum-desiccated for a minimum of 6 h to remove residual organic solvent. The dried lipid film was hydrated in sterile deionized water at cationic lipid concentration of 1 mM for a minimum of 12 h. Liposomes were vortexed to remove any adhering lipid film and probe sonicated until a clear translucent solution is formed. The pDNA solution was added to the liposomes, mixed properly by pipeting and shaken on a rotary shaker (15-30 mins.) before use.

Plasmids

The pSV-β-gal plasmid was obtained from Promega, amplified in a DH5α strain of *Escherichia coli*, and purified using the QIAfilter plasmid Maxi kit. Plasmid preparations showing a value of $A_{260}/A_{280}$ around 1.9 were used.

RNA Preparation and Real-Time RT-PCR

Total RNA was extracted from tissues or cultured cells using Trizol (Invitrogen, Carlsbad, Calif.), and real-time RT-PCR for CDK9 and GAPDH mRNA quantification was carried out using 200 ng of total RNA and the QuantiTect SYBR Green RT-PCR Kit (Qiagen, Valencia, Calif.) according to the manufacturer's instructions. The ratio of CDK9 and GAPDH mRNA was calculated and expressed as a group average relative to the control group. The specific probe for detection of CDK9 mRNA levels was designed to the following regions of the CDK9 mRNA ORF, the forward primer 5' TCGGAC-CAA AGCCTCACCGTATAA 3', the reverse primer 5' AGCAGCATCTGCATCACTCTC TTG 3'

Confocal Microscopy

Freshly excised tissues were frozen in liquid nitrogen and mounted for crytostat sectioning. Sections of 5 μm were fixed with in 100% acetone at 4° C. for 10 min, air-dried and mounted in Vectashild with DAPI (Vector Laboratories, Inc. Burlingame, Calif.). Slides were viewed and recorded under Leica confocal microscope.

Cells and Cell Culture

HeLa cells (human epithelial carcinoma cell line), A549 cells (human lung carcinoma cell line) and FL83B cells (rat hepatocyte cell line) were obtained from the ATCC. Cells were typically cultured at 37° C. in Dulbecco's modified Eagle's medium (DMEM) and Kaighn's Modification of Ham's F-12 (F-12K) nutrients. A-549 and FL83B cells with cultured with the same and 10% FBS, 50 μg/ml of penicillin and streptomycin, and in a humidified atmosphere containing 5% $CO_2$.

Cell Cytotoxicity Conditions

The Cell Titer-Blue Cell Viability Assay Kit (Promega, Madison, Wis.) was applied to detect and measure cytotoxicity in FL83B cells according to the manufacturer's instructions. Briefly, FL82B cells were plated on 96-well plate in F-12K medium (ATCC, Manassas, Va.) with 10% fetal bovine serum at 37° C. in 5% $CO_2$. At 24 h., liposomes were added to each well at various concentrations and incubated for 24 h at 37° C. in 5% $CO_2$. Afterwards, the Cell Titer-Blue Reagent was added to each well at 20 μl/well and incubated for 4 h at 37° C. in 5% $CO_2$. The fluorescent signal was recorded by a fluorescent reader (560/590 nm).

Alternatively, the cytotoxicity of the lipids was measured using the Cell Titer 96® $AQ_{ueous}$ One Solution Cell Proliferation Assay. The Cell Titer 96® $AQ_{ueous}$ One Solution Reagent contains a tetrazolium compound [3-(4,5-dimethylthiazol-2-yl)-5-(3-carboxymethoxyphenyl)-2(4-sulfophenyl)-2H-tetrazolium, inner salt; MTS[17]] and an electron coupling reagent (phenazine ethosulfate; PES). The cytotoxicity assay was performed in 96 well plates by maintaining the ratio of number of cells to amount of cationic lipid constant as in transfection experiments. MTS was added 24 hours after transfection. Cell Titer 96® $AQ_{ueous}$ One Solution Reagent (20 ul) was pipetted into each well of the 96-well assay plate containing the samples in 100 μl of culture medium. In case of HeLa cells the plates were incubated for 2 hours, whereas for FL83B cells, plates were incubated for 4 hours at 37° C. in a humidified, 5% $CO_2$ atmosphere. Absorbance was then recorded at 490 nm.

Transfection Conditions for RNAi Gene Knock-Down Experiments

FL83B were cultured in F-12K medium (ATCC, Manassas, Va.) with 10% fetal bovine serum at 37° C. in 5% $CO_2$. FL83B were plated on 6-well plates at 70% confluency 24 hours before transfection. CDK9 siRNA were diluted in 50 μl of HEPES Buffered Saline (20 mM HEPES, 150 mM NaCl, pH 7.4, HBS) in a reaction tube, and liposome were diluted in 150 μl HBS in another tube. CDK9 siRNA solution was then mixed with liposome solution gently and incubated for 15 minutes at 25° C. F-12K medium was replaced by fresh 1 ml of Opti-MEM I Medium (Invitrogen, Carlsbad, Calif.). The transfection complexes were added to each well containing cell and medium. The transfection was carried for 6 h at 37° C. in 5% $CO_2$. After transfection the complexes was replaced with fresh growth medium. Cells were incubated for 16 h before harvesting. Gene silencing was monitored by Real-time RT-PCR.

The complexes of CDK9 siRNA (2 μg) and DOATP-Chol (10 μg) or DMTAP-Chol (10 μg) or Transfast-Chol (μg) were added to Opti-MEM I medium and cells were incubated in the mixture for 6 hr. The mixture was then replaced with fresh growth medium and cells were cultured for 16 h. RNA was extracted from cells using Trizol Reagent and real-time RT-PCR for CDK9 and GAPDH mRNA quantification was carried out using 200 ng of total RNA and the QuantiTect SYBR Green RT-PCR Kit. The ratio of CDK9 and GAPDH mRNA was calculated and expressed as a group average relative to the control group. Control incubation was carried out with liposome alone and medium only.

Transfection Conditions for Gene Expression Experiments

Cells were seeded at a density of 20,000 (for HeLa cells), 16,000 (for A-549 cells), 8,000 (for FL83B cells) per well in a 96-well plate 18-24 h before transfection. An amount of 0.30 μg of pDNA was complexed with varying amounts of lipids (to give +/− ratios of 0.3:1, 1:1, 3:1 and 9:1) in plain OPTIMEM (total volume made up to 100 μl) and then shaken on a rotary shaker at room temperature for 20-30 minutes. The complexes were then added to the cells. After 5 h of incubation, 200 μl of complete medium containing 10% FBS in DMEM for HeLa and 10% FBS in F-12K for FL83B and A549 was added to the cells. The medium was changed after 24 h and the reporter gene activity was estimated 48 h after transfection. Cells were washed with PBS (100 μl) and lysed in 50 l lysis buffer (5× reporter lysis buffer diluted to 1×, working concentration). The β-galactosidase activity per well was estimated by adding 50 μl of 2× substrate solution (1.33 mg/ml of ONPG, 0.2 M sodium phosphate, pH 7.15 and 2 mM magnesium chloride) to the lysate in a 96-well plate. Absorbance of the product ortho-nitrophenol was measured at 420 nm. The absorbance values reported are the average values from two replicate experiments performed in the same plate on the same day. Each transfection experiment was performed three times on three different days to control for variations in transfection efficiency.

Animals and In Vivo Administration Conditions

Male BALB/c mice, 6-8 weeks of age and weighting 20-22 g, were purchased form the Jackson Laboratory (Bar Harbor, Me.). Synthetic siRNA were delivered in vivo using following method. For each mice 25 μg of siRNA in 100 μl of HEPES Buffered Saline (20 mM HEPES, 150 mM NaCl, pH 7.4) was transferred into a sterile tube. In a separate sterile tube 125 μg of liposome was mixed with 200 μl HEPES Buffered Saline. The siRNA solution was transferred to the tube containing liposome solution and then incubated at room temperature for 20 minutes. 200 μl of the complexes was injected via the tail vein, using a 1-ml syringe and 27-gauge needle. The injection was repeated 4 and 8 h later. Control mice were injected with an equal volume of liposome. At 24 h after the last injection, the mice were sacrificed and tissues were harvested for further analysis. CDK9 expression level was normalized with GAPDH and then compared to those obtained from control animals and shown as percent expression. The data represent the mean value +/− SD of three to five mice in each group.

EXAMPLE 1

Methods and Compositions for Rapid and Reliable Synthesis of Lipids Comprising Quaternary Amines The following example describes methods and compounds for carrying out the production of lipids comprising a quaternary amine.

Figure 4:
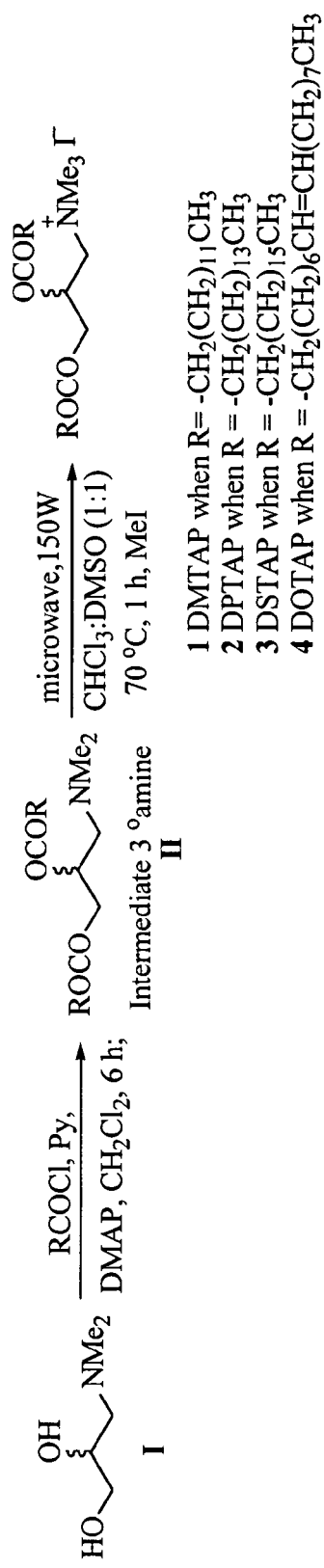
FIG. 4 shows a synthesis scheme describing the preparation of compounds 1-6 wherein the final step is carried out using microwave irradiation.
Figure 4:
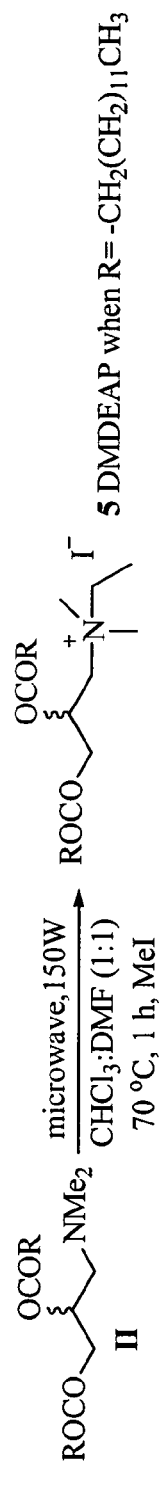
Figure 4:
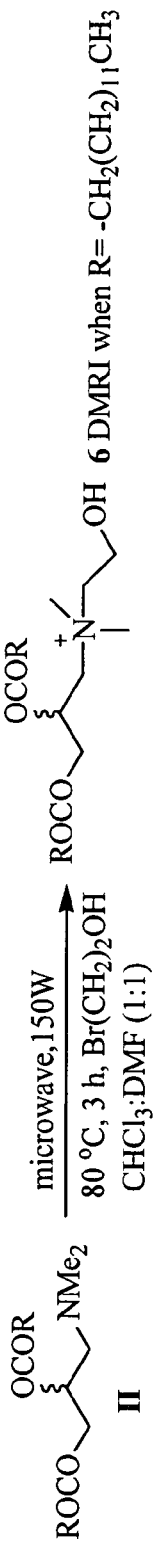

The detailed synthetic procedures for the new and reported cationic lipids using the microwave conditions in the Quarternisation step are outlined below in the experimental section. In the synthesis of the DOTAP analogs (1-4), an equal volume of DMSO and CHCl$_3$ was found to give maximum yield of the compound. FIG. 4 outlines the synthetic procedure for lipids 1-6. The hydroxyl groups of the starting material 3-(dimethylamino)-1,2-propanediol was acylated with RCOCl using pyridine as base following a reported procedure (Bennett, M. J.; Aberle, A. M.; Balasubramaniam, R. P.; Malone, J. G.; Malone, R. W.; Nantz, M. H.; *J. Med. Chem.* 1997, 40, 4069-4078). Since the temperature, reaction time and microwave irradiation power are three important parameters for microwave synthesis, the DOTAP analogs (1-4) were obtained with maximum yields when the mixture of intermediate tertiary amine (II) and methyl iodide in CHCl$_3$:DMSO (1:1) solution was subjected to 150 W microwave irradiation at 70° C. for 1 h to give the target lipids 14. Microwave assisted quarternisation of tertiary amines required lesser quantity of the alkylating reagent (MeI) and shortened the reaction period giving very high yield.

Quarternisation of the tertiary amine (II) was carried out with 2-iodoethane and 2-bromoethanol at 80° C., 3 h, and 150 watts in microwave to yield 72% and 50% of the two compounds DMEAP (5) & DMRI (6) as reported in literature (Bennett, M. J.; Aberle, A. M.; Balasubramaniam, R. P.; Malone, J. G.; Malone, R. W.; Nantz, M. H.; *J. Med. Chem.* 1997, 40, 4069-4078) where the synthesis was done by the conventional methods. The synthesis of these two lipids was carried out to verify the generality of our new procedure for quarternisation of tertiary amines with alkylating agents bulkier than the smaller alkylating agent iodomethane.

Lipids 7 and 8 are new cationic lipids which were designed to improve the transfection efficiency and in vivo stability of lipid 1 and 4. The difference in molecular structure is that one lipid chain of the commercially available transfection reagents 1 & 4 has been replaced by cholesterol hemisuccinate moiety in lipids 7 & 8.

Figure 5:
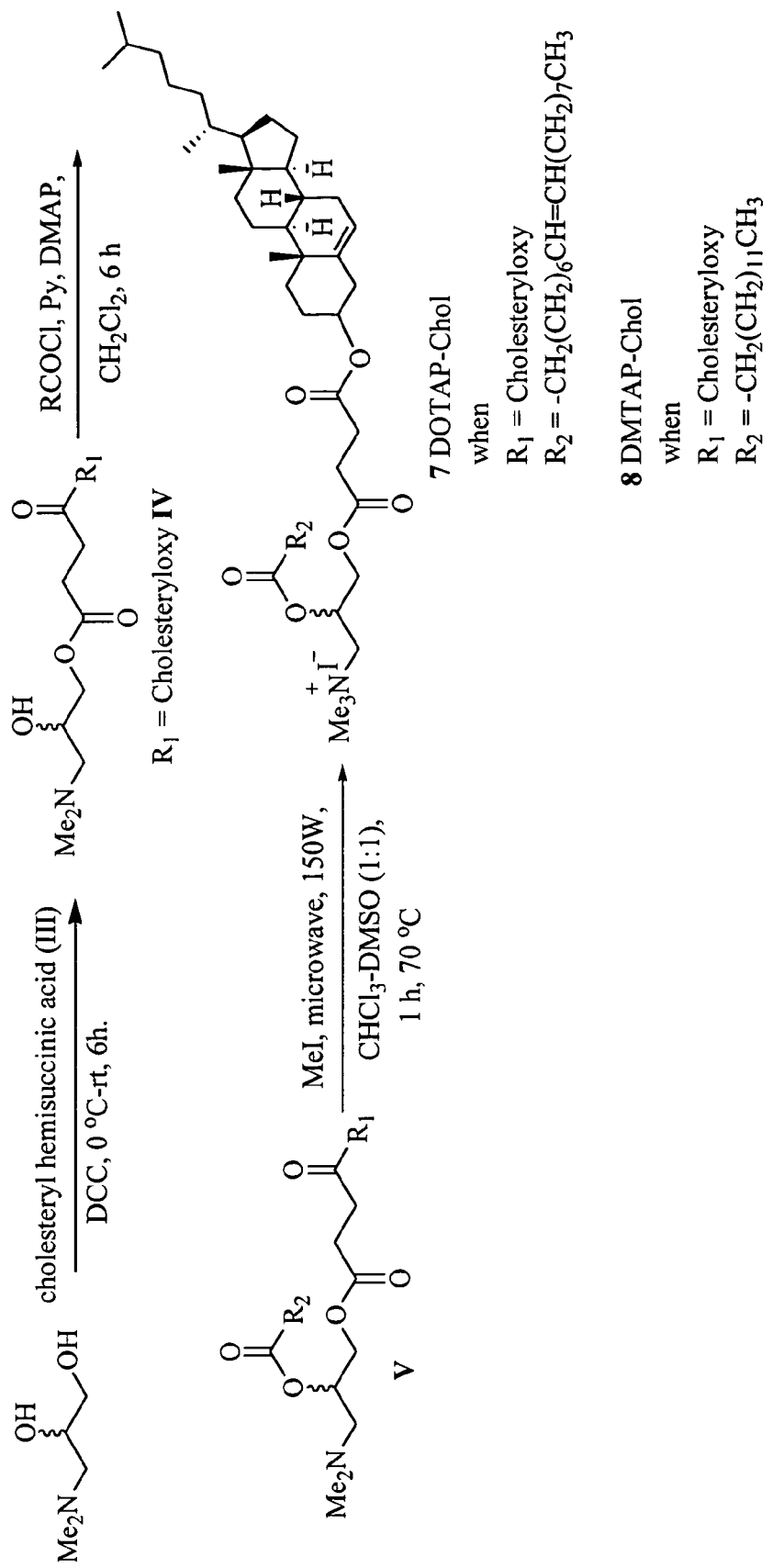
FIG. 5 shows a synthesis scheme describing the preparation of compounds 7 and 8 wherein the final step is carried out using microwave irradiation.

The synthesis strategy for the cholesterol analogs of DOTAP and DMTAP (7 & 8) is shown in FIG. 5. The primary hydroxyl group of the starting material 3-(dimethylamino)-1,2-propanediol was selectively coupled with cholesteryl hemisuccinate using DCC as coupling reagent to give the intermediate (IV) in 34% yield. The free hydroxyl group of the intermediate (IV) was acylated with RCOCl (R=C$_{17}$H$_{33}$, C$_{13}$H$_{27}$) using pyridine as base to give tertiary amine intermediates (V). The tertiary amine intermediates thus obtained were subjected to microwave assisted Quarternisation as stated above to give the new cholesterol analogs (7 & 8) of DOTAP and DMTAP as diastereomeric mixture in very high yield.

Figure 6:
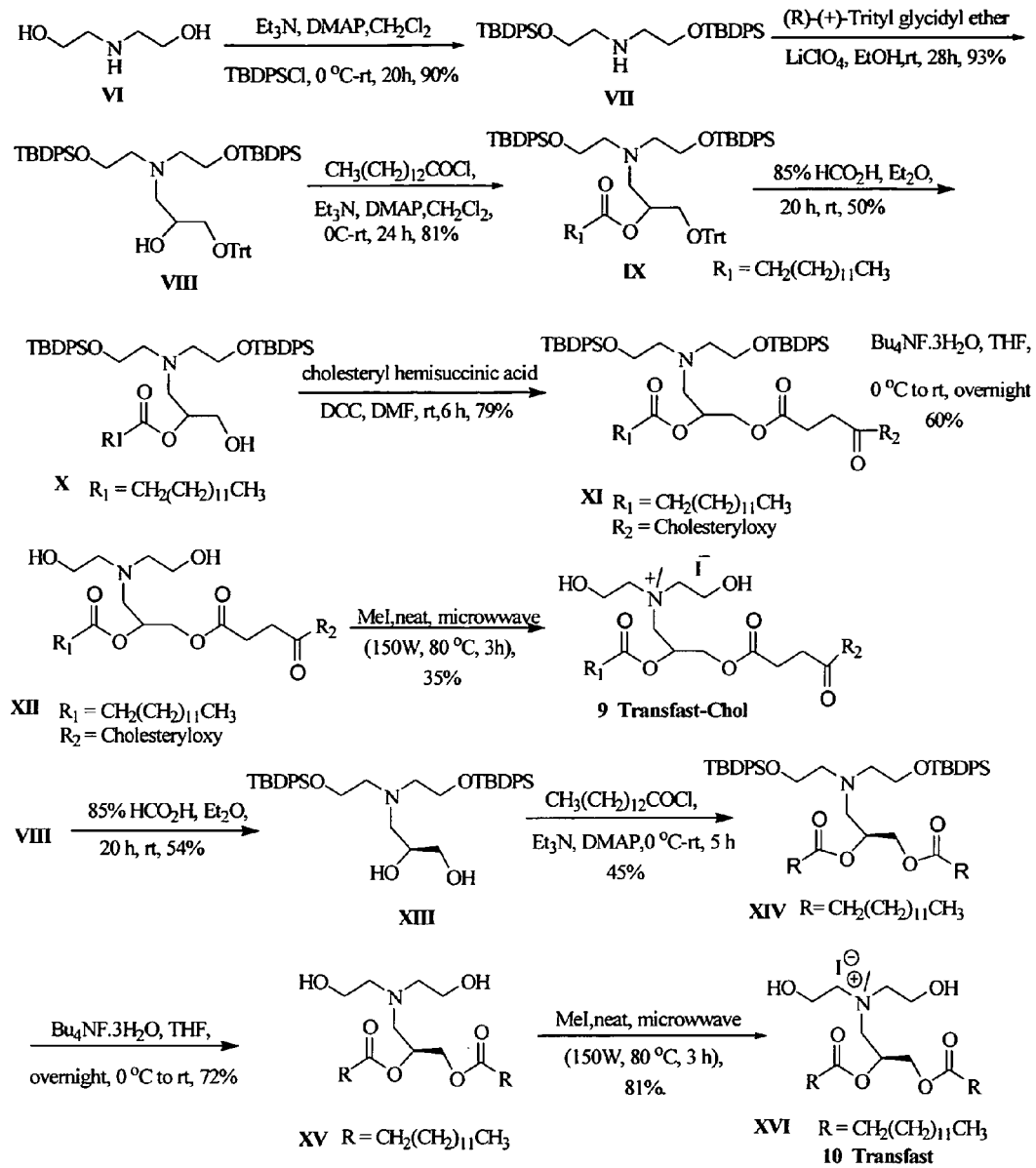
FIG. 6 shows a synthesis scheme describing the preparation of compounds 9-11 wherein the final step is carried out using microwave irradiation.
Figure 6:
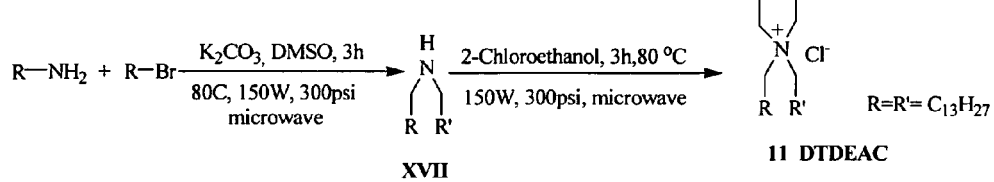
Figure 7:
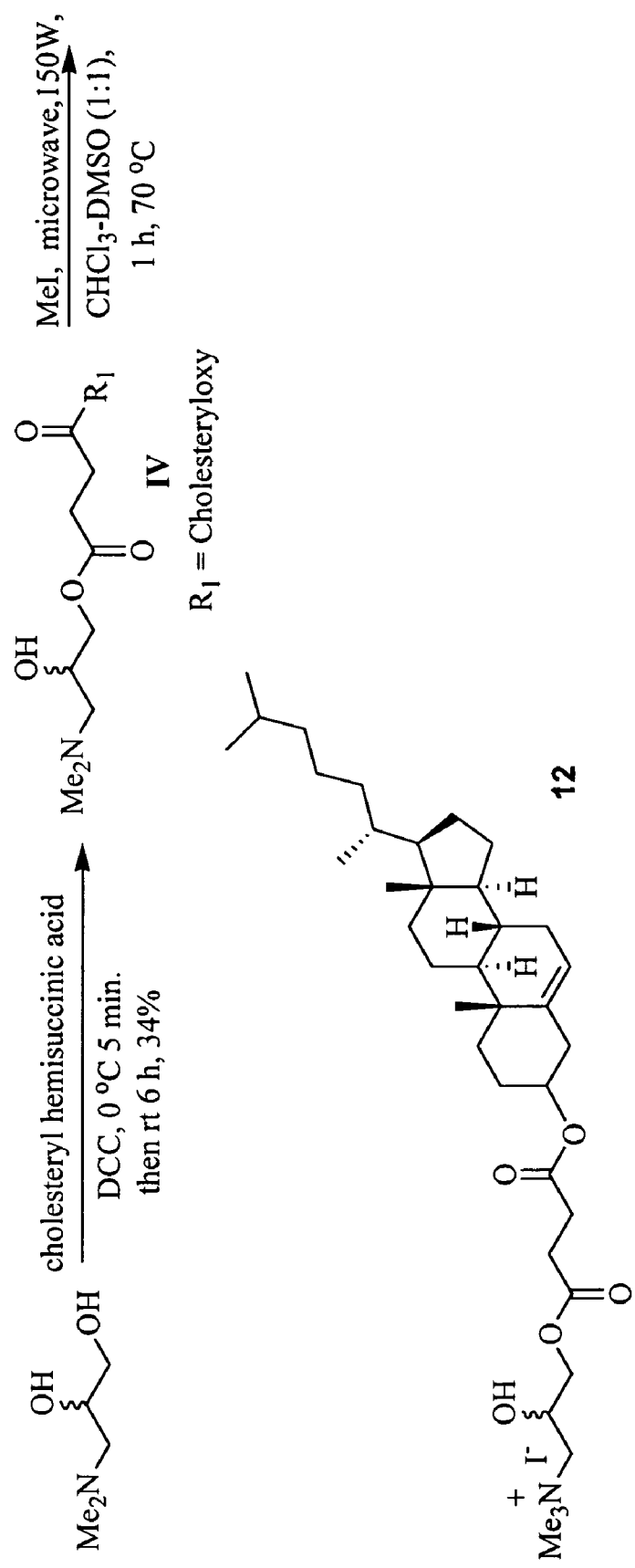
FIG. 7 shows a synthesis scheme describing the preparation of compound 12 wherein the final step is carried out using microwave irradiation.

The synthesis of lipid 10 was carried out following the reported procedure (Nantz et al. U.S. Pat. No. 5,869,715 (1999)) except the microwave assisted quarternisation of tertiary amine in the final step (FIG. 6). Lipid 9 is a new cationic lipid where one of the myristoyl chains of lipid 10 is replaced by cholesteryl hemisuccinate. The synthetic strategy for lipid 9 is shown in FIG. 6. The free hydroxyl group of the intermediate (VIII) was acylated with myristoyl chloride using Et$_3$N as base in presence of catalytic amount of DMAP to give (IX). Trityl deprotection of (IX) was achieved by treating with 85% HCO$_2$H at room temperature to give the intermediate (X). The hydroxyl group of the intermediate X was coupled with the free carboxyl group of cholesteryl hemisuccinate in DMF using DCC as the coupling agent to give (XI) which was next treated with tetra butyl ammonium fluoride trihydrate to give the desilylated intermediate (XII). Quarternisation of the tertiary amine (XII) was performed under 150 W microwave condition at 80° C. for 3 h to give the cholesterol based cationic lipid in 40% yield. Both lipid 9 and 10 had two 2-hydroxyethyl head groups. Accordingly, another lipid was synthesized, i.e., DTDEAC having two 2-hydroxyethyl head groups reported in literature (Singh, R. S.; Mukherjee K.; Banerjee, R K.; Chaudhuri, A.; Hait, S. K.; Moulik, S. P.; Ramdas, Y.; Vijaylakshmi, A.; Rao N. M. *Chem. Eur. J.* 2002, 8, 900-909) using a microwave. The reported procedure of the compound using the conventional procedure involves two steps with the Quarternisation step taking 36 hours. By using the microwave at 150 watts, 3 hours and 80° C. in both the steps, yields almost identical to that reported for the conventional procedure in much less time, were obtained. The first step involves reaction of the alkyl amine with alkyl bromide in CHCl$_3$:DMSO (1:1) and potassium carbonate followed by quarternisation of the secondary amine with 2-chloroethanol (used as both solvent and reagent) and sodium hydroxide to give the desired product.

The success of microwave assisted quarternisation of long chain cationic lipids lead to the exploration of cholesterol backbone based cationic lipids. Lipid 12 was prepared by selective reaction of the 1-hydroxyl group of 3-(dimethylamino)-1,2-propanediol with cholesterol hemisuccinic acid to give the intermediate (IV, FIG. 5). The intermediate was then methylated to give the new quarternised compound 12 (labeled as CC1). DC-Chol is a tertiary lipid that is non-toxic & highly transfection efficient. There have been several reports of quarternised derivatives of DC-Chol (Briane, D.; Lesage, D.; Cao, A.; Coudert, R.; Lievre, N.; Salzman. J. I.; Taillandier, E.; *The Journal of Histochemistry & Cytochemistry.* 2002, 50, 983-991. (d) Reynier, P.; Briane, D.; Coudert, R.; Fadda, G.; Bouchemal, N.; Bissieres, P.; Taillandier, E.; Cap, A. *Journal of Drug Targeting,* 2004, 12, 25-28).

DC-Chol was quarternised by microwave irradiation with four different groups: methyl, ethyl, 2-hydroxyethyl, and 11-hydroxy-un-decyl to give the lipids 13, 14, 15 & 16. The lipid 13 was obtained in one reported procedure under refluxing conditions in anhydrous acetone (Germel, V.; Cao, A.; Briane, D.; Vassay, J.; Rotig, A.; Rustin, P.; Coudert, R.; Rigant, J. P.; Munnich, A.; Taillandier, E. *Antisense and Nucleic Acid Drug Development.* 2001, 11, 175-180) and in another at 40° C. for 4 hours (Sokolova, T. V.; Klesareva, Y. S.; Serebrennikova, G. A.; *Russian Journal of Organic Chemistry.* 2004, 40, 334-336) with 64 and 78% yields, respectively. Using the microwave conditions we were able to achieve 96% yield of lipid 13 in 1 hour at 70° C. using 150 W. For the lipid 14 one of the methyl groups of lipid 13 was replaced by an ethyl group. Using the same reaction conditions as for lipid 13 lead to 94% yield of lipid 14. Lipids 15 (Gerszberg, Szepsel; Daniel, Alonsol.; PCT Int. Appl. (2003), WO 2003035669) and 16 are structurally similar cationic lipids the only difference being the spacer arm between the hydroxyl group and the amide bond. While lipid 15 has two spacer arm, lipid 16 has an un-decyl spacer arm. The reported procedure for lipid 15 involves the refluxing of DC-Chol with excess 2-bromoethanol and N,N-disopropylethylamine in anhydrous acetone for 24 hours with 52% yield. Using the microwave conditions at 80° C., 150 watts, 3 h, and in equal volumes of chloroform (1 mL) and dimethylformamide (1 mL) we were able to obtain lipids 15 and 16 with 78% and 49% yields, respectively. Thus, the microwave conditions provided reduced reaction times and increased reaction yields, and provided almost identical yields with that obtained in a conventional procedure with a much longer spacer arm.

Accordingly, the data obtained from these experiments indicates that the lipid chemistry of the invention is fast, safe, and reliable and is suitable for making novel compounds.

Specific Synthesis Details Follow:

(±)-N,N-Dimethyl-N-[2,3-bis(tetradecanoyloxy)-propyl]amine (II)

To a mixture of 3-(dimethylamino)propane-1,2-diol (0.5 g, 4.2 mmoles), pyridine (1.70 mL, 21 mmoles) and 4-dimethylaminopyridine (catalytic amount) in 10 mL of dry dichloromethane was added myristoyl chloride (2.6 g, 10.5 mmoles) at 0° C. The reaction was allowed to proceed from 0° C. to room temperature for 6 hours. The reaction mixture was extracted with chloroform (50 mL), washed with 5% sodium bicarbonate (3×25 mL), followed by water (2×25 mL) and brine solution (2×25 mL). The chloroform extract was evaporated on a rotary evaporator and the residue was loaded on a silica gel (230-400 mesh), eluted with 0.2% methanol in chloroform to afford a waxy white solid (yield 72%)

$^1$H NMR: (400 MHz, CDCl$_3$): δ/ppm=0.88 [t, 6H, C$\underline{H}_3$—(CH$_2$)$_n$—]; 1.20-1.4 [m, 40H, —(CH$_2$)$_{10}$—]; 1.5-1.7 [m, 4H, —OCO—CH$_2$—C$\underline{H}_2$—(CH$_2$)$_{10}$—]; 2.25 [s, 6H, —N(CH$_3$)$_2$]; 2.30-2.40 [dt, 4H, —OCO—C$\underline{H}_2$—C$\underline{H}_2$—(CH$_2$)$_{10}$—]; 2.40-2.60 [m, 2H, —O—CH$_2$—C$\underline{H}$—CH$_2$—N(CH$_3$)$_2$]; 4.08 [dd, 1H, H$^1$C$\underline{H}^2\overline{O}$COR—CHOCOR—CH$_2$N(CH$_3$)$_2$]; 4.35 [dd, 1H, $\overline{H}^1$CH$^2$OCOR—CHOCOR—CH$_2$N(CH$_3$)$_2$]; 5.15-5.24 [m, 1H, $\overline{C}$H$_2$OCOR—CHOC—OR—CH$_2$—N(CH$_3$)$_2$].

Another batch of (±)-N,N-Dimethyl-N-[2,3-bis(tetradecanoyloxy)-propyl]amine was prepared, and yielded the following NMR spectra coordinates: $^1$H NMR (CDCl$_3$): δ 5.24-5.15 (m, 1H), 4.35 (dd, J=12.0, 3.2 Hz, 1H), 4.08 (dd, J=11.6, 6.0 Hz, 1H), 2.52-2.38 (m, 2H), 2.30 (dt, J=7.2, 3.6 Hz, 4H), 2.61 (s, 6H), 1.67-1.53 (m, 4H), 1.36-1.17 (m, 40H), 0.87 (t, J=6.4 Hz, 6H).

$^1$H NMR of (±)-N,N-Dimethyl-N-[2,3-bis(hexadecanoyloxy)-propyl]amine (2): (400 MHz, CDCl$_3$): δ/ppm=0.96 [t, 6H, CH$_3$—(CH$_2$)$_n$—]; 1.20-1.4 [m, 48H, —(CH$_2$)$_{10}$—]; 1.5-1.7 [m, 4H, —OCO—CH$_2$—CH$_2$—(CH$_2$)$_{10}$—]; 2.25 [s, 6H, —N(CH$_3$)$_2$]; 2.30-2.40 [2t, 4H, —OCO—CH$_2$—CH$_2$—(CH$_2$)$_{10}$—]; 2.40-2.60 [m, 2H, —O—CH$_2$—CH—CH$_2$—N(CH$_3$)$_2$]; 4.10 [dd, 1H, H$^1$CH$^2\overline{O}$COR—CHOCOR—CH$_2$N(CH$_3$)$_2$]; 4.37 [dd, 1H, $\overline{H}^1$CH$^2$OCOR—CHOCOR—CH$_2$N(CH$_3$)$_2$]; 5.2 [m, 1H, CH$_2\overline{O}$COR—CHOC—OR—CH$_2$—N(CH$_3$)$_2$]

$^1$H NMR of (±)-N,N-Dimethyl-N-[2,3-bis(octadecanoyloxy)-propyl]amine (3): (400 MHz, CDCl$_3$): δ/ppm=0.87 [t, 6H, CH$_3$—(CH$_2$)$_n$—]; 1.20-1.4 [m, 56H, —(CH$_2$)$_{10}$—]; 1.5-1.7 [m, 4H, —OCO—CH$_2$—CH$_2$—(CH$_2$)$_{10}$—]; 2.25 [s, 6H, —N(CH$_3$)$_2$]; 2.30-2.40 [dt, 4H, —OCO—CH$_2$—CH$_2$—(CH$_2$)$_{10}$—]; 2.40-2.60 [m, 2H, —O—CH$_2$—CH—CH$_2$—N(CH$_3$)$_2$]; 4.08 [dd, 1H, H$^1$CH$^2\overline{O}$COR—CHOCOR—CH$_2$N(CH$_3$)$_2$]; 4.35 [dd, 1H, $\overline{H}^1$CH$^2$OCOR—CHOCOR—CH$_2$N(CH$_3$)$_2$]; 5.15-5.24 [m, 1H, $\overline{C}$H$_2$OCOR—CHOC—OR—CH$_2$—N(CH$_3$)$_2$]

(±)-N,N-Dimethyl-N-[2,3-bis(9-(Z)-octadecanoyloxy)-propyl]amine (II)

An alternative synthesis is as follows: to a solution of 3-(dimethylamino)-1,2-propandiol (0.2 mL, 1.68 mmol), pyridine (0.55 mL, 6.72 mmol) and DMAP (20 mg, 0.17 mmol), in CH$_2$Cl$_2$ (10 mL) at 0° C. was added dropwise oleoyl chloride (1.38 mL, 4.2 mmol). The reaction mixture was allowed to warm up slowly to room temperature. After stirring for 6 hours at room temperature, the reaction mixture was diluted with CH$_2$Cl$_2$ (50 mL), washed sequentially with 5% aqueous sodium bicarbonate (15 mL), water (15 mL), and saturated aqueous NaCl (15 mL). The organic layer was dried (Na$_2$SO$_4$), filtered and concentrated in vacuo. Purification by column chromatography (SiO$_2$, elution with 0.2% MeOH in CHCl$_3$) furnished compound II (0.782 g, 72%) as oily liquid. NMR spectra coordinates are as follows: $^1$H NMR (CDCl$_3$): δ 5.47-5.32 (m, 4H), 5.28-5.18 (m, 1H), 4.40 (dd, J=11.8, 3.0 Hz, 1H), 4.13 (dd, J=12.0, 6.8 Hz, 1H), 2.56-2.42 (m, 2H), 2.35 (dt, J=7.6, 2.8 Hz, 4H), 2.30 (s, 6H), 2.12-1.97 (m, 8H), 1.71-1.58 (m, 4H), 1.44-1.23 (m, 40H), 0.92 (t, J=7.0 Hz, 6H).

Another crop of (±)-N,N-Dimethyl-N-[2,3-bis(9-(Z)-octadecanoyloxy)-propyl]amine (II) was prepared and had the following $^1$H NMR characteristics: (400 MHz, CDCl$_3$): δ/ppm=0.96 [t, 6H, CH$_3$—(CH$_2$)$_n$—]; 1.20-1.4 [m, 40H, —(CH$_2$)$_{10}$—]; 1.5-1.7 [m, 4H, —OCO—CH$_2$—CH$_2$—(CH$_2$)$_{10}$—]; 2.25 [s, 6H, —N(CH$_3$)$_2$]; 2.30-2.40 [2t, 4H, —OCO—CH$_2$—CH$_2$—(CH$_2$)$_{10}$—]; 2.42-2.56 [m, 2H, —O—CH$_2$—CH—CH$_2$—N(CH$_3$)$_2$]; 4.13 [dd, 1H, H$^1$CH$^2$OCOR—CHOCOR—CH$_2$N(CH$_3$)$_2$]; 4.40 [dd, 1H, $\overline{H}^1$CH$^2$OCOR—CHOCOR—CH$_2$N(CH$_3$)$_2$]; 5.18-5.28 [m, 1H, $\overline{C}$H$_2$OCOR—CHOC—OR—CH$_2$—N(CH$_3$)$_2$], 5.40 [(m, 4H, —CH$_2$—CH═CH—CH$_2$—].

(±)-N,N,N-Trimethyl-N-[2,3-bis(tetradecanoyloxy)-propyl]ammonium iodide (DMTAP, 1)

The tertiary amine II (0.150 g, 0.28 mmoles) and methyl iodide (0.0468 g, 0.33 mmoles) were taken in a 10 mL thick walled pyrex glass with a stirrer bar, dissolved in 1 mL of chloroform:dimethylsulfoxide (1:1). The reaction was carried out at 70° C., 150 W, 300 psi in a microwave synthesizer for 1 hour. The solvents were removed on a rotary evaporator followed by vacuum pump. The residue was loaded on a silica gel (230-400 mesh size) and eluted with 8% methanol in chloroform to give a white solid on subsequent lyophilization (0.148 g, yield 96%, $R_f$~0.2)

$^1$H-NMR: (400 MHz, CDCl$_3$): δ/ppm=0.88 [(t, 6H, C$\underline{H}_3$—CH$_2$—C$_{15}$H$_{28}$—)]; 1.20-1.40 [(m, 40H, —(C$\underline{H}_2$)$_n$—)]; 1.50-1.68 [(m, 4H, —C$\underline{H}_2$—CH$_2$—CO—O—)]; 2.25-2.40 [(dt, 4H, —CH$_2$—C$\underline{H}_2$—CO—O—)]; 3.35 [(s, 9H, (C$\underline{H}_3$)$_3$N$^+$—)]; 3.76 [(dd, 1H, CH$^1\underline{H}^2$OCOR—CHOCOR—H$^1$H$^2$C—N(CH$_3$)$_3$)], 4.07 [(dd, 1H, C$\underline{H}^1$H$^2$OCOR—CHOCOR—H$^1$H$^2$C—N(CH$_3$)$_3$)] 4.18 [(d, 1H, CH$_2$OCOR—C$\underline{H}$OCOR—H$^1$H$^2$C—N(CH$_3$)$_3$]; 4.45 [(d, 1H, CH$_2$OCOR—CHOCOR—$\underline{H}^1$H$^2$C—N(CH$_3$)$_3$] 5.51-5.59 [(m, 1H, CH$_2$)COR—CHOC—OR—CH$_2$—N(CH$_3$)$_3$)].

(ESI) m/z (M)$^+$ 554.48; HRMS (ESI) m/z: Calcd (for C$_{34}$H$_{68}$NO$_4$, the 4° ammonium ion, 100%) 554.5148. found 554.5140.

The synthesis of a second crop of 1 yielded the following characteristics: $^1$H-NMR (CDCl3): δ 5.59-5.51 (m, 1H), 4.45 (dd, J=12.0, 3.6 Hz, 1H), 4.18 (d, J=14.0 Hz, 1H), 4.07 (dd, J=12.0, 5.6 Hz, 1H), 3.76 (dd, J=14.8, 8.8 Hz, 1H) 3.35 (s, 9H), 2.31 (dt, J=13.6, 2.0 Hz, 4H), 1.63-1.51 (m, 4H), 1.33-1.14 (m, 40H), 0.84 (t, J=7.2 Hz, 6H); $^{13}$C NMR (CDCl$_3$) δ 173.63, 173.11, 66.54, 65.83, 63.21, 54.84, 34.35, 34.10, 32.10, 29.86, 29.83, 29.80, 29.68, 29.64, 29.54, 29.49, 29.42, 29.29, 29.26, 24.91, 24.80, 22.87, 14.27; MS (ESI) m/z 555.18 (M+).

(±)-N,N,N-Trimethyl-N-[2,3-bis(hexadecanoyloxy)-propyl]ammonium iodide (DPTAP, 2)

$^1$H-NMR: (400 MHz, CDCl$_3$) δ/ppm=0.88 [(t, 6H, C$\underline{H}_3$—CH$_2$—C$_{15}$H$_{28}$—)]; 1.20-1.40 [(m, 48, —(C$\underline{H}_2$)$_n$—)]; 1.50-1.68 [(m, 4H, —C$\underline{H}_2$—CH$_2$—CO—O—)]; 2.25-2.40 [(4H, —CH$_2$—C$\underline{H}_2$—CO—O—)]; 3.50 [(s, 9H, (C$\underline{H}_3$)$_3$N$^+$—)]; 3.70-3.90 [(m, 1H, CH$_2$OCOR—CHOCOR—H$^1$H$^2$C—N(CH$_3$)$_3$)], 4.1-4.2 [(m, 1H, CH$_2$OCOR—CHOCOR—H$^1$H$^2$C—N(CH$_3$)$_3$]; 5.60 [(m, 1H, CH$_2$)COR—C HOC—OR—CH$_2$—N(CH$_3$)$_3$)].

(ESI) m/z (M)$^+$ 611.10; HRMS (ESIMS) m/z: Calcd (for C$_{38}$H$_{76}$NO$_4$, the 4° ammonium ion, 100%) 610.5774. found 610.5768

(±)-N,N,N-Trimethyl-N-[2,3-bis(octadecanoyloxy)-propyl]ammonium iodide (DSTAP, 3)

$^1$H-NMR: (400 MHz, CDCl$_3$): δ/ppm=0.88 [(t, 6H, C$\underline{H}_3$—CH$_2$—C$_{15}$H$_{28}$—)]; 1.20-1.40 [(m, 48, —(C$\underline{H}_2$)$_n$—)]; 1.50-1.68 [(m, 4H, —C$\underline{H}_2$—CH$_2$—CO—O—)]; 2.25-2.40 [(4H, —CH$_2$—C$\underline{H}_2$—CO—O—)]; 3.50 [(s, 9H, (C$\underline{H}_3$)$_3$N$^+$—)]; 3.70-3.90 [(m, 1H, CH$_2$OCOR—CHOCOR—H$^1$H$^2$C—N(CH$_3$)$_3$)], 4.1-4.2 [(m, 1H, CH$_2$OCOR—CHOCOR—H$^1$H$^2$C—N(CH$_3$)$_3$]; 5.60 [(m, 1H, CH$_2$)COR—C HOC—OR—CH$_2$—N(CH$_3$)$_3$)]

(ESI) m/z: 667.1201 (M$^+$); HRMS (LSIMS) m/z: Calcd (for C$_{42}$H$_{84}$NO$_4$, the 4° ammonium ion, 100%) 666.6400. found 666.6393.

(±)-N,N,N-Trimethyl-N-[2,3-bis(9-(Z)-octadecanoyloxy)-propyl]ammonium iodide (DOTAP, 4)

A Solution of (±)-N,N-Dimethyl-N-[2,3-Bis(9-(Z)-Octadecanoyloxy)-propyl]amine (190 mg, 0.29 mmol) and methyl iodide (0.022 mL, 0.35 mmol) in CHCl$_3$ (1 mL) and DMSO (1 mL) was added to a 10 mL glass tube covered with a plastic cap. The reaction mixture was subjected to 150 W microwave irradiation at 70° C. for 1 h. The reaction mixture was concentrated to dryness under high vacuum. Purification of this crude product by column chromatography (SiO$_2$, elution with 8% MeOH in CHCl$_3$) furnished 4 (263 mg, 90%) as a white solid. NMR spectra coordinates are as follows: $^1$H NMR (CDCl$_3$): δ 5.64-5.56 (m, 1H), 5.39-5.28 (m, 4H), 4.58-4.47 (m, 2H), 4.14 (dd, J=12.0, 5.6 Hz, 1H), 3.86 (dd, J=14.4, 8.8 Hz, 1H), 3.53 (s, 9H), 2.35 (t, J=2.6 Hz, 4H), 2.07-1.92 (m, 8H), 1.69-1.53 (m, 4H), 1.39-1.18 (m, 40H), 0.87 (t, J=7.2 Hz, 6H); $^{13}$C NMR (CDCl$_3$) δ 173.42, 172.96, 130.30, 130.26, 129.91, 128.85, 66.44, 65.88, 63.08, 55.02, 34.41, 34.19, 32.13, 29.99, 29.97, 29.93, 29.76, 29.55, 29.48, 29.40, 29.39, 29.33, 29.31, 29.29, 27.45, 27.42, 27.39, 24.97, 24.84, 22.91, 14.36; MS (ESI) m/z 663.37 (M$^+$).

Another batch of (±)-N,N,N-Trimethyl-N-[2,3-bis(9-(Z)-octadecanoyloxy)-propyl]ammonium iodide (DOTAP, 4) was prepared and had the following characteristics: $^1$H-NMR: (400 MHz, CDCl$_3$) δ/ppm=0.88 [(t, 6H, C$\underline{H}_3$—CH$_2$—C$_{15}$H$_{28}$—)]; 1.20-1.40 [(m, 48, —(C$\underline{H}_2$)$_n$—)]; 1.50 [(m, 4H, —C$\underline{H}_2$—CH$_2$—CO—O—)]; 2.0 [(m, 8H, —C$\underline{H}_2$—CH=CH—C$\underline{H}_2$—); 2.25-2.40 [(4H, —CH$_2$—C$\underline{H}_2$—CO—O—)]; 3.50 [(s, 9H, (CH$_3$)$_3$N$^+$—)]; 3.90 [(m, 1H, C$\underline{H}^1$H$^2$OCOR—CHOCOR—H$_2$C—N(CH$_3$)$_3$)]; 4.10-4.20 [(m, 1H, CH$^1\underline{H}^2$OCOR—CHOCOR—H$_2$C—N(CH$_3$)$_3$)], 4.50 [(m, 1H, CH$_2$OCOR—C$\underline{H}$OCOR—H$^1$H$^2$C—N(CH$_3$)$_3$]; 5.32 (m, 4H, —CH$_2$—CH=CH—CH$_2$—); 5.60 [(m, 1H, CH$_2$)COR—C HOC—OR—CH$_2$—N(CH$_3$)$_3$)].

(ESI) m/z 663.22 (M)$^+$; HRMS (LSIMS) m/z: Calcd (for C$_{42}$H$_{80}$NO$_4$, the 4° ammonium ion, 100%) 662.6087. found 662.6006.

(±)N-Ethyl-N,N-dimethyl-N-[2,3-bis(tetradecanoyloxy)propyl]ammonium chloride (DMEAP, 5)

The intermediate II (0.126 g, 0.24 mmoles) and 2-iodoethane (0.0355 g, 0.28 mmoles) were dissolved in 2 mL of CHCl$_3$:DMF (1:1) for 3 h at 80° C. & 150 watts. The solvents were removed on a rotary evaporator followed by the removal of DMF on the vacuum pump. The residue was loaded on silica gel and eluted with 8-10% methanol in CHCl$_3$ to yield 0.071 of the compound as white solid (yield 52%)

$^1$H-NMR (400 MHz, CDCl$_3$): δ 5.61 (m, 1H), 4.52 (dd, J=3.12 Hz, 1H), 4.32 (d, J=14 Hz, 1H), 4.11 (dd, J=6, 12 Hz, 1H), 3.82-3.63 (m, 3H), 3.45 (s, 3H), 3.43 (s, 3H), 2.30 (m, 4H), 1.56 (m, 4H), 1.42 (t, J=7 Hz, 3H), 1.23 (s, 40H), 0.86 (t, J=7 Hz, 6H).

(ESI) m/z 569.35 (MH)$^+$; HRMS (LSIMS) m/z: Calcd (for C$_{35}$H$_{70}$NO$_4$ the 4° ammonium ion, 100%) 568.5305. found 568.5285

(±)N-(2-Hydroxyethyl-N,N-dimethyl-N-[2,3-is(tetradecanoyloxy)propyl]ammonium chloride (DMRI, 6)

The intermediate II (0.126 g, 0.24 mmoles) and 2-bromoethanol (0.0355 g, 0.28 mmoles) were dissolved in 2 mL of CHCl$_3$:DMF (1:1) for 3 h at 80° C. & 150 watts. The solvents were removed on a rotary evaporator followed by the removal of DMF on the vacuum pump. The residue was loaded on silica gel and eluted with 8-10% methanol in CHCl$_3$ to yield 0.071 of the compound as white solid (yield 52%).

$^1$H-NMR (400 MHz, CDCl$_3$): δ 5.77 (m, 1H), 5.65 (m, 1H), 4.48 (dd, J=3, 12 Hz, 1H), 4.36 (d, J=14 Hz, 1H), 4.10 (m, 5H), 3.78 (m, 5H), 3.41 (s, 3H), 3.39 (s, 3H), 2.31 ((q, J=18 Hz, 4H), 1.57 (m, 4H), 1.23 (m, 40H), 0.86 (t, J=7 Hz, 6H).

(ESI) m/z 585.23 (MH)+; HRMS (LSIMS) m/z: Calcd (for $C_{35}H_{70}NO_5$, the 4° ammonium ion, 100%) 584.5254. found 584.5153.

3-((Cholester-3-yloxy)carbonyl)propanoic acid (Cholesterol Hemisuccinic Acid III)

The acid was prepared by the conventional procedure. To a solution of cholesterol (1.0 g, 2.5 mmoles) in dry dichloromethane was added succinic anhydride (0.25 g, 2.5 mmoles) and 4-dimethyaminopyridine (0.305 g, 2.5 mmoles) under nitrogen atmosphere, which was allowed to stir overnight at room temperature. The reaction mixture was extracted with chloroform (50 mL) and washed with ammonium chloride solution (3×25 mL) followed by brine solution (3×20 mL). The chloroform extract was dried over sodium sulfate and evaporated on a rotary evaporator. Silica gel column chromatographic purification of the resulting residue using 230-400 mesh silica gel size and 5-6% methanol in chloroform (v/v) as the eluent afforded the title compound as a white solid (2.0 g, 71% yield, $R_f$=0.5, 10:90, v/v, methanol:chloroform).

$^1$H NMR (400 MHz, CDCl$_3$): δ/ppm=0.6-2.30 [m, 43H, cholesteryl skeleton]; 2.60 [t, Chol-OCO—CH$_2$—]; 2.70 [t, Chol-OCO—CH$_2$—CH$_2$—COOH]; 4.60 [$\overline{m}$, 1H, $\underline{H}_{3\alpha}$ (Chol)]; 5.40 [$\overline{m}$, 1H, $\overline{\underline{H}}_6$ (Chol)].

N,N-Dimethyl-N-[2-hydroxy,3-succinyloxy(4-cholesteryloxy)-propyl]amine (IV)

To a solution of 3-dimethylamino-1,2-propanediol (0.5 g, 3.6 mmoles) in 10 mL dichloromethane was added cholesterylhemisuccinic acid (1.75 g, 3.6 mmoles) and DCC (1.48 g, 7.2 mmoles) at 0° C. The reaction was allowed to proceed from 0° C. (15 mins) to room temperature for 6 hours. DCU was filtered off and the filtrate was evaporated on a rotary evaporator and loaded on a silica gel (230-400 mesh). The desired product was eluted with 4-5% methanol in chloroform (v/v) to give a colorless thick liquid (0.834 g, $R_f$~0.5 in 10% methanol in chloroform, yield 34%).

$^1$H NMR (400 MHz, CDCl$_3$): δ 5.36 (d, J=4.0 Hz, 1H), 4.67-4.56 (m, 1H), 4.19 (dd, J=11.6, 3.6 Hz, 1H), 4.04 (dd, J=11.6, 6.0 Hz, 1H), 3.97-3.89 (m, 1H), 2.70-2.56 (m, 4H), 2.44 (t, J=10.0 Hz, 1H), 2.36-2.23 (m, 9H), 2.05-1.75 (m, 5H), 1.66-0.80 (m, 33H), 0.67 (s, 3H).

An alternative synthesis procedure is as follows: to an ice-cooled solution of cholesteryl hemisuccinate (4.09 g, 8.42 mmol) in DMF (35 mL) 3-(dimethylamino)-1,2-propandiol (1.0 mL, 8.42 mmol) was added N,N'-dicyclohexylcarbodiimide (3.47 g, 16.84 mmol). After 5 min., the ice bath was removed and the solution was stirred for an additional 6 h at room temperature. The resulting precipitation of dicyclohexylurea was removed by filtration. The filtrate was transferred to a 100 mL round bottom flask and concentrated to dryness under vacuum. The pasty mass was dissolved in CHCl$_3$ (200 mL) and washed with H$_2$O (30 mL), saturated aqueous NaCl (30 mL), dried (Na$_2$SO$_4$) and concentrated in vacuo. Purification by column chromatography (SiO$_2$, elution with 5% MeOH in CHCl$_3$) furnished IV (1.68 g, 34%) as wax. NMR spectra coordinates are as follows: $^1$H NMR (CDCl$_3$): δ 5.36 (d, J=4.0 Hz, 1H), 4.67-4.56 (m, 1H), 4.19 (dd, J=11.6, 3.6 Hz, 1H), 4.04 (dd, J=11.6, 6.0 Hz, 1H), 3.97-3.89 (m, 1H), 2.70-2.56 (m, 4H), 2.44 (t, J=10.0 Hz, 1H), 2.36-2.23 (m, 9H), 2.05-1.75 (m, 5H), 1.66-0.80 (m, 33H), 0.67 (s, 3H).

N,N-Dimethyl-N-[2-(tetradecanoyloxy),3-succinyloxy(4-cholesteryloxy)propyl]amine (V)

To a solution of 3-dimethylamino-2-hydroxypropylcholester-3-yl succinate (0.33 g, 0.56 mmoles) in 6 mL dichloromethane was added pyridine (0.055 g, 0.84 mmoles), myristoyl chloride (0.12 g, 0.56 mmoles) and a catalytic amount of DMAP at 0° C. The reaction was allowed to proceed from 0° C. to room temperature for 5 hours. The reaction mixture was extracted with chloroform (20 mL), washed with 5% sodium bicarbonate (4×10 mL) followed by brine solution (3×10 mL), dried over sodium sulfate. The chloroform solution was evaporated on a rotary evaporator and loaded on silica gel (230-400 mesh) and eluted with 0-0.4% methanol in chloroform to give the desired product as a fluffy white solid (0.389 g, yield 87%).

$^1$H NMR (400 MHz, CDCl$_3$): $^1$H NMR (CDCl$_3$): δ 5.36 (d, J=4.8 Hz, 1H), 5.22-5.14 (m, 1H), 4.66-4.56 (m, 1H), 4.37 (dd, J=12.0, 3.2 Hz, 1H), 4.11 (dd, J=11.6, 6.0 Hz, 1H), 2.67-2.54 (m, 4H), 2.43 (dt, J=14.0, 7.2 Hz, 2H), 2.35-2.27 (m, 4H), 2.25 (s, 6H), 2.03-1.90 (m, 2H), 1.89-1.66 (m, 3H), 1.68-0.82 (m, 58H), 0.67 (s, 3H).

N,N,N-Trimethyl-N-[2-(tetradecanoyloxy),3-succinyloxy(4-cholesteryloxy)-propyl]ammonium iodide (DMTAP-Chol, 7)

The intermediate V (0.175 g, 0.22 mmoles) was dissolved in 1 mL of chloroform:dimethylsulfoxide (1:1) and methyl iodide (0.037 g, 0.26 mmoles) was added to the solution. The reaction was carried out in a Microwave Synthesiser at 70° C., 150 W, 300 psi for 1 hour. The conversion was 100%. Chloroform was removed on a rotary evaporator and dimethylsulfoxide was removed under high vacuum. Silica gel column chromatographic purification of the resulting residue using 230-400 mesh silica gel size and 7-10% methanol in chloroform (v/v) as the eluent afforded the title compound as a fluffy white solid (0.168 g, yield 96%, $R_f$=0 in 10% methanol in chloroform) which on lyophilisation afforded the target compound in powder form.

$^1$H NMR (400 MHz, CDCl$_3$): δ $^1$H NMR (CDCl$_3$): δ 5.62-5.52 (m, 1H), 5.37-5.29 (m, 1H), 4.60-4.50 (m, 1H), 4.48 (dd, J=12.4, 4.4 Hz, 1H), 4.41 (d, J=13.6 Hz, 1H), 4.21 (dd, J=12.4, 4.8 Hz, 1H), 3.96 (dd, J=16.0, 9.2 Hz, 1H), 3.52 (s, 9H), 2.70-2.56 (m, 4H), 2.35 (dt, J=7.6, 3.6 Hz, 2H), 2.32-2.22 (m, 2H), 2.04-1.75 (m, 5H), 1.64-0.78 (m, 58H), 0.65 (s, 3H). $^{13}$C NMR (CDCl$_3$) δ 172.93, 172.22, 172.07, 139.69, 123.07, 74.82, 66.12, 65.92, 62.89, 56.87, 56.34, 54.96, 50.14, 42.51, 39.90, 39.71, 38.30, 38.28, 37.12, 36.80, 36.39, 36.01, 34.40, 32.16, 32.09, 32.04, 29.96, 29.93, 29.91, 29.76, 29.61, 29.53, 29.35, 29.28, 28.45, 28.23, 27.98, 27.96, 24.81, 24.50, 24.07, 23.05, 22.93, 22.78, 21.23, 19.52, 18.92, 14.37, 12.06.

MS (ESI) m/z 814.59 (MH)+; HRMS (ESI) m/z: Calcd (for $C_{51}H_{90}NO_6$, the 4° ammonium ion, 100%) 812.6768. found 812.6787

N,N-Dimethyl-N-[2-(tetradecanoyloxy),3-succinyloxy(4-cholesteryloxy)propyl]amine (V)

To a solution of 3-dimethylamino-2-hydroxypropylcholester-3-yl succinate (0.23 g, 0.39 mmoles) in 6 mL dichloromethane was added pyridine (0.046 g, 0.59 mmoles), myristoyl chloride (0.12 g, 0.39 mmoles) and a catalytic amount of DMAP at 0° C. The reaction was allowed to proceed from 0° C. to room temperature for 5 hours. The reaction mixture was extracted with chloroform (20 mL), washed with 5% sodium bicarbonate (4×10 mL) followed by brine solution (3×10 mL), dried over sodium sulfate. The chloroform solution was evaporated on a rotary evaporator and loaded on silica gel (230-400 mesh) and eluted with 0-0.4% methanol in chloroform to give the desired product (0.283 g, yield 85%).

$^1$H NMR (400 MHz, CDCl$_3$): δ 5.39-5.28 (m, 3H), 5.23-5.14 (m, 1H), 4.66-4.55 (m, 1H), 4.40-4.34 (m, 1H), 4.11 (dd, J=12.0, 6.4 Hz, 1H), 2.66-2.54 (m, 4H), 2.51-2.38 (m, 2H), 2.35-2.27 (m, 4H), 2.25 (s, 6H), 2.07-1.76 (m, 9H), 1.69-0.80 (m, 58H), 0.67 (s, 3H).

N,N-Dimethyl-N-[2-(9(Z)-octadecanoyloxy), 3-succinyloxy(4-cholesteryloxy)-propyl]amine (V)

To a solution of IV (178 mg, 0.3 mmol), pyridine (0.036 mL, 0.45 mmol) and DMAP (6 mg, 0.04 mmol), in CH$_2$Cl$_2$ (4 mL) at 0° C. was added dropwise oleoyl chloride (0.12 mL, 0.36 mmol). The reaction mixture was allowed to warm up slowly to room temperature. After stirring for 6 h at room temperature, the reaction mixture was diluted with CH$_2$Cl$_2$ (20 mL), washed sequentially with 5% aqueous sodium bicarbonate (10 mL), water (10 mL), and saturated aqueous NaCl (10 mL). The organic layer was dried (Na$_2$SO$_4$), filtered and concentrated in vacuo. Purification by column chromatography (SiO$_2$, elution with 0.2% MeOH in CHCl$_3$) furnished V (0.222 g, 87%) as a wax. NMR spectra coordinates are as follows: $^1$H NMR (CDCl$_3$): δ 5.39-5.28 (m, 3H), 5.23-5.14 (m, 1H), 4.66-4.55 (m, 1H), 4.40-4.34 (m, 1H), 4.11 (dd, J=12.0, 6.4 Hz, 1H), 2.66-2.54 (m, 4H), 2.51-2.38 (m, 2H), 2.35-2.27 (m, 4H), 2.25 (s, 6H), 2.07-1.76 (m, 9H), 1.69-0.80 (m, 58H), 0.67 (s, 3H).

N,N,N-Trimethyl-N-[2-(9(Z)-octadecanoyloxy),3-succinyloxy(4-cholesteryloxy)-propyl]ammonium iodide (DOTAP-Chol, 8)

In a 10 mL thick walled Pyrex reaction vessel with a stirrer bar, the intermediate V (0.10 g, 0.13 mmoles) was dissolved in 1 mL of chloroform:dimethylsulfoxide (1:1). To the solution was added methyl iodide (0.022 g, 0.16 mmoles). The reaction was carried out in a CEM Focused Microwave™ Synthesis system at 70° C., 150 W, 300 psi for 1 hour. The conversion was 100%. Chloroform was removed on a rotary evaporator and dimethylsulfoxide was removed under high vacuum. Silica gel column chromatographic purification of the resulting residue using 230-400 mesh silica gel size and 8-10% methanol in chloroform (v/v) as the eluent afforded the title compound as fluffy light yellowish white solid (0.099 g, yield 90%, R$_f$=0.5 in 20% methanol in chloroform) which on lyophilisation afforded the target compound in powder form.

$^1$H NMR (400 MHz, CDCl$_3$): (400 MHz, CDCl$_3$): δ $^1$H NMR (CDCl$_3$): δ 5.62-5.54 (m, 1H), 5.39-5.27 (m, 3H), 4.60-4.52 (m, 1H), 4.48 (dd, J=12.0, 4.0 Hz, 1H), 4.39 (d, J=13.2 Hz, 1H), 4.22 (dd, J=12.0, 4.4 Hz, 1H), 3.96 (dd, J=14.4, 9.2 Hz, 1H), 3.53 (s, 9H), 2.71-2.57 (m, 4H), 2.36 (dt, J=7.2, 3.6 Hz, 2H), 2.33-2.22 (m, 2H), 2.08-1.75 (m, 9H), 1.66-0.82 (m, 58H), 0.66 (s, 3H). $^{13}$C NMR (CDCl$_3$) δ 172.89, 172.23, 172.13, 139.68, 130.28, 129.88, 123.11, 74.87, 66.17, 65.89, 62.77, 56.87, 56.34, 54.95, 50.13, 42.52, 39.90, 39.72, 38.32, 38.29, 37.12, 36.81, 36.39, 36.02, 34.38, 32.13, 32.11, 32.05, 29.99, 29.96, 29.77, 29.55, 29.42, 29.36, 29.30, 28.45, 28.23, 27.98, 27.46, 27.42, 24.80, 24.50, 24.07, 23.05, 22.91, 22.78, 21.24, 19.52, 18.93, 14.37, 12.07.

MS (ESI) m/z: 867.46 (M$^+$); HRMS (ESI) m/z: Calcd (for C$_{55}$H$_{96}$NO$_6$, the 4° ammonium ion, 100%) 866.7238. found 866.7238.

An alternative procedure is as follows: a solution of V (175 mg, 2.0 mmol) and methyl iodide (0.0152 mL, 0.246 mmol) in CHCl$_3$ (1 mL) and DMSO (1 mL) was taken in a 10 mL glass tube covered with a plastic cap. The reaction mixture was subjected to 150 W microwave irradiation at 70° C. for 1 h. The reaction mixture was concentrated to dryness under high vacuum. Purification of this crude product by column chromatography (SiO$_2$, elution with 8% MeOH in CHCl$_3$) furnished 4 (219 mg, 90%) as a yellowish solid. NMR spectra coordinates are as follows: $^1$H NMR (CDCl$_3$): δ 5.62-5.54 (m, 1H), 5.39-5.27 (m, 3H), 4.60-4.52 (m, 1H), 4.48 (dd, J=12.0, 4.0 Hz, 1H), 4.39 (d, J=13.2 Hz, 1H), 4.22 (dd, J=12.0, 4.4 Hz, 1H), 3.96 (dd, J=14.4, 9.2 Hz, 1H), 3.53 (s, 9H), 2.71-2.57 (m, 4H), 2.36 (dt, J=7.2, 3.6 Hz, 2H), 2.33-2.22 (m, 2H), 2.08-1.75 (m, 9H), 1.66-0.82 (m, 58H), 0.66 (s, 3H). $^{13}$C NMR (CDCl$_3$) δ 172.89, 172.23, 172.13, 139.68, 130.28, 129.88, 123.11, 74.87, 66.17, 65.89, 62.77, 56.87, 56.34, 54.95, 50.13, 42.52, 39.90, 39.72, 38.32, 38.29, 37.12, 36.81, 36.39, 36.02, 34.38, 32.13, 32.11, 32.05, 29.99, 29.96, 29.77, 29.55, 29.42, 29.36, 29.30, 28.45, 28.23, 27.98, 27.46, 27.42, 24.80, 24.50, 24.07, 23.05, 22.91, 22.78, 21.24, 19.52, 18.93, 14.37, 12.07; MS (ESI) m/z 867.6 (M$^+$).

N,N-[Bis(2-tert-butyldiphenylsilyloxyethyl)]amine (VII)

To a solution containing a mixture of diethanolamine (1.095 g, 10.41 mmoles), triethylamine (2.57 g, 25.50 mmoles) and DMAP (0.127 g, 1.04 mmoles) in 30 mL dichloromethane was added tert-butyldiphenylchlorosilane (7.14 g, 26.02 mmoles), triethylamine (2.57 g, 25.50 mmoles) and DMAP (0.127 g, 1.04 mmoles) at 0° C. The reaction was carried out overnight from 0° C. to room temperature for 20 hours. The reaction mixture was transferred to a separatory funnel and the organic layer was washed successively with sodium bicarbonate, water and brine solution. The organic extract was dried over sodium sulfate and evaporated on a rotary evaporator. The residue was loaded on a silica gel (234-400 mesh size) and eluted with 1-2% methanol in chloroform to give an oily liquid (5.45 g, yield 90%, R$_f$=0.5 in 1% methanol in chloroform).

$^1$H NMR (400 MHz, CDCl$_3$): δ 7.74-7.67 (m, 8H), 7.48-7.34 (m, 12H), 3.81 (t, J=5.2 Hz, 4H), 2.81 (t, J=5.2 Hz, 4H), 1.065 (s, 18H).

Another batch of VII was prepared using the following procedure: to a solution of diethanol amine (1.0 mL, 10.42 mmol), Et$_3$N (3.56 mL, 25.52 mmol) and DMAP (127 mg, 1.04 mmol) in CH$_2$Cl$_2$ was added tert-butyldiphenylchlorosilane (6.75 mL, 26.05 mmol) dropwise at 0° C. The reaction mixture was allowed to warm to room temperature slowly. After stirring 20 h at room temperature the reaction mixture was diluted with CH$_2$Cl$_2$ (50 mL) and sequentially washed with 5% NaHCO$_3$ (30 mL), water (30 mL) and saturated aqueous NaCl (30 mL). The organic layer was dried (Na$_2$SO$_4$), filtered and concentrated in vacuo. Purification by column chromatography (SiO$_2$, elution with 2% methanol in CHCl$_3$) furnished VII (5.45 g, 90%) as oily liquid. NMR spectra coordinates are as follows: $^1$H NMR (CDCl$_3$): δ 7.74-7.67 (m, 8H), 7.48-7.34 (m, 12H), 3.81 (t, J=5.2 Hz, 4H), 2.81 (t, J=5.2 Hz, 4H), 1.065 (s, 18H).

3-[N,N-Bis(2-ter-butyldiphenylsilyloxyethyl)amino]-1-(Triphenylmethoxy)-2-propanol (VIII)

To a mixture (±)-(triphenylmethoxy)methyloxirane (0.65 g, 2.1 mmoles) and lithium perchlorate (0.5 g, 4.73 mmoles) in 10 mL absolute ethanol was added the amine VII (1.0 g, 1.72 mmoles). The reaction mixture was warmed to 65° C. and allowed to stir for 28 hours. The reaction solution was cooled to room temperature, transferred to a separatory funnel containing diethyl ether (25 mL) and washed with sodium bicarbonate, water and brine solution sequentially. The organic layer was dried over sodium sulfate and the residue was loaded on a silica gel (230-400 mesh). The compound was eluted with 0.5-2% methanol in chloroform to give an oily liquid (1.31 g, yield 85%, $R_f$~0.6 in 100% chloroform). $^1$H NMR (400 MHz, CDCl$_3$): 7.64-7.12 (m, 35H), 3.83-3.62 (m, 5H), 3.16-3.08 (m, 2H), 3.01 (dd, J=10.0, 5.2 Hz, 2H), 2.90-2.78 (m, 4H), 0.98 (s, 18H).

Another batch of VIII was prepared using the following procedure: to a solution of 12 (4.52 g, 7.78 mmol) and lithium perchlorate (2.27 g, 21.34 mmol) in ethanol (30 mL) was added (R)-(+)-trityl glycidyl ether (2.95 g, 9.33 mmol) at room temperature. The reaction mixture was stirred at 65° C. for 28 h, after which time it was cooled to room temperature, diluted with CH$_2$Cl$_2$ (100 mL) and washed with 5% NaHCO$_3$ (40 mL), and saturated aqueous NaCl (40 mL). The organic layer was dried (Na$_2$SO$_4$), filtered and concentrated in vacuo. Purification by column chromatography (SiO$_2$, elution with 0.5% methanol in CHCl$_3$) furnished 13 (6.48 g, 93%) as oily liquid. NMR spectra coordinates are as follows: $^1$H NMR (CDCl$_3$): δ 7.64-7.12 (m, 35H), 3.83-3.62 (m, 5H), 3.16-3.08 (m, 2H), 3.01 (dd, J=10.0, 5.2 Hz, 2H), 2.90-2.78 (m, 4H), 0.98 (s, 18H).

3[N,N-Bis(2-ter-butyldiphenylsilyloxyethyl)amino]-1-(Triphenylmethoxy)-2-(tetradecanoyloxy)propane (IX)

To a mixture of VIII (1.2 g, 1.3 mmoles), triethylamine (0.36 mL, 2.6 mmoles) and 4-dimethylaminopyridine (0.015 g, 0.13 mmoles) in 10 mL of dry dichloromethane at 0° C. was added myristoyl chloride (1.43 g, 1.43 mmoles) dropwise. The reaction was allowed to proceed from 0° C. to room temperature. The reaction mixture was diluted with chloroform, washed with 5% sodium bicarbonate, water and brine solution. The organic extract was dried over sodium sulfate; the residue was loaded on silica gel and eluted with 3% ethyl acetate in hexane to give 1.29 g of the compound (81% yield).

$^1$H NMR (400 MHz, CDCl$_3$): δ 7.34-7.05 (m, 35H), 5.05-4.96 (m, 1H), 3.53-3.42 (m, 4H), 3.08 (dd, J=10.0, 3.2 Hz, 1H), 2.99 (dd, J=10.0, 6.0 Hz, 1H), 2.68-2.54 (m, 6H), 2.25 (t, J=8.0 Hz, 2H), 1.64-1.55 (m, 2H), 1.35-1.14 (m, 20H), 0.98 (s, 18H), 0.88 (t, J=6.8 Hz, 3H).

Another batch of IX was prepared as follows: to a solution of VIII (1.60 g, 1.78 mmol), Et$_3$N (0.50 mL, 3.56 mmol) and DMAP (22 mg, 0.178 mmol), in CH$_2$Cl$_2$ (12 mL) was added dropwise myristoyl chloride (0.53 mL, 1.96 mmol) at 0° C. The reaction mixture was allowed to warm up slowly to room temperature. After stirring 24 h at room temperature, the reaction mixture was diluted with CH$_2$Cl$_2$ (50 mL), washed sequentially with 5% aqueous sodium bicarbonate (15 mL), water (15 mL), and saturated aqueous NaCl (15 mL). The organic layer was dried (Na$_2$SO$_4$), filtered and concentrated in vacuo. Purification by column chromatography (SiO$_2$, elution with 0.2% MeOH in CHCl$_3$) furnished 17 (1.60 g, 81%) as oily liquid. NMR spectra coordinates are as follows: $^1$H NMR (CDCl$_3$): δ 7.34-7.05 (m, 35H), 5.05-4.96 (m, 1H), 3.53-3.42 (m, 4H), 3.08 (dd, J=10.0, 3.2 Hz, 1H), 2.99 (dd, J=10.0, 6.0 Hz, 1H), 2.68-2.54 (m, 6H), 2.25 (t, J=8.0 Hz, 2H), 1.64-1.55 (m, 2H), 1.35-1.14 (m, 20H), 0.98 (s, 118H), 0.88 (t, J=6.8 Hz, 3H).

3-[N,N-Bis(2-ter-butyldiphenylsilyloxyethyl)amino]-2-(tetradecanoyloxy)-1-propanol (X)

To a mixture of the amine IX (0.948 g, 0.856 mmoles) in diethyl ether (1.2 mL) was added 85% formic acid (3.12 mL). The reaction mixture was stirred at room temperature for 20 hours. The reaction mixture was neutralized with sodium bicarbonate, diluted with diethyl ether (20 mL). The diethyl ether layer was subsequently washed with water and brine solution, dried over sodium sulfate, rotavapored on a rotary evaporator. The residue was eluted on a silica gel and eluted with 1-2% methanol in chloroform to give an oily liquid (0.4 g, yield 54%).

$^1$H NMR (400 MHz, CDCl$_3$): δ 7.65-7.24 (m, 20H), 4.08 (dd, J=11.2, 3.6 Hz, 1H), 3.95 (dd, J=11.2, 5.6 Hz, 1H), 3.84-3.56 (m, 5H), 2.83-2.58 (m, 6H), 2.31 (t, J=8.0 Hz, 2H), 1.68-1.50 (m, 2H), 1.36-1.16 (m, 20H), 1.02 (s, 18H), 0.88 (t, J=7.0 Hz, 3H).

Another batch of X was prepared as follows: to a solution of IX (1.55 g, 1.40 mmol) in diethyl ether (2 mL) was added 85% formic acid (5.2 mL) and the resulting reaction mixture was stirred at room temperature. After 20 h solid NaHCO$_3$ was added portion wise to neutralize the acidic solution. The reaction mixture was then diluted with diethyl ether (70 mL) and washed with water (20 mL) and saturated aqueous NaCl (20 mL). The organic layer was dried (Na$_2$SO$_4$), filtered and concentrated in vacuo. Purification by column chromatography (SiO$_2$, elution with 1% MeOH in CHCl$_3$) furnished 18 (0.77 g, 64%) as a oily liquid. NMR spectra coordinates are as follows: $^1$H NMR (CDCl$_3$): δ 7.65-7.24 (m, 20H), 4.08 (dd, J=11.2, 3.6 Hz, 1H), 3.95 (dd, J=11.2, 5.6 Hz, 1H), 3.84-3.56 (m, 5H), 2.83-2.58 (m, 6H), 2.31 (t, J=8.0 Hz, 2H), 1.68-1.50 (m, 2H), 1.36-1.16 (m, 20H), 1.02 (s, 18H), 0.88 (t, J=7.0 Hz, 3H).

3-[N,N-Bis(2-tert-butyldiphenylsilyloxyethyl)amino]-2-tetradecanoyloxy)-1-[succinyloxy(4-cholesteryloxy)]propane (XI)

Dicyclohexylcarbodiimide (0.2 g, mmoles) was added to a solution of the amine X (0.35 g, 0.4 mmoles) in 5 mL dry dichloromethane. The mixture was stirred at 0° C. and cholesterol hemisuccinic acid (0.39 g, 0.8 mmoles) dissolved in 2 mL dry dichloromethane was added slowly to the reaction mixture. The reaction was allowed to stir from 0° C. to room temperature for 6 h. The reaction mixture was diluted with chloroform washed with sodium bicarbonate followed by water and brine solution. The residue was loaded on silica gel (230-400 mesh) and eluted with 5-7% ethyl acetate in hexane to yield 0.42 mg of the compound (yield 79%).

$^1$H NMR (400 MHz, CDCl$_3$): δ $^1$H NMR (CDCl$_3$): δ 7.68-7.28 (m, 20H), 5.40-5.31 (m, 1H), 5.04-4.93 (m, 1H), 4.65-4.51 (m, 1H), 4.26 (dd, J=11.6, 2.4 Hz, 1H), 4.03 (dd, J=12.0, 6.0 Hz, 1H), 3.61 (t, J=6.0 Hz, 4H), 2.75-2.42 (m, 10H), 2.31 (d, J=7.2 Hz, 2H), 2.18 (t, J=7.6 Hz, 2H), 2.08-1.75 (m, 5H), 1.64-0.78 (m, 76H), 0.67 (s, 3H).

Another batch of XI was prepared as follows: to an ice cooled solution of X (0.52 g, 0.60 mmol) and cholesteryl hemisuccinate (0.44 g, 0.90 mmol) in DMF (5 mL) was added N,N'-dicyclohexylcarbodiimide (0.31 g, 1.5 mmol). After 5 min., the ice bath was removed and the solution was stirred for 6 h at room temperature. The resulting precipitation of dicyclohexylurea was removed by filtration. The filtrate was diluted with dichloromethane (30 mL) and washed with H$_2$O (10 mL), saturated aqueous NaCl (10 mL), dried (Na$_2$SO$_4$) and concentrated in vacuo. Purification by column chromatography (SiO$_2$, elution with 5% MeOH in CHCl$_3$ furnished XI (0.632 g, 79%) as wax. NMR spectra coordinates are as follows: $^1$H NMR (CDCl$_3$): δ 7.68-7.28 (m, 20H), 5.40-5.31 (m, 1H), 5.04-4.93 (m, 1H), 4.65-4.51 (m, 1H), 4.26 (dd, J=11.6, 2.4 Hz, 1H), 4.03 (dd, J=12.0, 6.0 Hz, 1H), 3.61 (t, J=6.0 Hz, 4H), 2.75-2.42 (m, 10H), 2.31 (d, J=7.2 Hz, 2H), 2.18 (t, J=7.6 Hz, 2H), 2.08-1.75 (m, 5H), 1.64-0.78 (m, 76H), 0.67 (s, 3H).

3-[N,N-Bis(2-hydroxyethyl)amino]-2-(tetradecanoyloxy)-1-[succinyloxy(4-cholesteryloxy)]propane (XII)

Tetra butyl ammonium fluoride trihydrate (0.37 g, 1.2 mmoles) was added to the amine (0.40 g, 0.3 mmoles) in THF (3 mL) at 0° C. The reaction was allowed to stir from 0° C. to room temperature overnight. The reaction mixture was diluted with chloroform and washed sequentially with saturated aqueous sodium bicarbonate, water and brine solution. The organic layer was dried over sodium sulfate, evaporated and the resulting residue was loaded on silica gel (230-400 mesh size) and eluted with 1.5% methanol in chloroform to give a waxy solid (0.15 g, 60% yield, R$_f$~0.5 in 10% methanol in chloroform).

$^1$H NMR (400 MHz, CDCl$_3$): δ 5.40-5.33 (m, 1H), 5.27-5.18 (m, 1H), 4.66-4.54 (m, 1H), 4.30 (dd, J=12.0, 3.6 Hz, 1H), 4.08 (dd, J=12.0, 5.6 Hz, 1H), 3.68-3.50 (m, 4H), 2.90 (brs, 2H), 2.81-2.48 (m, 10H), 2.42-2.22 (m, 4H), 2.04-1.75 (m, 5H), 1.70-0.77 (m, 58H), 0.66 (s, 3H).

Another batch of XII was prepared as follows: Tetrabutyl ammonium fluoride trihydrate (0.49 g, 1.55 mmol) was added to an ice-cooled solution of XI (0.52 g, 0.39 mmol) in THF (3 mL) under N$_2$ atmosphere. The reaction mixture was allowed to warm up to room temperature. After stirring overnight at room temperature, the reaction mixture was diluted with CH$_2$Cl$_2$ (20 mL) and sequentially washed with water (10 mL) and saturated aqueous NaCl (10 mL). The organic layer was dried, filtered and concentrated in vacuo. Purification by column chromatography (SiO$_2$, elution with 2% methanol in CHCl$_3$) furnished XII (231 mg, 69%) as a wax. NMR spectra coordinates are as follows: $^1$H NMR (CDCl$_3$): δ 5.40-5.33 (m, 1H), 5.27-5.18 (m, 1H), 4.66-4.54 (m, 1H), 4.30 (dd, J=12.0, 3.6 Hz, 1H), 4.08 (dd, J=12.0, 5.6 Hz, 1H), 3.68-3.50 (m, 4H), 2.90 (brs, 2H), 2.81-2.48 (m, 10H), 2.42-2.22 (m, 4H), 2.04-1.75 (m, 5H), 1.70-0.77 (m, 58H), 0.66 (s, 3H).

(N,N-[Bis(2-hydroxyethyl)]-N-methyl-N-[2-(tetradecanoyloxy)-1-[succinyloxy(4-cholesteryloxy)]ammonium iodide (Transfast-Chol, 9)

The dihydroxy compound (0.15 g, 0.18 mmoles) obtained in the previous step and methyl iodide (1 mL excess) were placed in a Pyrex glass tube. The reaction was carried out in a microwave synthesizer for 3 hours at 80° C., 150 W, 300 psi. The resulting oil was dissolved in dichloromethane and transferred to a round bottomed flask. The mixture was concentrated by rotary evaporation to ensure that all the residual iodomethane was removed. The crude product was passed through a silica gel (230-400 mesh size) and eluted with 8-10% methanol in chloroform to give (0.060 g, 40% yield).

(400 MHz, CDCl$_3$): δ 5.77-5.70 (m, 1H), 5.36 (d, J=5.2 Hz, 1H), 4.60-4.50 (m, 1H), 4.47 (dd, J=12.0, 3.6 Hz, 1H), 4.33-3.67 (m, 11H), 3.40 (s, 3H), 2.82-2.47 (m, 4H), 2.35 (t, J=7.6 Hz 2H), 2.31-2.22 (m, 2H), 2.06-1.92 (m, 2H), 1.90-1.76 (m, 3H), 1.64-0.82 (m, 58H) 0.67 (s, 3H); $^{13}$C NMR (CDCl$_3$) δ 173.64, 172.30, 172.05, 139.54, 123.20, 75.19, 66.28, 65.77, 65.48, 64.30, 63.33, 56.88, 56.34, 56.18, 56.12, 51.47, 50.15, 42.53, 39.93, 39.73, 38.25, 37.10, 36.80, 36.40, 36.02, 34.22, 32.17, 32.12, 32.06, 29.96, 29.92, 29.79, 29.61, 29.59, 29.36, 29.26, 28.45, 28.24, 27.98, 24.97, 24.51, 24.07, 23.05, 22.93, 22.79, 21.24, 19.51, 18.93, 14.37, 12.08

MS (ESI) m/z 873.60 (M$^+$); HRMS (LSIMS) m/z: Calcd (for C$_{53}$H$_{94}$NO$_8$, the 4° ammonium ion, 100%) 872.6979. found 872.6979.

Another batch of 9 was prepared as follows: a mixture of XII (167 mg, 0.19 mmol) and methyl iodide (2 mL) were placed in a 10 mL glass tube covered with a plastic cap. The reaction mixture was then subjected to 150 W microwave irradiation at 80° C. for 3.5 h. The reaction mixture was concentrated to dryness under high vacuum. Purification of this crude product by column chromatography (SiO$_2$, elution with 8% MeOH in CHCl$_3$) furnished 9 (62 mg, 33%) as yellowish solid. NMR spectra coordinates are as follows: $^1$H NMR (CDCl$_3$): δ 5.77-5.70 (m, 1H), 5.36 (d, J=5.2 Hz, 1H), 4.60-4.50 (m, 1H), 4.47 (dd, J=12.0, 3.6 Hz, 1H), 4.33-3.67 (m, 11H), 3.40 (s, 3H), 2.82-2.47 (m, 4H), 2.35 (t, J=7.6 Hz 2H), 2.31-2.22 (m, 2H), 2.06-1.92 (m, 2H), 1.90-1.76 (m, 3H), 1.64-0.82 (m, 58H) 0.67 (s, 3H); $^{13}$C NMR (CDCl$_3$) δ 173.64, 172.30, 172.05, 139.54, 123.20, 75.19, 66.28, 65.77, 65.48, 64.30, 63.33, 56.88, 56.34, 56.18, 56.12, 51.47, 50.15, 42.53, 39.93, 39.73, 38.25, 37.10, 36.80, 36.40, 36.02, 34.22, 32.17, 32.12, 32.06, 29.96, 29.92, 29.79, 29.61, 29.59, 29.36, 29.26, 28.45, 28.24, 27.98, 24.97, 24.51, 24.07, 23.05, 22.93, 22.79, 21.24, 19.51, 18.93, 14.37, 12.08; MS (ESI) m/z 873.6 (M$^+$).

[N,N-Bis(2-ter-butyldiphenylsilyloxyethyl)amino]-1,2-propanediol (XIII)

To a mixture of VIII (1.31 g, 1.46 mmoles) in diethyl ether (1.86 mL) was added 85% formic acid (5.43 mL). The reaction mixture was stirred at room temperature for 20 hours. The reaction mixture was neutralized with sodium bicarbonate, diluted with diethyl ether (40 mL). The diethyl ether layer was subsequently washed with water (15 mL) and brine solution, dried over sodium sulfate, rotavapored on a rotary evaporator. The residue was eluted on a silica gel and eluted with 1-2% methanol in CHCl$_3$ to give an oily liquid (0.54 g, yield 57%)

$^1$H NMR (CDCl$_3$): δ 7.70-7.61 (m, 8H), 7.49-7.31 (m, 12H), 3.73-3.55 (m, 6H), 4.397 (dd, J=11.6, 4.4 Hz, 1H), 2.78-2.54 (m, 5H), 2.57 (d, J=6.8 Hz, 1H) 1.02 (s, 18H).

Another batch of XIII was prepared using the following procedure: to a solution of VIII (2.0 g, 2.23 mmol) in diethyl ether (3 mL) was added 85% formic acid (8.2 mL) and the resulting reaction mixture was stirred at room temperature. After 20 h, solid NaHCO$_3$ was added portion wise to neutralize the acidic solution. The reaction mixture was then diluted with diethyl ether (80 mL) and sequentially washed with water (25 mL) and saturated aqueous NaCl (25 mL). The organic layer was dried (Na$_2$SO$_4$), filtered and concentrated in vacuo. Purification by column chromatography (SiO$_2$, elution with 4% MeOH in CHCl$_3$) furnished XIII (0.97 g, 67%) as oily liquid. NMR spectra coordinates are as follows: $^1$H NMR (CDCl$_3$): δ 7.70-7.61 (m, 8H), 7.49-7.31 (m, 12H), 3.73-3.55 (m, 6H), 4.397 (dd, J=11.6, 4.4 Hz, 1H), 2.78-2.54 (m, 5H), 2.57 (d, J=6.8 Hz, 1H) 1.02 (s, 18H).

(±)-3-[N,N-Bis(2-ter-butyldiphenylsilyloxyethyl)amino]-1,2-bis(tetradecanoyloxy)propane (XIV)

To a mixture of the diol XIII (0.61 g, 0.93 mmoles), triethylamine (0.33 mL, 2.34 mmoles) and 4-dimethylaminopyridine (0.012 g, 0.09 mmoles) in dry dichloromethane (5 mL) at 0° C. was added myristoyl chloride (0.56 g, 2.3 mmoles).

The reaction was allowed to stir from 0° C. to room temperature for 5 hours. Upon completion, the reaction mixture was diluted with dichloromethane, transferred to a separatory funnel and washed with saturated sodium bicarbonate, water and brine solution. The dichloromethane layer was dried over sodium sulfate and rotavapored on a rotary evaporator. The crude product obtained was purified by column chromatography on silica gel (2-3% ethyl acetate in hexane) to yield 0.450 g of the compound as a thick oily liquid (45% yield). $^1$H NMR (CDCl$_3$): δ 7.67-7.23 (m, 20H), 5.04-4.95 (m, 1H), 4.25 (dd, J=12.0, 2.8 Hz, 1H), 4.03 (dd, J=11.6, 5.6 Hz, 1H), 3.61 (t, J=8.0 Hz, 4H), 2.75-2.58 (m, 6H), 2.24-2.33 (m, 4H), 1.60-1.50 (m, 4H), 1.35-1.18 (m, 40H), 1.01 (s, 18H), 0.87 (t, J=6.4 Hz, 6H).

Another batch of XIV was prepared as follows: To a solution of XIII (0.65 g, 0.99 mmol), Et$_3$N (0.35 mL, 2.48 mmol) and DMAP (12 mg, 0.1 mmol), in CH$_2$Cl$_2$ (5 mL) at 0° C. was added dropwise myristoyl chloride (0.65 mL, 2.43 mmol). The reaction mixture was allowed to warm up slowly to room temperature. After stirring for 5 h at room temperature, the reaction mixture was diluted with CH$_2$Cl$_2$ (50 mL), washed sequentially with 5% aqueous sodium bicarbonate (15 mL), water (15 mL), and saturated aqueous NaCl (15 mL). The organic layer was dried (Na$_2$SO$_4$), filtered and concentrated in vacuo. Purification by column chromatography (SiO$_2$, elution with 2.5% EtOAc in Hexane) furnished XIV (0.50 g, 47%) as oily liquid. NMR spectra coordinates are as follows: $^1$H NMR (CDCl$_3$): δ 7.67-7.23 (m, 20H), 5.04-4.95 (m, 1H), 4.25 (dd, J=12.0, 2.8 Hz, 1H), 4.03 (dd, J=11.6, 5.6 Hz, 1H), 3.61 (t, J=8.0 Hz, 4H), 2.75-2.58 (m, 6H), 2.24-2.33 (m, 4H), 1.60-1.50 (m, 4H), 1.35-1.18 (m, 40H), 1.01 (s, 118H), 0.87 (t, J=6.4 Hz, 6H).

(±)-3-[N,N-Bis(2-hydroxyethyl)amino]-1,2-bis(tetradecanoyloxy)propane (XV)

To a solution of amine (0.3 g, 0.28 mmoles) obtained in the previous step in tetrahydrofuran (2 mL) was added tetrabutylammonium fluoride trihydrate (0.352 g, 1.17 mmoles) at 0° C. The reaction was allowed to proceed from 0° C. to room temperature overnight. The reaction mixture was diluted with chloroform, washed with saturated sodium bicarbonate followed by water and brine solution. The organic layer was dried over sodium sulfate and rotavapored on a rotary evaporator. The residue was loaded on silica gel (230-400 mesh) and the desired compound was eluted with 2-3% methanol in chloroform to give a waxy solid (0.120 g, 72.5% yield). $^1$H NMR (CDCl$_3$): δ 5.24-5.14 (m, 1H), 4.35 (dd, J=12.0, 3.2 Hz, 1H), 4.10 (dd, J=12.4, 6.4 Hz, 1H), 3.60 (t, J=5.2 Hz, 4H), 2.77-2.66 (m, 6H), 2.38-2.26 (m, 4H), 1.66-1.54 (m, 4H), 1.36-1.18 (m, 40H), 0.87 (t, J=6.0 Hz, 6H).

Another batch of XV was prepared as follows: tetrabutyl ammonium fluoride trihydrate (0.50 g, 1.60 mmol) was added to an ice-cooled solution of XIV (0.43 g, 0.40 mmol) in THF (3 mL) under N$_2$ atmosphere. The reaction mixture was allowed to warm up to room temperature. After stirring overnight at room temperature, the reaction mixture was diluted with CH$_2$Cl$_2$ (30 mL) and sequentially washed with 5% NaHCO$_3$ (10 mL), water (10 mL) and saturated aqueous NaCl (10 mL). The organic layer was dried (Na$_2$SO$_4$), filtered and concentrated in vacuo. Purification by column chromatography (SiO$_2$, elution with 2% methanol in CHCl$_3$) furnished XV (172 mg, 72%) as a wax. NMR spectra coordinates are as follows: $^1$H NMR (CDCl$_3$): δ 5.24-5.14 (m, 1H), 4.35 (dd, J=12.0, 3.2 Hz, 1H), 4.10 (dd, J=12.4, 6.4 Hz, 1H), 3.60 (t, J=5.2 Hz, 4H), 2.77-2.66 (m, 6H), 2.38-2.26 (m, 4H), 1.66-1.54 (m, 4H), 1.36-1.18 (m, 40H), 0.87 (t, J=6.0 Hz, 6H).

(±)-N,N-[Bis(2-hydroxyethyl)]-N-methyl-N-[2,3-bis-tetradecanoyloxy)propyl]ammonium iodide (Transfast, 10)

The diol (0.1 g, 0.17 mmoles) obtained in the previous step and methyl iodide (excess, ~1 mL) was taken in a 10 mL thick walled pyrex glass tube. The reaction was carried out in a microwave synthesizer at 80 C, 150 W, 300 psi for 3 hours. The resulting oil was diluted with dichloromethane and rotavapored on a rotary evaporator to drive away the excess iodomethane. The resulting residue was loaded on silica gel column (230-400 mesh size) and eluted with 5-10% methanol in chloroform to give a white solid (0.18 g, 81% yield).

$^1$H NMR (400 MHz, CDCl$_3$): δ 5.73-5.64 (m, 1H), 4.47 (dd, J=12.0, 3.6 Hz, 1H), 4.32-3.74 (m, 11H), 3.37 (s, 3H), 2.42-2.30 (m, 4H), 1.66-1.53 (m, 4H), 1.37-1.18 (m, 40H), 0.87 (t, J=6.8 Hz, 6H)

MS (ESI) m/z 615.11 (MH$^+$); HRMS (LSIMS) m/z: Calcd (for C$_{36}$H$_{72}$NO$_6$, the 4° ammonium ion, 100%) 614.5360. found 614.5369.

Another batch of 10 was prepared as follows: a mixture of XV (122 mg, 0.2 mmol) and methyl iodide (1.5 mL) were taken in a 10 mL glass tube covered with a plastic cap. The reaction mixture was then subjected to 150 W microwave irradiation at 80° C. for 3.5 h. The reaction mixture was concentrated to dryness under high vacuum. Purification of this crude product by column chromatography (SiO$_2$, elution with 8% MeOH in CHCl$_3$) furnished 10 (120 mg, 81%) as a yellowish solid. NMR spectra coordinates are as follows: $^1$H NMR (CDCl$_3$): δ 5.73-5.64 (m, 1H), 4.47 (dd, J=12.0, 3.6 Hz, 1H), 4.32-3.74 (m, 11H), 3.37 (s, 3H), 2.42-2.30 (m, 4H), 1.66-1.53 (m, 4H), 1.37-1.18 (m, 40H), 0.87 (t, J=6.8 Hz, 6H); $^{13}$C NMR (CDCl$_3$) δ 173.60, 173.10, 65.84, 65.72, 65.18, 64.48, 63.54, 56.08, 56.03, 51.51, 34.52, 34.25, 32.16, 29.95, 29.91, 29.78, 29.75, 29.61, 29.54, 29.38, 29.34, 24.99, 24.91, 22.93, 14.37; MS (ESI) m/z 615.2 (M$^+$).

N,N-di-n-tetradecylamine (XVII)

1-Bromotetradecane (0.5 g, 1.80 moles), tertadecan-1-amine (0.38 g, 1.80 mmoles) and potassium carbonate (0.274 g, 1.98 mmoles) were placed in a 10 mL thick walled Pyrex glass and 1:1 mL of dimethylsulfoxide and chloroform was added. The reaction was carried out at 80° C., 150 W, 300 psi, 3 hours in a microwave synthesizer. Dimethylsulfoxide was removed under vacuum and the compound was eluted with 2-4% methanol in chloroform to give the compound as a white solid (0.3 g, 30% yield).

$^1$H-NMR of N,N-Di-n-tetradecylamine: (400 MHz, CDCl$_3$) δ/ppm: 0.9 [t, 6H, CH$_3$—(CH$_2$)$_9$—]; 1.15-1.45 [m, 18H, CH$_3$—(CH$_2$)$_{11}$]; 1.45-1.7 [m, 4H, NH(CH$_2$—CH$_2$—)$_2$—]; 2.55-2.7 [t, 4H NH(CH$_2$—CH$_2$—)$_2$], 4.0-4.7 [broad peak, NH]. MS (ESI) m/z 411.23 (MH+1)

N,N-di-n-tetradecyl-N,N-dihyroxyethylammonium chloride (11, DTDEAC)

To the tertiary amine (0.3 g, 0.7 mmoles) obtained in the previous step was added 2-chloroethanol (excess) and sodium hydroxide (5.6 mmoles, 0.16 g) dissolved in 0.5 mL water. The reaction was carried out at 80° C., 150 W, 300 psi for 3 hours in a microwave synthesizer. The 2-chloroethanol was removed on a rotary evaporator by repeated chasing with methanol. The residue was loaded on silica gel (230-400 mesh size) and eluted with 10% methanol in chloroform to give a white solid (0.162 g, 45% yield).

$^1$H-NMR of N,N-di-n-tetradecyl-N,N-dihydroxyethylammonium chloride (400 MHz, CDCl$_3$): δ/ppm=0.9 [t, 6H, CH$_3$—(CH$_2$)$_n$—]; 1.20-1.5 [m, 44H, —(CH$_2$)$_{11}$—]; 1.55-1.9 [m, 4H, (HOCH$_2$—CH$_2$)$_2$N$^+$(CH$_2$—CH$_2$—)$_2$]; 3.3-3.5 [m, 4H, (OHCH$_2$—CH$_2$)$_2$N$^+$(CH$_2$—CH$_2$—)$_2$]; 3.55-3.85 [m, 4H, (OHCH$_2$—CH$_2$)$_2$N$^+$(CH$_2$—CH$_2$—)$_2$]; 3.95-4.2 [m, 4H, (OHCH$_2$—CH$_2$)$_2$N$^+$(CH$_2$—CH$_2$—)$_2$]; 5.20-5.45 [m, 2H, —OH].

MS (ESI) m/z 499.23 (MH)$^+$; HRMS (LSIMS) m/z: Calcd (for C$_{42}$H$_{84}$NO$_4$, the 4° ammonium ion, 100%) 498.5245. found, 498.5241

Synthesis of N,N,N-Trimethyl-N-[2-hydroxy, 3-succinyloxy(4-cholesteryloxy)-propyl]ammonium iodide (HCSTAP, 12)

3-dimethylamino-2-hydroxypropyl cholester-3-yl succinate (IV, 0.1 g, 0.17 mmoles) and MeI (0.029 g, 0.20 mmoles) were dissolved in 1 mL of chloroform:dimethylsulfoxide (1:1) in a 10 mL thick walled Pyrex glass. The reaction was carried out at 70 C, 150 W, 300 psi in a microwave synthesizer for 1 hour. Chloroform was removed on a rotary evaporator and the dimethylsulfoxide was removed under vacuum pump. The resulting residue was loaded on silica gel (230-400 mesh) and eluted with 10% methanol in chloroform to obtain a fluffy white solid (0.096 g, 94% yield, R$_f$=0.2 in 10% methanol in chloroform).

$^1$H NMR (400 MHz, CDCl$_3$): δ/ppm=0.6-2.40 [(m, 43H, cholesteryl skeleton); 2.60 [t, 4H, Chol-OCO—CH$_2$—CH$_2$—OCO—CH$_2$—CH(OH)—CH$_2$(N$^+$(CH$_3$)$_3$)]; 3.50 [s, 9H, Chol-OCO—CH$_2$—CH$_2$—OCO—CH$_2$—CH(OH)—CH$_2$(N$^+$(CH$_3$)$_3$)]; 3.60 [m, 1H, Chol-OCO—CH$_2$—CH$_2$—OCO—CH$_2$—CH(OH)—CH$^1$H$^2$(N$^+$(CH$_3$)$_3$)]; 3.80 [m, 1H, Chol-OCO—CH$_2$—CH$_2$—OCO—CH$_2$—CH(OH)—CH$^1$H$^2$(N$^+$(CH$_3$)$_3$)]; 4.20-4.30 [(m, 2H, Chol-OCO—CH$_2$—CH$_2$—OCO—CH$_2$—CH(OH)—CH$^1$H$^2$(N$^+$(CH$_3$)$_3$]; 4.50 [m, 1H, H$_{3α}$ (Chol)]; 4.70 [m, 1H, Chol-OCO—CH$_2$—CH$_2$—OCO—CH$_2$—CH(OH)—CH$^1$H$^2$(N$^+$(CH$_3$)$_3$)]; 5.30-5.40 [m, 1H, H$_6$ (Chol)];

MS (ESI) m/z 603.39 (MH$^+$); HRMS (LSIMS) m/z: Calcd (for C$_{37}$H$_{64}$NO$_5$, the 4° ammonium ion, 100%) 602.4784. found 602.4716.

Synthesis of 3β[N—(N',N'-dimethylaminoethane)-carbamoyl]cholesterol (DC-Chol) (XVII)

Cholesteryl chloroformate (3 g, 6.7 mmoles) in 5 mL dry dichloromethane was added dropwise to a solution of N,N-dimethylethylene diamine (24 mmoles) in 4 mL dry dichloromethane at 0° C. The reaction was allowed to stir overnight. The solvent was then evaporated on a rotary evaporator and the residue was purified by recrystallisation from absolute ethanol to give a white solid (0.84 g, 25% yield, R$_f$=0.5 in 30% methanol in chloroform).

$^1$H NMR (400 MHz, CDCl$_3$): δ/ppm=0.6-2.40 [(m, 43H, cholesteryl skeleton); (s, 9H, Chol-OCO—NH—(CH$_2$)$_2$N(CH$_3$)$_2$)]; 3.10 [s, 2H, Chol-OCONH—CH$_2$—CH$_2$—N(CH$_3$)$_2$]; 4.5 [m, 1H, H$_{3α}$ (Chol)]; 5.2 [(m, 1H, Chol-OCO—NH—CH$_2$—CH$_2$—N(CH$_3$)]; 4.60 [m, 1H, H$_{3α}$ (Chol)]; 5.30-5.40 [d, 1H, H$_6$ (Chol)]

MS (ESI) m/z 501.50 (MH)$^+$

Synthesis of 3β[N—(N',N',N'-trimethylaminopropane)-carbamoyl]cholesterol iodide (TC-Chol, 13)

DC-Chol (0.100 g, 0.2 mmoles) and methyl iodide (0.034 g, 0.24 mmoles) were dissolved in 1 mL of CHCl$_3$:DMSO (1:1). The reaction was carried out by microwave irradiation at 150 watts, 70° C. for 1 hour. The solvent was removed on vacuum pump and loaded on silica gel. The compound was eluted with 8-10% methanol in CHCl$_3$ to give the title compound as a yellowish fluffy solid (0.098 g, 96% yield, R$_f$=0.4 in 30% methanol in chloroform).

$^1$H NMR (400 MHz, CDCl$_3$): δ/ppm=0.6-2.40 [(m, 43H, cholesteryl skeleton); 3.50 [s, 9H, (Chol-CONHCH$_2$—CH$_2$(N$^+$(CH$_3$)$_3$)]; 3.80 [m, 2H, (Chol-CONHCH$_2$—CH$_2$(N$^+$(CH$_3$)$_3$)]; 3.90 [t, 2H, (Chol-CONHCH$_2$—CH$_2$(N$^+$(CH$_3$)$_3$)]; 4.50 [m, 1H, H$_{3α}$ (Chol)]; 5.30 [d, 1H, H$_6$ (Chol)], 6.05 [bs, 1H, (Chol-CONHCH$_2$—CH$_2$(N$^+$(CH$_3$)$_3$)]

MS (ESI) m/z 516.03 (MH$^+$); HRMS (LSIMS) m/z: Calcd (for C$_{33}$H$_{59}$N$_2$O$_2$, the 4° ammonium ion, 100%) 515.4577. found 515.4545.

Synthesis of 3β[N—(N',N'-dimethyl,N'-ethylaminopropane)-carbamoyl]cholesterol iodide (DEC-Chol, 14)

DC-Chol (0.100 g, 0.2 mmoles) and 2-iodoethane (0.037 g, 0.24 mmoles) were dissolved in 1 mL of CHCl$_3$:DMSO (1:1). The reaction was carried out by microwave irradiation at 150 watts, 70° C. for 1 hour. The solvent was removed on vacuum pump and loaded on silica gel. The compound was eluted with 10% methanol in CHCl$_3$ to give the title compound as a yellowish fluffy solid (0.099 g, 94% yield, R$_f$=0.4 in 30% methanol in chloroform).

$^1$H NMR (400 MHz, CDCl$_3$): δ/ppm=0.6-2.40 [(m, 43H, cholesteryl skeleton); 3.10 [s, 6H, (Chol-CONHCH$_2$—CH$_2$(N$^+$(CH$_3$)$_2$)]; 3.40 [s, 2H, (Chol-CONHCH$_2$—CH$_2$(N$^+$(CH$_2$CH$_3$))]; 3.70 [m, 2H, (Chol-CONHCH$_2$—CH$_2$(N$^+$(CH$_3$)$_2$C$_2$H$_5$)]; 3.90 [t, 2H, (Chol-CONHCH$_2$—CH$_2$(N$^+$(CH$_3$)$_2$C$_2$H$_5$)]; 4.40 [m, 1H, H$_{3α}$ (Chol)]; 5.40 [d, 1H, H$_6$ (Chol)].

MS (ESI) m/z 529.5869 (M$^+$); HRMS (LSIMS) m/z: Calcd (for C$_{34}$H$_{61}$N$_2$O$_2$, the 4° ammonium ion, 100%) 529.4729. found 529.4609

Synthesis of Cholesteryl-3β-N-[2-[N'-(2-hydroxyethyl)-N'N'-(dimethylammonio)ethyl]carbamate bromide (HDC-Chol, 15)

DC-Chol (0.2 g, 0.4 mmoles) and 2-Bromoethanol (0.05 g, 0.4 mmoles) were placed in a 10 mL thick walled pyrex reaction vessel with a stirrer bar. The reactants were dissolved in 1 mL of chloroform:dimethylformamide (1:1). The reaction was carried out at 80° C., 150 W, 300 psi for 3 hours in a microwave synthesizer. Chloroform was removed on a rotary evaporator and dimethylformamide was removed under high vacuum. Silica gel column chromatographic purification of the resulting residue using 230-400 mesh silica gel size and 10-11% methanol in chloroform (v/v) as the eluent afforded the title compound as a white solid (0.166 g, yield 76%, R$_f$=0.3 in 20% methanol in chloroform).

$^1$H NMR (400 MHz, CDCl$_3$): δ/ppm=0.6-2.40 [(m, 43H, cholesteryl skeleton)]; 3.30 [s, 6H, (Chol-CONHCH$_2$—CH$_2$(N$^+$(CH$_3$)$_2$)]; 3.60-3.82 [m, 6H, OHCH$_2$—CH$_2$—N$^+$(CH$_3$)$_2$—, —O(CO)—NH—CH$_2$—CH$_2$—N$^+$(CH$_3$)$_2$]; 4.1-4.2 [m, 2H, OHCH$_2$CH$_2$—N$^+$(CH$_3$)$_2$ 4.45 [m, 1H, H$_{3α}$ (Chol)]; 5.30 [d, 1H, H$_6$ (Chol)].

MS (ESI) m/z 546.20 (MH$^+$); HRMS (LSIMS) m/z: Calcd (for C$_{34}$H$_{61}$N$_2$O$_3$, the 4° ammonium ion, 100%) 545.4682. found 545.4560.

Synthesis of Cholesteryl-3β-N[2-[N'-(11-hydroxyundecyl)N'—N'(dimethylammonio)ethyl]carbamate bromide (HUDC-Chol, 6)

DC-Chol (0.2 g, 0.4 mmoles) and 11-bromo-1-undecanol (0.11 g, 0.44 mmoles) were placed in a 10 mL thick walled pyrex reaction vessel with a stirrer bar. The reactants were dissolved in 1 mL of chloroform:dimethylformamide (1.5:1). The reaction was carried out at 80° C., 150 W, 300 psi for 3 hours in a microwave synthesizer. Chloroform was removed on a rotary evaporator and dimethylformamide was removed under high vacuum. Silica gel column chromatographic purification of the resulting residue using 230-400 mesh silica gel size and 6-8% methanol in chloroform (v/v) as the eluent afforded the title compound as a white solid (0.132 g, yield 49%, $R_f$=0.4 in 20% methanol in chloroform).

$^1$H NMR (400 MHz, CDCl$_3$): δ/ppm=0.6-2.40 [(m, 43H, cholesteryl skeleton), 18H, —OHCH$_2$(CH$_2$)$_9$—CH$_2$—N$^+$(CH$_3$)$_2$—]; 3.30 [s, 6H, (Chol-CON-HCH$_2$—CH$_2$(N$^+$(CH$_3$)$_2$)]; 3.50 [(t, 2H, —O(CO)—NH—CH$_2$—CH$_2$—N$^+$(CH$_3$)2]; 3.60 [t, 2H, OHCH$_2$(CH$_2$)$_9$—CH$_2$—N$^+$(CH$_3$)$_2$—]; 3.65-3.79 [m, 4H, OHCH$_2$(CH$_2$)$_9$—CH$_2$—N$^+$(CH$_3$)$_2$; —O(CO)—NH—CH$_2$—CH$_2$—N$^+$(CH$_3$)$_2$]; 4.45 [m, 1H, H$_{3α}$ (Chol)]; 5.30 [d, 1H, H$_6$ (Chol)].

MS (ESI) m/z 672.1 (M$^+$); HRMS (LSIMS) m/z: Calcd. (for C$_{43}$H$_{79}$NO$_3$, the 4° ammonium ion, 100%) 671.6018. found 671.6091

EXAMPLE 2

Methods and Compositions for Determining Non-Toxicity of Lipids for Transfecting Eukaryotic Cells The following example describes methods and compositions for determining the non-toxicity of the lipids of the invention for introducing a therapeutic agent into eukaryotic cells.

Briefly, in a first experiment, the ability of eukaryotic cells to survive exposure to various lipids at doses of 20 and 50 μg/ml was examined. Fl83B cells were plated on 96-well plate for 24 hours. Typically liposomes were added to well and incubated at 37° C. for 24 hours. Thereafter, Cell Titer-Blue Reagent (resazurin) was added and incubated for 4 hours. Resazurin was used as indicator to measure the metabolic capacity of cells. Viable cells retain the ability to reduce resazurin into resorufin, which is highly fluorescent. Nonviable cells rapidly lose metabolic capacity and do not reduce the indicator dye, and thus do not generate a fluorescent signal. The fluorescence in each well was measured by fluorescent reader.

Figure 10:
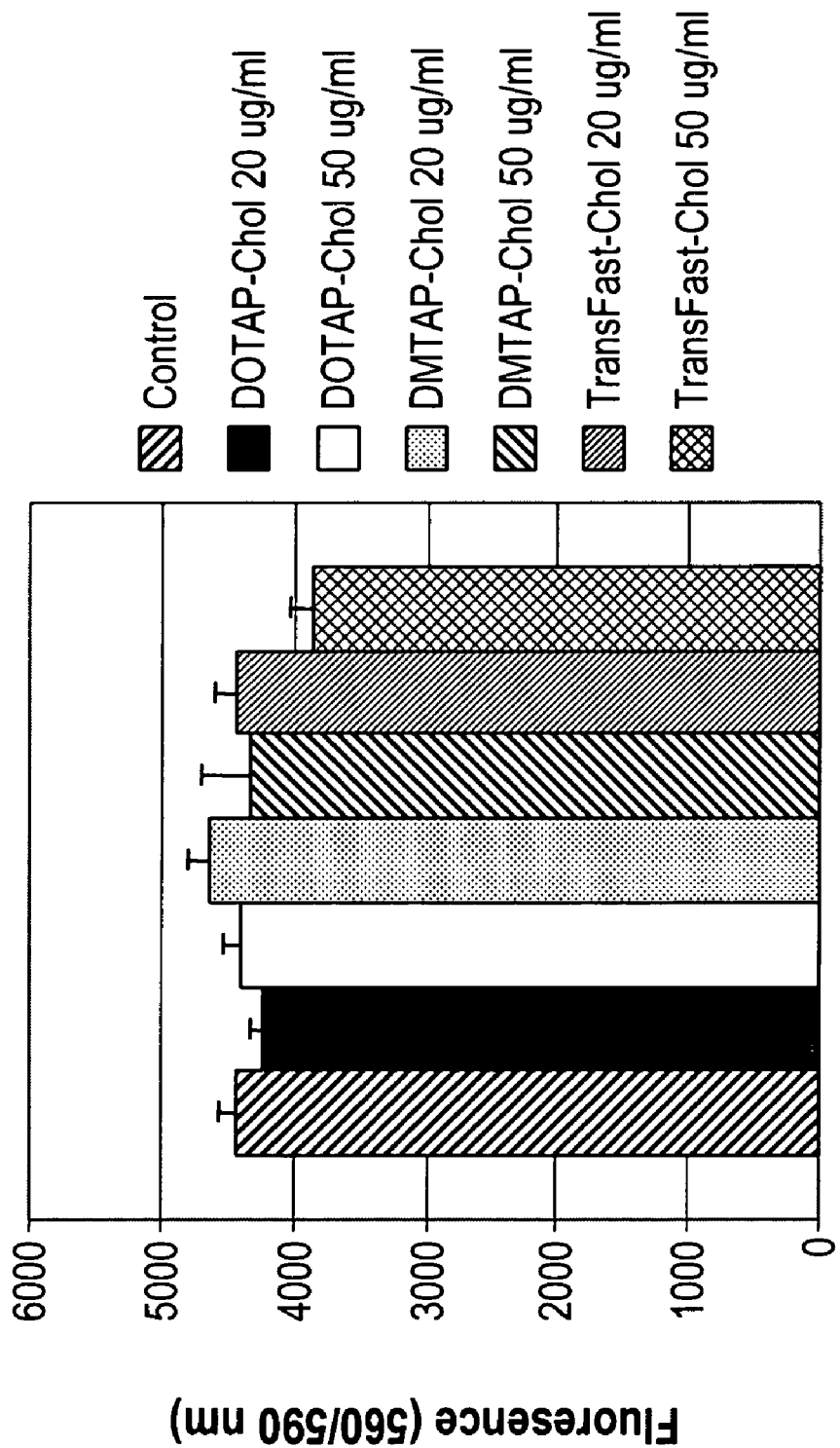
FIG. 10 shows a histogram showing that the lipids of the invention that are suitable for the high efficiency transfer of a therapeutic agent are non-toxic when used on mammalian cells at doses of 20 and 50 µg/ml.

As compared to a control, no greater than a 10% change in cell survival was detected (see FIG. 10).

In a second experiment, FL83B and HeLa cells were plated on 96 well plate 18 hours prior to transfection. Then, liposome was added to each well and incubated for 24 hours. Thereafter, Cell Titer 96® AQ$_{ueous}$ One Solution Reagent was added and incubated for 4 hours. The MTS tetrazolium compound (Owen's reagent) is bioreduced by viable cells into a colored formazan product that is soluble in tissue culture compound. The absorbance of the formazan was measured at 490 nm with a 96 well plate reader.

Figure 13:
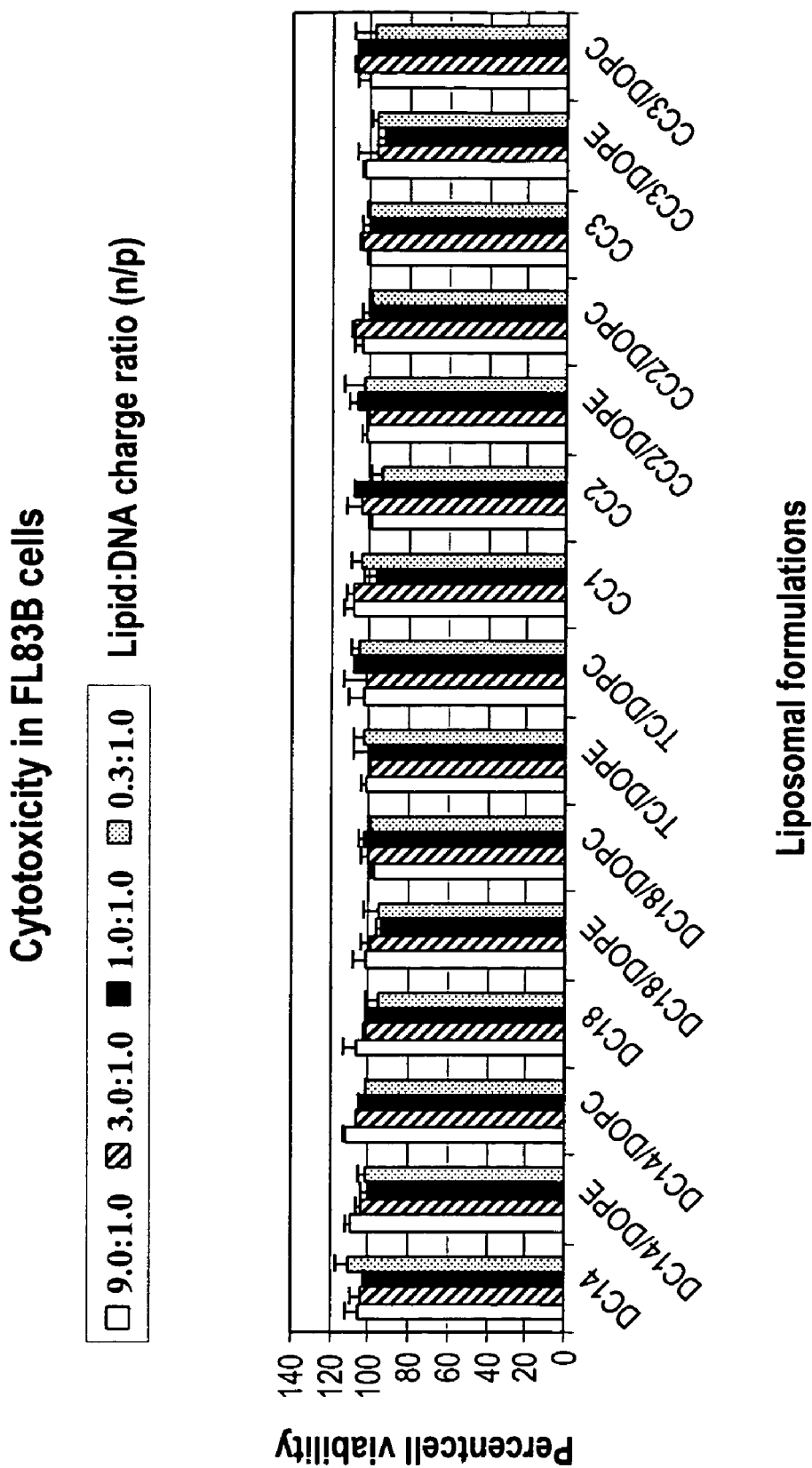
FIGS. 13 and 14 show histograms indicating that the lipid:DNA charge ratios of the complexes of the invention are non-toxic in eukaryotic cells, respectively, FL83B cells and HeLa cells, at lipid:DNA charge ratios (n/p) ranging from 9.0:1.0 to 0.3:1.0.
Figure 14:
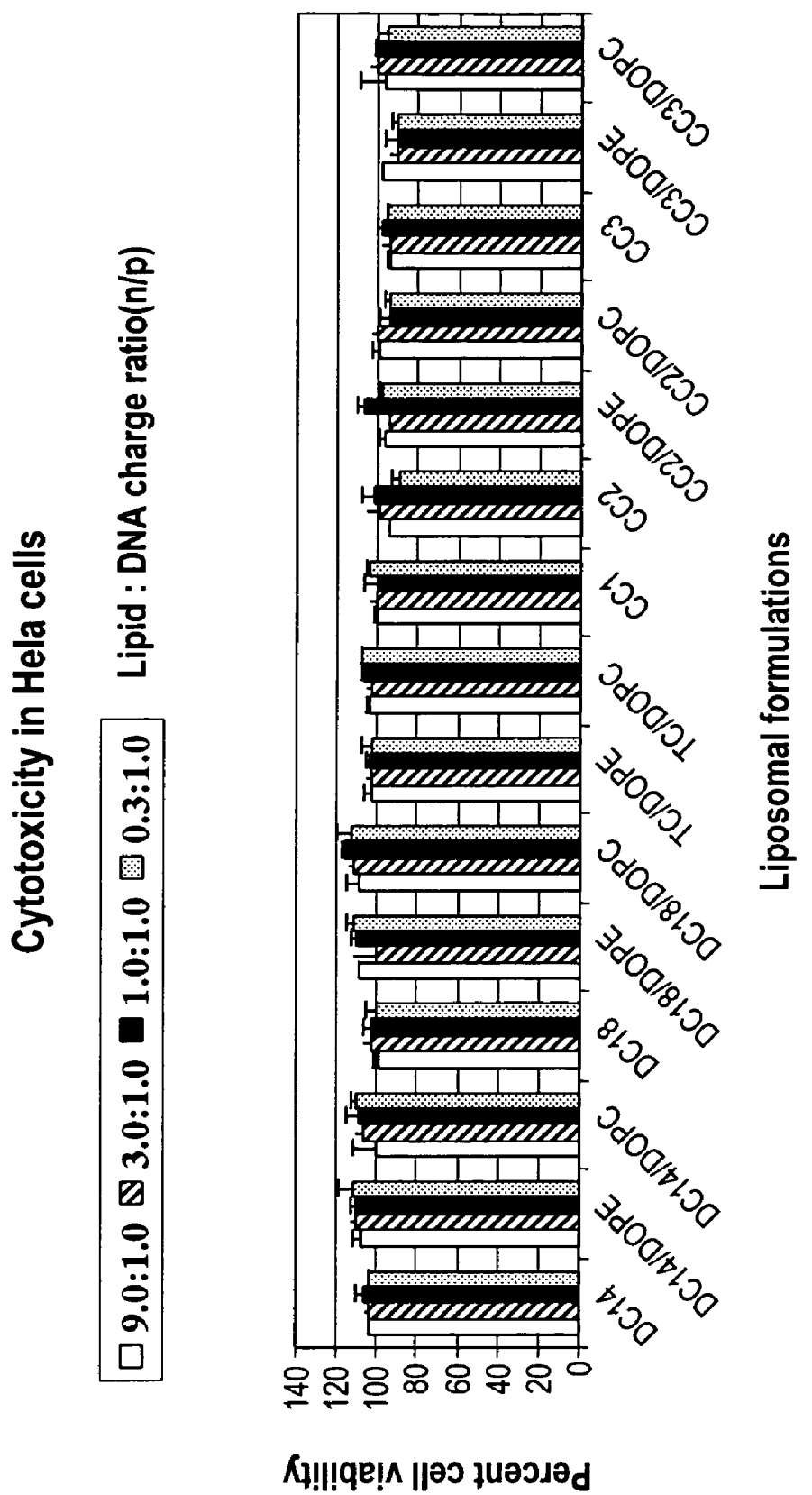

As compared to a control, the cytotoxicity data indicates that the liposomal formulations of DMTAP-Chol (labeled as DC14) and DOTAP-Chol (labeled as DC18) when used alone or in combination with DOPE and DOPC as co-lipid are non-toxic in representative HeLa and FL83B cells. Similarly the cholesterol backbone containing cationic lipids labeled as CC1 when used in combination with DOPE as co-lipid were non-toxic. In addition, the two other cholesterol backbone containing cationic lipids, labeled as CC2 and CC3, when used alone or in combination with DOPE and DOPC as co-lipid, were found to be non-toxic in representative HeLa and FL83B cells (see FIGS. 13 and 14).

Accordingly, these data indicate that the lipids of the invention, either alone or in combination, are non-toxic to eukaryotic cells as tested.

EXAMPLE 3

Methods and Compositions for Determining Lipid Compositions and Ratios for Optimal Transfection of Eukaryotic Cells The following example describes methods and compositions for determining lipid compositions for efficient delivery of therapeutic agents into eukaryotic cells.

Briefly, the efficacy of various lipid formulations were tested in three cell lines A-549, FL83B and HeLa cells and the transfection efficiencies of the cationic liposomal formulations were compared with a commercially available transfection reagent (e.g., Lipofectamine 2000).

The transfection efficiency of lipid 7 (the cholesterol analog of DMTAP, labeled as DC14) when used alone and in combination with DOPE and DOPC was found to be comparable to the transfection efficiency of Lipofectamine 2000 in A-549 and FL83B cells over a lipid:DNA charge ratio of 9.0:1 to 0.3:1. The transfection efficiency in HeLa cells is more than one fold less than Lipofectamine 2000 over the same range of lipid:DNA charge ratio.

The transfection efficiency of lipid 8 (the cholesterol analog of DOTAP, labeled as DC18) when used alone at lipid:DNA charge ratios of 1:1 and 0.3:1 was one fold less than that of Lipofectamine 2000 in FL83B cells and A-549 cells, while in HeLa cells the efficiency is almost 1.5 fold less at the same charge ratios. Lipid 8 in combination with DOPE at higher charge ratio of 3:1 is comparable to Lipofectamine 2000 in A-549 cells, while in FL83B and HeLa cells the transfection efficiency is more than 1.5 fold less than Lipofectamine 2000. The transfection efficiency of lipid 8 in combination with DOPC was comparable to Lipofectamine 2000 at a charge ratio of 1.1 in HeLa cells, in FL83B over the charge ratio of 9.0:1.0 to 0.3:1.0, its about two fold less while in A-549 is about 1 fold less than Lipofectamine 2000. From the transfection data the lipid 7 and 8 alone without any co-lipids is about as efficient as that of the lipids in combination with DOPE and DOPC.

Lipid 9 (labeled as TC) when used in combination with DOPE and DOPC had comparable transfection efficiency to that of Lipofectamine 2000 in A549 cells. The transfection of the lipid 9 in combination with DOPE and DOPC in HeLa cells and FL83B cells is about a little more than 1 fold less than lipofectamine 2000.

The transfection efficiency of the cholesterol backbone containing cationic lipid CHSTAP (lipid 12) was comparable to Lipofectamine 2000 in all the three cell lines at a lipid:DNA charge ratio of 0.3:1.

Lipid 14 (labeled as CC2) alone at a charge ratio of 3:1 and in combination with DOPE at a charge ratio of 9:1 is comparable to the transfection efficiency of Lipofectamine 2000, while in combination with DOPC was less efficient in FL83B cells. The transfection of lipid CC2 at lower lipid:DNA charge ratios of 1:1 and 0.3:1 alone or in combination with DOPE and DOPC is less than Lipofectamine 2000 by about 1.5 fold in A549 cells. In HeLa cells the transfection efficiency of CC2 in combination with DOPC at a lipid:DNA charge ratio of 0.3:1 is almost comparable to Lipofectamine 2000, whereas in combination with DOPE the transfection efficiency is 2.5 fold less and the lipid alone over the whole charge ratio of 9:1 to 3:1 is more than 1.5 fold less.

Figure 15:
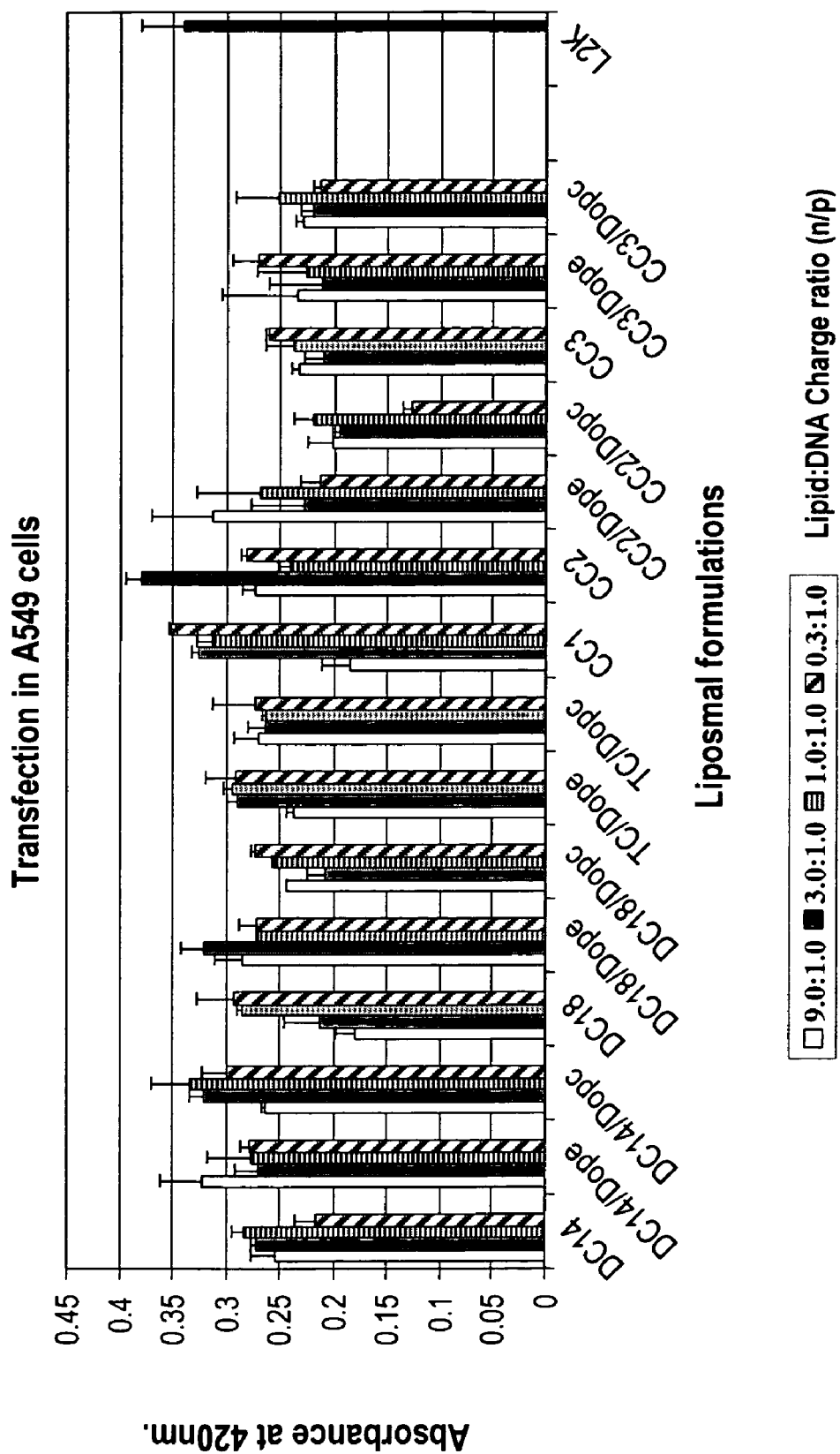
FIGS. 15, 16, and 17 show histograms indicating the transfection efficiency of a β-Gal encoding test plasmid into eukaryotic cells (i.e., A549 cells, FL83B cells, and HeLa cells) using certain lipids and mixed lipids of the invention as compared to a control and as a function of the lipid:DNA charge ratios (n/p) of the transfection complex.
Figure 16:
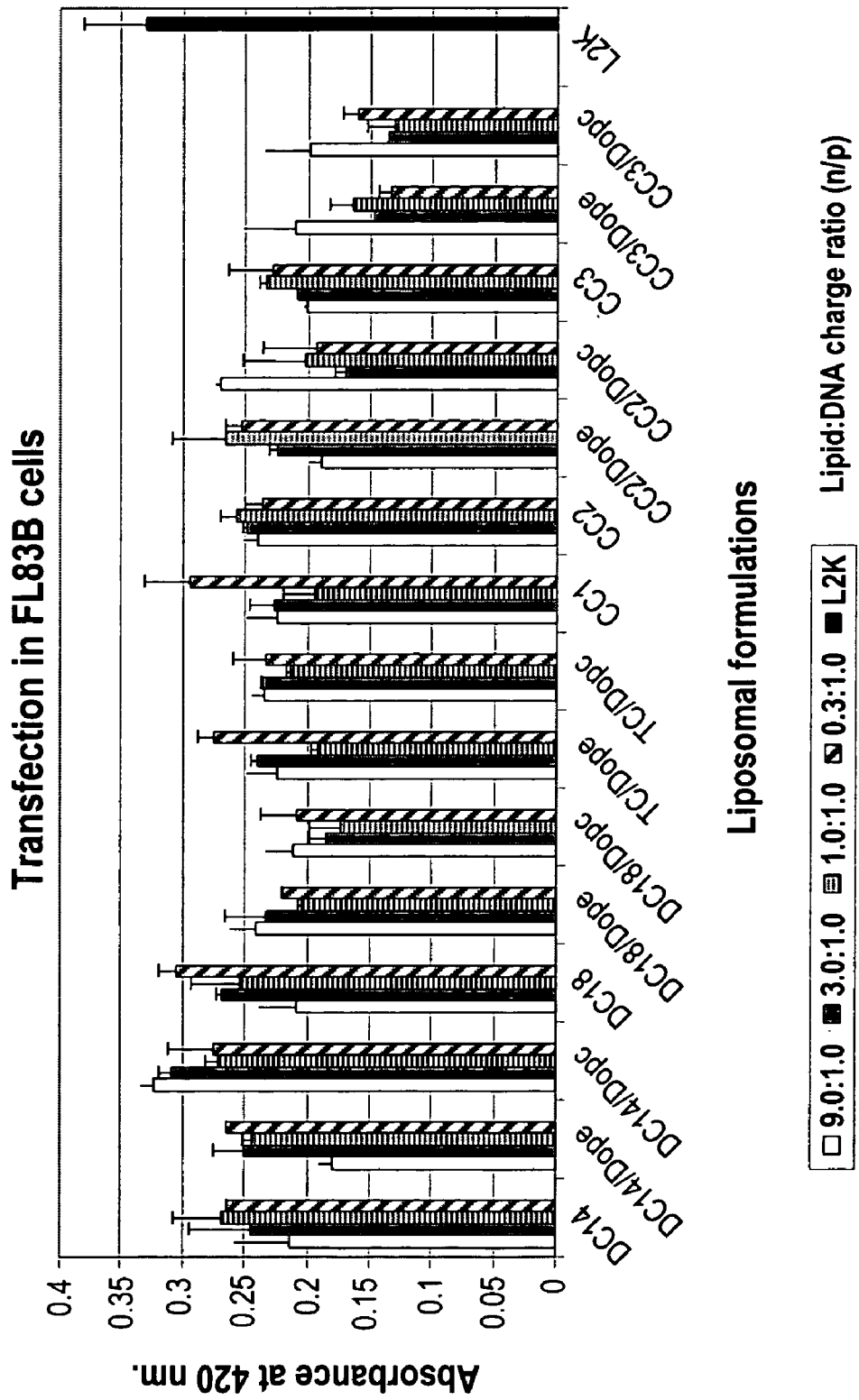
Figure 17:
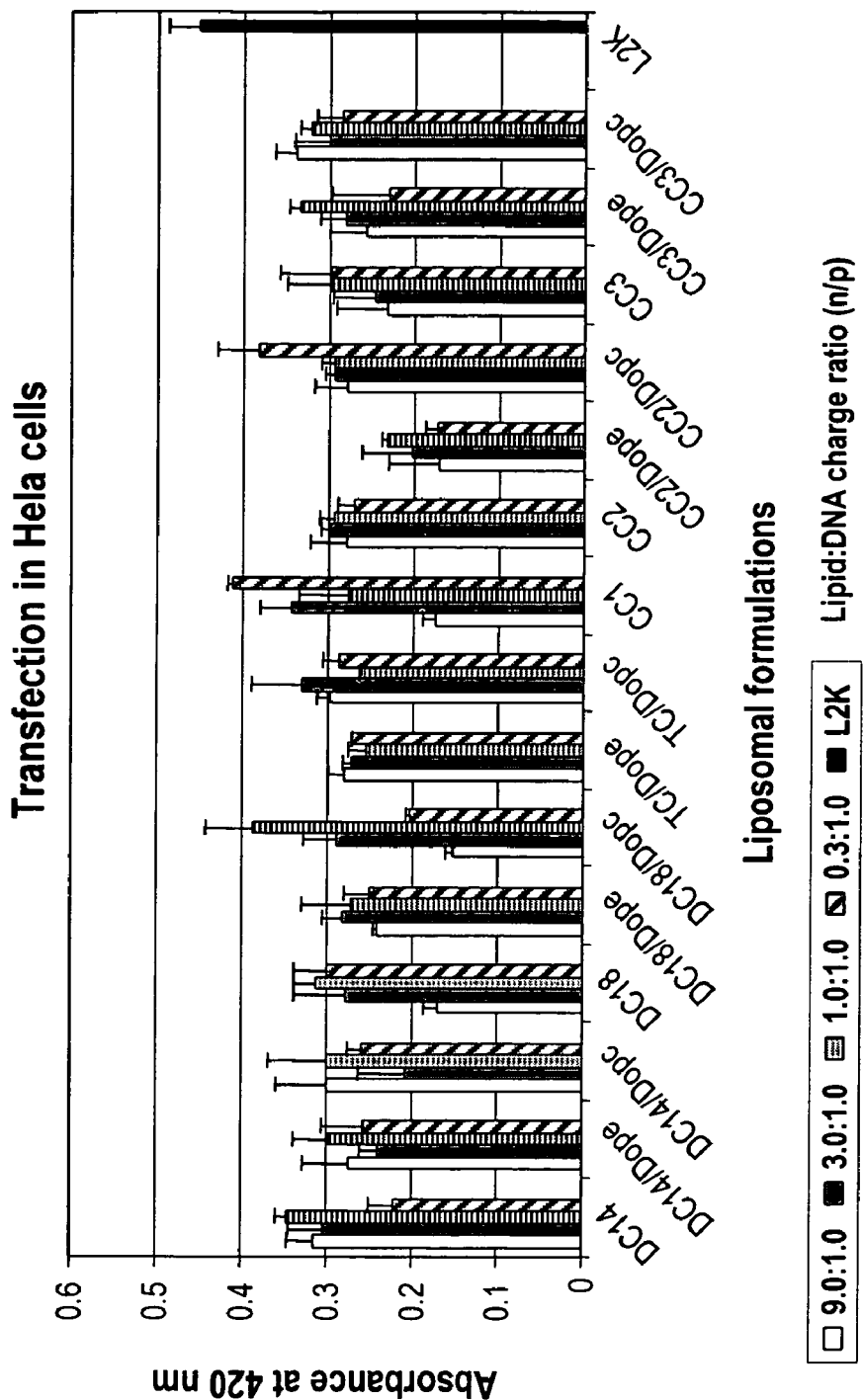

Lipid 16 (labeled as CC3) alone or in combination with co-lipids DOPE and DOPC have almost the same transfection efficiency over a lipid:DNA charge ratio of 9.0:1 to 0.3:1.0 in A-549 and HeLa cells. In A-549 the transfection efficiency is less by about a little more than one fold whereas in HeLa cells it is about 1.5 fold less active than Lipofectamine 2000. In FL83B cells the transfection efficiency of the lipid alone or in combination with co-lipids was about two fold less than Lipofectamine 2000. The transfection efficiency of the lipids alone is striking since generally lipids are found to be more transfection efficient when used in combination with a co-lipid (see FIGS. 15-17).

Accordingly, these data indicate that the lipids of the invention, alone or in combination, can be used to efficiently transfect eukaryotic cells with a nucleic acid agent.

EXAMPLE 4

Lipid Compositions for Introducing Therapeutic Agents into Cells In Vitro

The following example describes methods and compositions for introducing a therapeutic agent, in particular, an RNAi agent, into cells in vitro.

Figure 8:
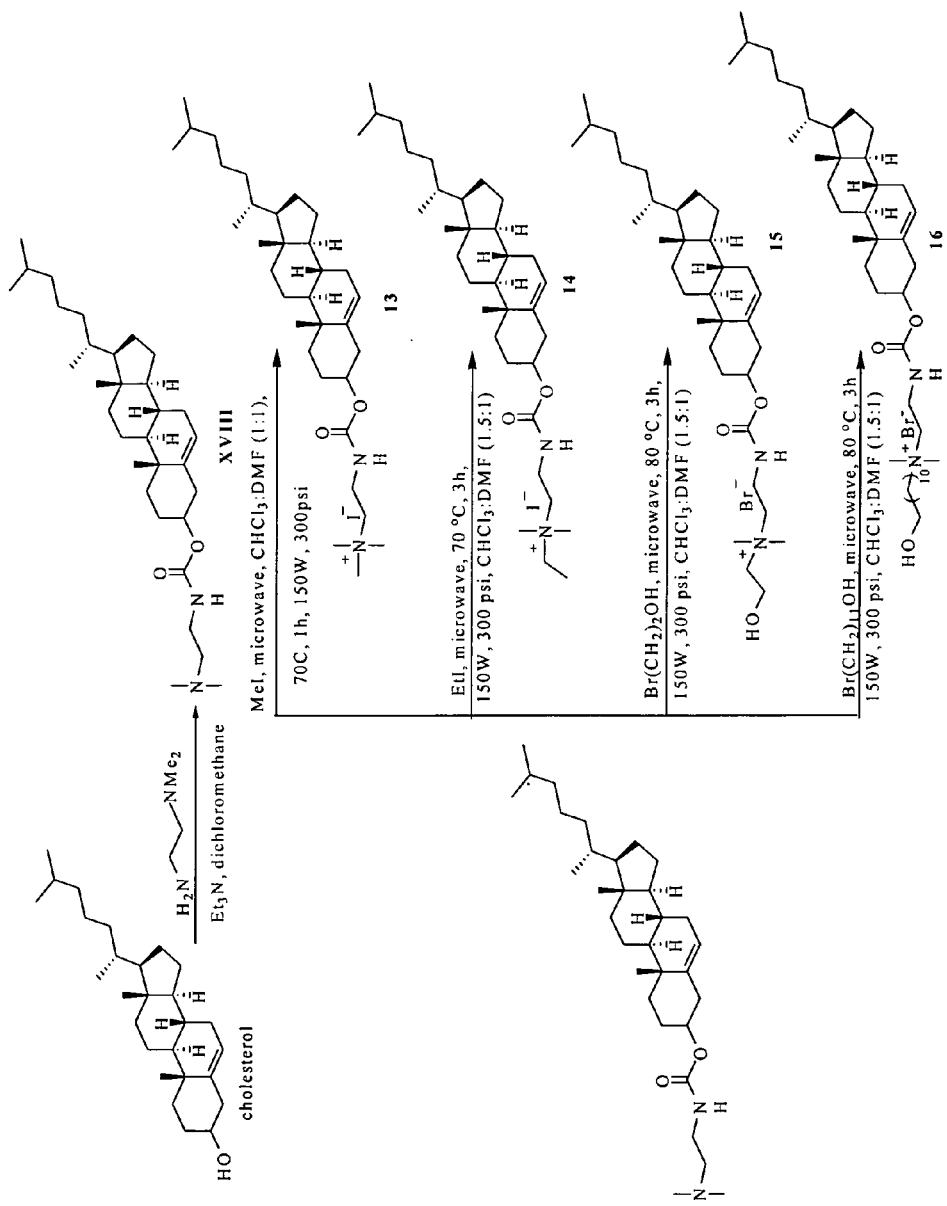
FIG. 8 shows a synthesis scheme describing the preparation of compounds 13-16 wherein the final step is carried out using microwave irradiation.
Figure 9:
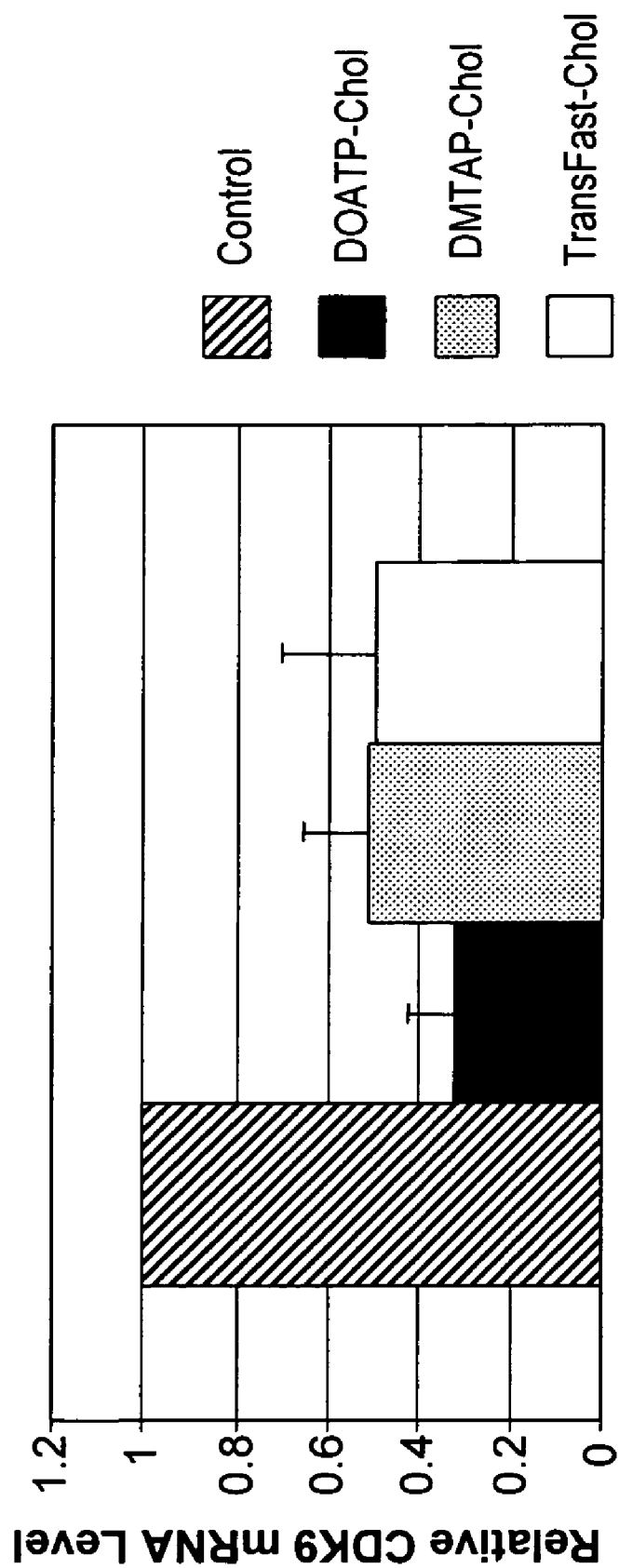
FIG. 9 shows a histogram showing the efficacy of the lipid compounds of the invention for delivery of a gene knock down RNAi agent whereby a ~50% reduction in target gene expression as compared to a control is achieved.

Briefly, a CDK9 siRNA was employed to investigate new synthesized liposome-mediated delivery in cells. FL83B cells were transfected with CDk9 siRNA using new synthesized liposome, and RNAi activity was monitored with real-time RT-PCR. The data showed varying degrees of RNAi activity with different liposome, and the highest level of RNAi activity (67% knockdown of CDK9 expression) was observed with DOTAP-Chol (FIG. 8).

FIG. 6 shows the cytotoxicity results obtained using new synthesized liposome. All cytotoxicity measurements were performed after 24 h of incubation with new synthesizes liposome without medium changes. For liposome in the range of concentrations (20 to 50 µg/ml), the cytotoxicity was very low. The highest (12% cell death) was observed with TransFast-Chol (50 µg/ml).

Accordingly, the data obtained from these experiments indicates that therapeutic agents, and in particular, nucleic acid agents such as siRNA can be delivered to cells in vitro at high efficiency and low toxicity and are capable of silencing the expression of a target gene.

EXAMPLE 5

Lipid Compositions for Introducing Therapeutic Agents into Cells In Vivo

The following example describes methods and compositions for introducing a therapeutic agent, in particular, an RNAi agent, into cells in vivo.

Figure 11:
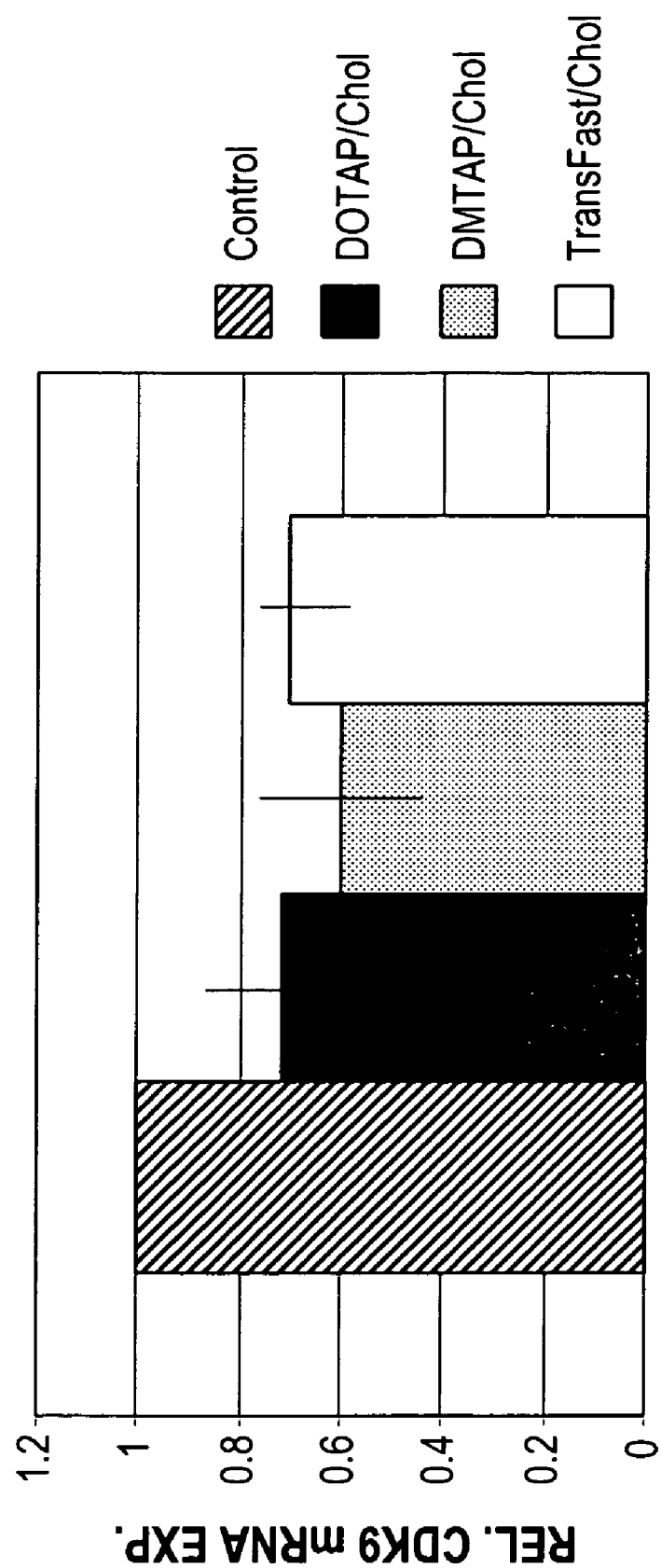
FIG. 11 shows a histogram showing the in vivo efficacy of the lipid compounds of the invention for delivery of a gene knock down RNAi agent whereby a ~40% reduction in target gene expression as compared to a control is achieved.

Briefly, the ability of the new synthesized liposome to deliver siRNA in mice was investigated. BALB/c mice were administrated with complexes of Cy3-labeled CDk9 siRNA (25 µg) and liposome (125 µg) via normal pressure tail vein injection. The injection was repeated 4 and 8 h later. Control mice were administrated with an equal amount of liposome. The delivery of siRNA using liposome gave a CDK9 expression level in the spleen decreased by 40% (DMTAP-Chol), 30% (TransFast-Chol) and 28% (DOTAP-Chol) respectively, within the initial 24 h after treatment (FIG. 11).

The tissue distribution patterns of siRNA delivered in BALB/c mice using DOTAP-Chol were assessed by fluorescence microscopy. Tissues from the mice receiving Cy3-labeled siRNA showed a significant uptake by some organs. At 24 h after injection, the highest fluorescent intensity was observed in the spleen, the lung and the liver.

Accordingly, the data obtained from these experiments indicates that therapeutic agents, and in particular, nucleic acid agents such as siRNA can be delivered to certain cells and/or tissues in vivo using the lipid compositions of the invention. SiRNAs delivered in this way are capable of silencing the expression of target gene.

EQUIVALENTS

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including reaction times, reaction size/volume, and experimental reagents, such as solvents, catalysts, pressures, atmospheric conditions, e.g., nitrogen atmosphere, and reducing/oxidizing agents, etc., with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The invention claimed is:

1. A compound having the structure

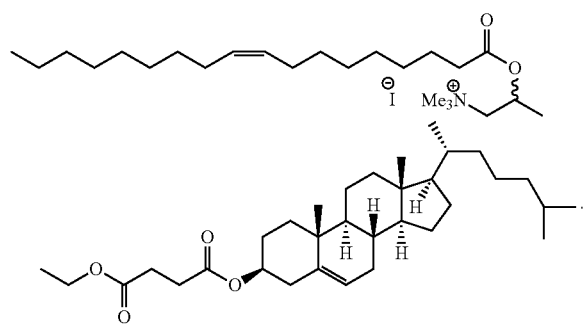

2. A lipid composition comprising the compound of claim 1.

3. The composition of claim 2, further comprising a nucleic acid agent.

4. The composition of claim 3, wherein the nucleic acid agent is a nucleic acid selected from the group consisting of expression vector, DNA plasmid, RNA transcript, RNAi, siRNA, shRNA, and miRNA.

5. The composition of claim 4, wherein the nucleic acid is an siRNA.

6. A method for introducing a nucleic acid agent into cells, the method comprising contacting cells with the composition of any one of claims 3 to 5.

* * * * *

UNITED STATES PATENT AND TRADEMARK OFFICE
CERTIFICATE OF CORRECTION

PATENT NO.       : 8,329,681 B2
APPLICATION NO.  : 11/503531
DATED            : December 11, 2012
INVENTOR(S)      : Tariq M. Rana Page 1 of 1

It is certified that error appears in the above-identified patent and that said Letters Patent is hereby corrected as shown below:

In the Specification:

Please replace the paragraph at column 1, lines 15-22 with the following paragraph:

--STATEMENT AS TO FEDERALLY SPONSORED RESEARCH

This invention was made with government support under grant nos. AI041404 and AI043198 awarded by the National Institutes of Health. The Government has certain rights in the invention.--

Signed and Sealed this
Nineteenth Day of March, 2013

Teresa Stanek Rea
*Acting Director of the United States Patent and Trademark Office*

SEQUENCE LISTING

```
<160> NUMBER OF SEQ ID NOS: 3

<210> SEQ ID NO 1
<211> LENGTH: 19
<212> TYPE: DNA
<213> ORGANISM: Artificial sequence
<220> FEATURE:
<223> OTHER INFORMATION: Description of Artificial Sequence: Synthetic
      oligonucleotide

<400> SEQUENCE: 1
```

```
ccaaagcctc accgtataa                                                        19

<210> SEQ ID NO 2
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotide

<400> SEQUENCE: 2
ccaaagccuc accguauaa                                                        19

<210> SEQ ID NO 3
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotide

<400> SEQUENCE: 3
uuauacggug aggcuuugg                                                        19
```